(12) United States Patent
Chou et al.

(10) Patent No.: US 11,788,129 B2
(45) Date of Patent: Oct. 17, 2023

(54) NUCLEIC ACID DETECTION KIT AND NUCLEIC ACID DETECTION METHOD

(71) Applicant: Industrial Technology Research Institute, Hsinchu (TW)

(72) Inventors: Min-Yuan Chou, Taipei (TW); Kuang-Chi Cheng, Zhudong Township (TW); Ming-Hua Yang, Zhubei (TW); Jiun-Lin Guo, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 146 days.

(21) Appl. No.: 17/548,037

(22) Filed: Dec. 10, 2021

(65) Prior Publication Data
US 2022/0267828 A1 Aug. 25, 2022

Related U.S. Application Data

(60) Provisional application No. 63/152,492, filed on Feb. 23, 2021.

(30) Foreign Application Priority Data
Nov. 23, 2021 (TW) .................................. 110143526

(51) Int. Cl.
| C12Q 1/6876 | (2018.01) |
| C12Q 1/6853 | (2018.01) |
| C12Q 1/686 | (2018.01) |
| C12Q 1/6851 | (2018.01) |

(52) U.S. Cl.
CPC ........... *C12Q 1/686* (2013.01); *C12Q 1/6851* (2013.01); *C12Q 1/6853* (2013.01); *C12Q 1/6876* (2013.01); *C12Q 2600/16* (2013.01)

(58) Field of Classification Search
None
See application file for complete search history.

(56) References Cited

U.S. PATENT DOCUMENTS

| 6,410,278 B1 | 6/2002 | Notomi et al. |
| 7,312,053 B2 | 12/2007 | Tada et al. |
| 7,316,901 B2 | 1/2008 | Tomita et al. |
| 7,374,879 B2 | 5/2008 | Mori et al. |
| 7,374,913 B2 | 5/2008 | Nagamine |
| 8,017,357 B2 | 9/2011 | Notomi et al. |
| 8,198,052 B2 | 6/2012 | Tada |
| 8,399,261 B2 | 3/2013 | Kabir et al. |
| 8,557,523 B2 | 10/2013 | Yonekawa et al. |
| 8,709,792 B2 | 4/2014 | Saul et al. |
| 9,976,176 B2 | 5/2018 | Bau et al. |
| 10,480,036 B2 | 11/2019 | Mokkapati et al. |
| 10,590,472 B2 | 3/2020 | Zheng |
| 10,662,485 B2 | 5/2020 | Ecker et al. |
| 2005/0164190 A1* | 7/2005 | Tada ............... C12Q 1/6851 435/6.14 |

FOREIGN PATENT DOCUMENTS

| CN | 107287320 A | 10/2017 |
| CN | 111321249 A | 6/2020 |
| CN | 111778359 A | 10/2020 |

OTHER PUBLICATIONS

GenBank Accession No. NM_001256799.1, *Homo sapiens* glyceraldehyde-3-phosphate dehydrogenase (GAPDH), transcript variant 2, mRNA, 2012. (Year: 2012).*
Ding, S., et al, "Sequence-specific and multiplex detection of Covid-19 virus (SARS-CoV-2) using proofreading enzyme-mediated probe cleavage coupled with isothermal amplification", Biosensors and Bioelectronics, 2021, vol. 178, pp. 1-6 (w/ Supplementary Information, pp. 1-10).
Taiwanese Office Action for Appl. No. 110143526 dated Jan. 5, 2023.
Huang et al., "A Rapid and Specific Assay for the Detection of MERS-CoV", Frontiers in Microbiology, 2018, vol. 9, pp. 1-9.
Zhu et al., "Reverse transcription loop-mediated isothermal amplification combined with nanoparticles-based biosensor for diagnosis of Covid-19", medRxiv, 2020, pp. 1-19.
Zhu et al., "RNA-Dependent RNA Polymerase as a Target for Covid-19 Drug Discovery", SLAS Discovery, 2020, vol. 25, No. 10, pp. 1141-1151.

* cited by examiner

*Primary Examiner* — Samuel C Woolwine
*Assistant Examiner* — Carolyn L Greene
(74) *Attorney, Agent, or Firm* — Birch, Stewart, Kolasch & Birch, LLP

(57) ABSTRACT

A GAPDH nucleic acid detection kit includes a primer set for detecting GAPDH nucleic acid. The primer set for detecting GAPDH nucleic acid includes a forward inner primer for GAPDH nucleic acids, a forward outer primer for GAPDH nucleic acids, a backward inner primer for GAPDH nucleic acids and a backward outer primer for GAPDH nucleic acids. The primer set for detecting GAPDH nucleic acid is used in a loop-mediated isothermal amplification (LAMP).

21 Claims, 19 Drawing Sheets

Specification includes a Sequence Listing.

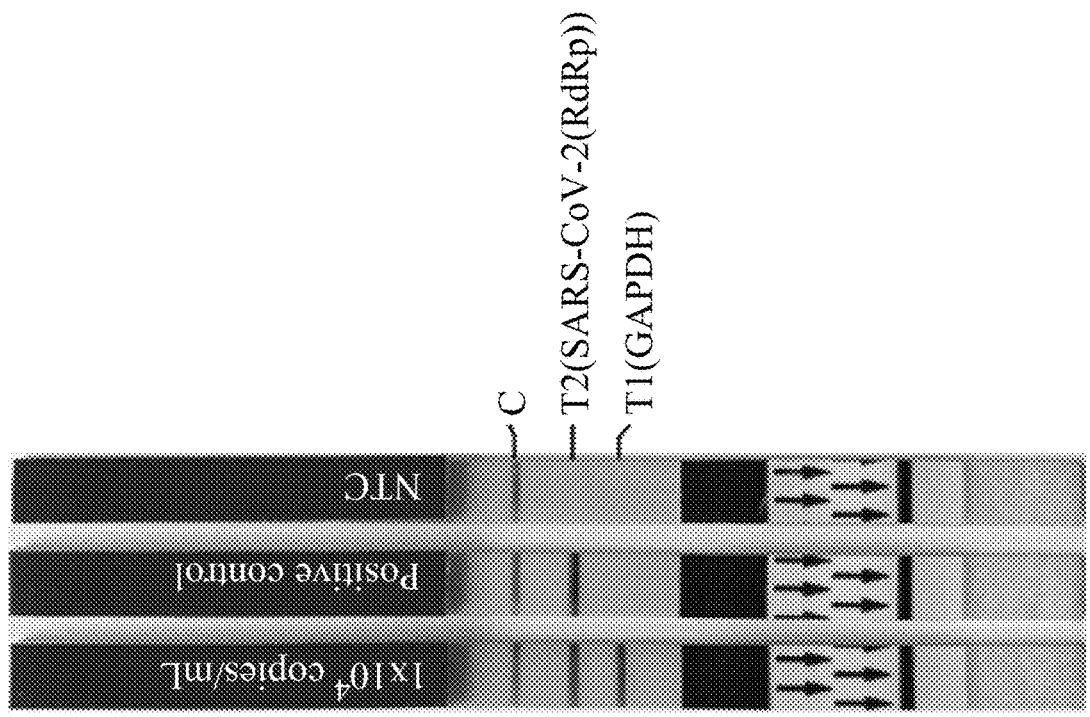
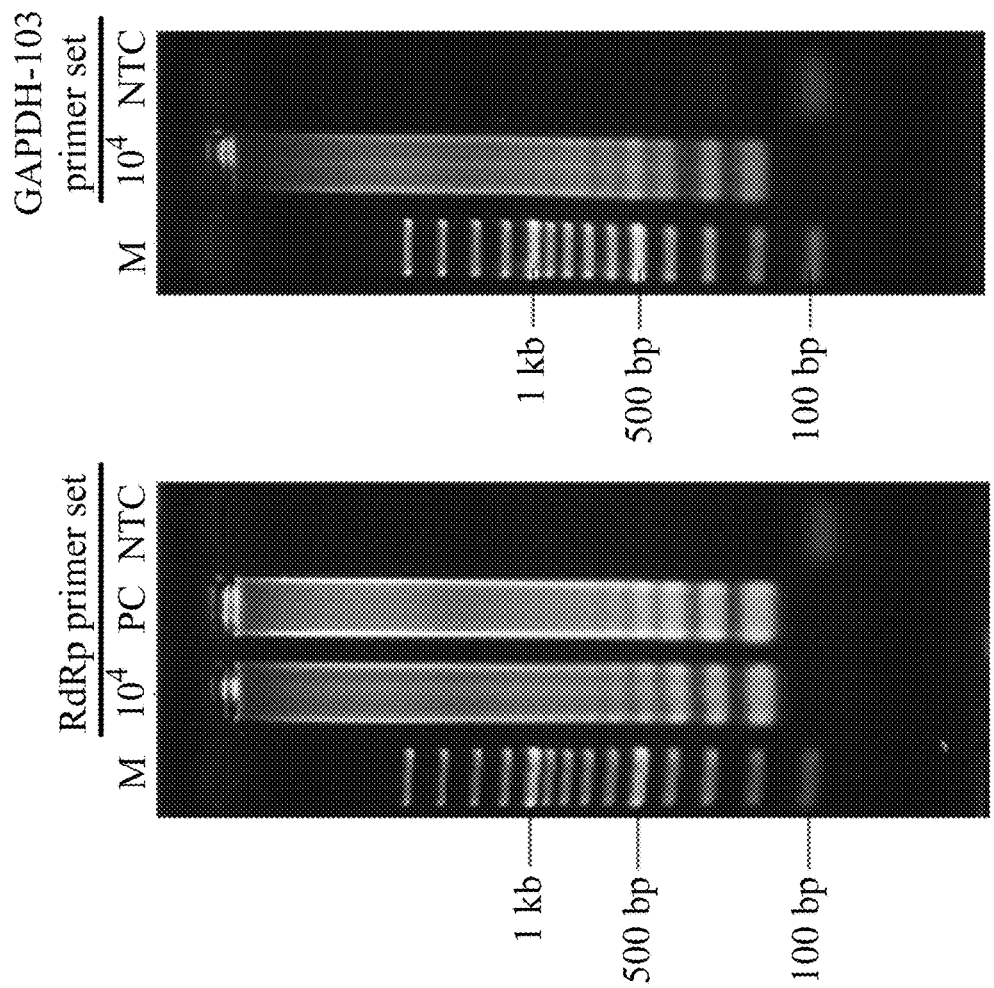
FIG. 3C
FIG. 3B
FIG. 3A

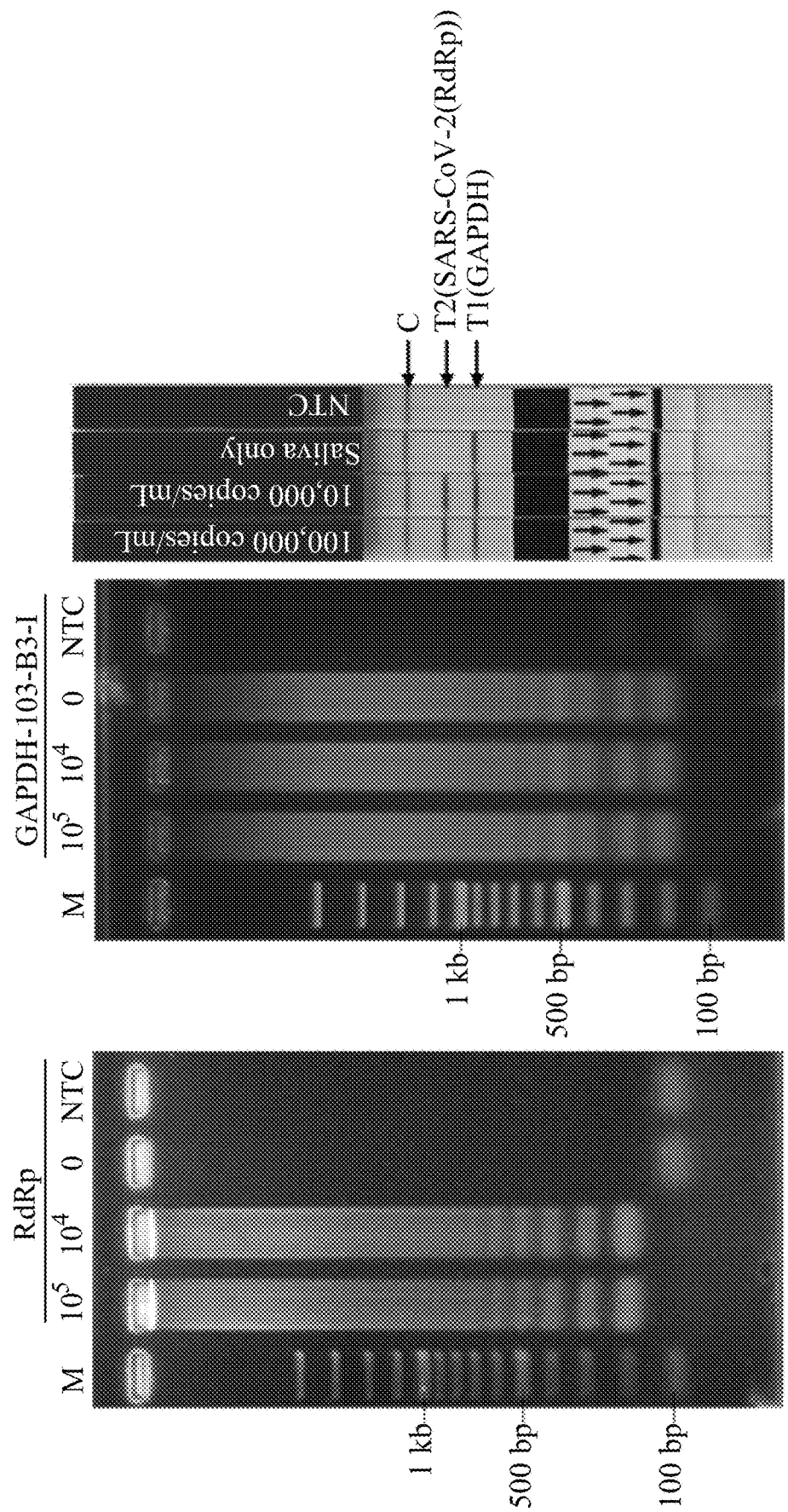

SEQUENCE LISTING

<160> NUMBER OF SEQ ID NOS: 43

<210> SEQ ID NO 1
<211> LENGTH: 600
<212> TYPE: DNA
<213> ORGANISM: Homo sapiens

<400> SEQUENCE: 1

```
aatcccatca ccatcttcca ggagcgagat ccctccaaaa tcaagtgggg cgatgctggc    60
gctgagtacg tcgtggagtc cactggcgtc ttcaccacca tggagaaggc tggggctcat   120
ttgcaggggg gagccaaaag ggtcatcatc tctgcccccct ctgctgatgc ccccatgttc   180
gtcatgggtg tgaaccatga gaagtatgac aacagcctca agatcatcag caatgcctcc   240
tgcaccacca actgcttagc acccctggcc aaggtcatcc atgacaactt tggtatcgtg   300
gaaggactca tgaccacagt ccatgccatc actgccaccc agaagactgt ggatggcccc   360
tccgggaaac tgtggcgtga tggccgcggg gctctccaga acatcatccc tgcctctact   420
ggcgctgcca aggctgtggg caaggtcatc cctgagctga acgggaagct cactggcatg   480
gccttccgtg tccccactgc caacgtgtca gtggtggacc tgacctgccg tctagaaaaa   540
cctgccaaat atgatgacat caagaaggtg gtgaagcagg cgtcggaggg cccccctcaag   600
```

<210> SEQ ID NO 2
<211> LENGTH: 47
<212> TYPE: DNA
<213> ORGANISM: Artificial Sequence
<220> FEATURE:
<223> OTHER INFORMATION: Forward inner primer

<400> SEQUENCE: 2
agcagagggg gcagagatga tgttttttcg tcttcaccac catggag    47

<210> SEQ ID NO 3
<211> LENGTH: 18
<212> TYPE: DNA
<213> ORGANISM: Artificial Sequence
<220> FEATURE:
<223> OTHER INFORMATION: Forward outer primer

<400> SEQUENCE: 3
gatgctggcg ctgagtac    18

<210> SEQ ID NO 4
<211> LENGTH: 48
<212> TYPE: DNA
<213> ORGANISM: Artificial Sequence
<220> FEATURE:
<223> OTHER INFORMATION: Backward inner primer

<400> SEQUENCE: 4
tgttcgtcat gggtgtgaac cattttttgg aggcattgct gatgatct    48

<210> SEQ ID NO 5
<211> LENGTH: 18
<212> TYPE: DNA
<213> ORGANISM: Artificial Sequence
<220> FEATURE:
<223> OTHER INFORMATION: Backward outer primer

<400> SEQUENCE: 5
ggggtgctaa gcagttgg    18

<210> SEQ ID NO 6
<211> LENGTH: 46
<212> TYPE: DNA
<213> ORGANISM: Artificial Sequence
<220> FEATURE:
<223> OTHER INFORMATION: Backward inner primer

<400> SEQUENCE: 6
tgttcgtcat gggtgtgaac catttttttgg tgcaggaggc attgct       46

<210> SEQ ID NO 7
<211> LENGTH: 46
<212> TYPE: DNA
<213> ORGANISM: Artificial Sequence
<220> FEATURE:
<223> OTHER INFORMATION: Backward inner primer

<400> SEQUENCE: 7
tgttcgtcat gggtgtgaac catttttttgt gcaggaggca ttgctg       46

<210> SEQ ID NO 8
<211> LENGTH: 46
<212> TYPE: DNA
<213> ORGANISM: Artificial Sequence
<220> FEATURE:
<223> OTHER INFORMATION: Backward inner primer
<220> FEATURE:
<221> NAME/KEY: misc_feature
<222> LOCATION: (34)..(38)
<223> OTHER INFORMATION: n is inosine

<400> SEQUENCE: 8
tgttcgtcat gggtgtgaac catttttttgg tgcnnnnngc attgct       46

<210> SEQ ID NO 9
<211> LENGTH: 18
<212> TYPE: DNA
<213> ORGANISM: Artificial Sequence
<220> FEATURE:
<223> OTHER INFORMATION: Backward outer primer
<220> FEATURE:
<221> NAME/KEY: misc_feature
<222> LOCATION: (8)..(12)
<223> OTHER INFORMATION: n is inosine

<400> SEQUENCE: 9
ggggtgcnnn nnagttgg       18

<210> SEQ ID NO 10
<211> LENGTH: 637
<212> TYPE: PRT
<213> ORGANISM: Artificial Sequence
<220> FEATURE:
<223> OTHER INFORMATION: Bst DNA polymerase large fragment

<400> SEQUENCE: 10

Met Gly Ser Ser His His His His His His Ser Gly Gly Pro Glu Gln
1               5                   10                  15

Lys Leu Ile Ser Glu Glu Asp Leu Pro Gly Gly Ser Trp Ser His Pro
            20                  25                  30

Gln Phe Glu Lys Ser Gly Leu Val Pro Arg Gly Ser Gly Arg Ala Val
        35                  40                  45

Gln Thr Asp Glu Gly Glu Lys Pro Leu Ala Gly Met Asp Phe Ala Ile
    50                  55                  60

Ala Asp Ser Val Thr Asp Glu Met Leu Ala Asp Lys Ala Ala Leu Val
65                  70                  75                  80

Val Glu Val Val Gly Asp Asn Tyr His His Ala Pro Ile Val Gly Ile
                85                  90                  95

Ala Leu Ala Asn Glu Arg Gly Arg Phe Phe Leu Arg Pro Glu Thr Ala
            100                 105                 110

Leu Ala Asp Pro Lys Phe Leu Ala Trp Leu Gly Asp Glu Thr Lys Lys
        115                 120                 125

```
Lys Thr Met Phe Asp Ser Lys Arg Ala Ala Val Ala Leu Lys Trp Lys
        130                 135                 140

Gly Ile Glu Leu Arg Gly Val Val Phe Asp Leu Leu Leu Ala Ala Tyr
145                 150                 155                 160

Leu Leu Asp Pro Ala Gln Ala Ala Gly Asp Val Ala Ala Val Ala Lys
                165                 170                 175

Met His Gln Tyr Glu Ala Val Arg Ser Asp Glu Ala Val Tyr Gly Lys
            180                 185                 190

Gly Ala Lys Arg Thr Val Pro Asp Glu Pro Thr Leu Ala Glu His Leu
        195                 200                 205

Val Arg Lys Ala Ala Ala Ile Trp Ala Leu Glu Glu Pro Leu Met Asp
210                 215                 220

Glu Leu Arg Arg Asn Glu Gln Asp Arg Leu Leu Thr Glu Leu Glu Gln
225                 230                 235                 240

Pro Leu Ala Gly Ile Leu Ala Asn Met Glu Phe Thr Gly Val Lys Val
                245                 250                 255

Asp Thr Lys Arg Leu Glu Gln Met Gly Ala Glu Leu Thr Glu Gln Leu
            260                 265                 270

Gln Ala Val Glu Arg Arg Ile Tyr Glu Leu Ala Gly Gln Glu Phe Asn
        275                 280                 285

Ile Asn Ser Pro Lys Gln Leu Gly Thr Val Leu Phe Asp Lys Leu Gln
290                 295                 300

Leu Pro Val Leu Lys Lys Thr Lys Thr Gly Tyr Ser Thr Ser Ala Asp
305                 310                 315                 320

Val Leu Glu Lys Leu Ala Pro His His Glu Ile Val Glu His Ile Leu
                325                 330                 335

His Tyr Arg Gln Leu Gly Lys Leu Gln Ser Thr Tyr Ile Glu Gly Leu
            340                 345                 350

Leu Lys Val Val His Pro Val Thr Gly Lys Val His Thr Met Phe Asn
        355                 360                 365

Gln Ala Leu Thr Gln Thr Gly Arg Leu Ser Ser Val Glu Pro Asn Leu
370                 375                 380

Gln Asn Ile Pro Ile Arg Leu Glu Glu Gly Arg Lys Ile Arg Gln Ala
385                 390                 395                 400

Phe Val Pro Ser Glu Pro Asp Trp Leu Ile Phe Ala Ala Asp Tyr Ser
                405                 410                 415

Gln Ile Glu Leu Arg Val Leu Ala His Ile Ala Glu Asp Asp Asn Leu
            420                 425                 430

Ile Glu Ala Phe Arg Arg Gly Leu Asp Ile His Thr Lys Thr Ala Met
        435                 440                 445

Asp Ile Phe His Val Ser Glu Glu Asp Val Thr Ala Asn Met Arg Arg
450                 455                 460

Gln Ala Lys Ala Val Asn Phe Gly Ile Val Tyr Gly Ile Ser Asp Tyr
465                 470                 475                 480

Gly Leu Ala Gln Asn Leu Asn Ile Thr Arg Lys Glu Ala Ala Glu Phe
                485                 490                 495

Ile Glu Arg Tyr Phe Ala Ser Phe Pro Gly Val Lys Gln Tyr Met Asp
            500                 505                 510

Asn Ile Val Gln Glu Ala Lys Gln Lys Gly Tyr Val Thr Thr Leu Leu
        515                 520                 525

His Arg Arg Arg Tyr Leu Pro Asp Ile Thr Ser Arg Asn Phe Asn Val
530                 535                 540
```

```
Arg Ser Phe Ala Glu Arg Thr Ala Met Asn Thr Pro Ile Gln Gly Ser
545                 550                 555                 560

Ala Ala Asp Ile Ile Lys Lys Ala Met Ile Asp Leu Ser Val Arg Leu
                565                 570                 575

Arg Glu Glu Arg Leu Gln Ala Arg Leu Leu Leu Gln Val His Asp Glu
            580                 585                 590

Leu Ile Leu Glu Ala Pro Lys Glu Glu Ile Glu Arg Leu Cys Arg Leu
        595                 600                 605

Val Pro Glu Val Met Glu Gln Ala Val Ala Leu Arg Val Pro Leu Lys
    610                 615                 620

Val Asp Tyr His Tyr Gly Pro Thr Trp Tyr Asp Ala Lys
625                 630                 635

<210> SEQ ID NO 11
<211> LENGTH: 300
<212> TYPE: DNA
<213> ORGANISM: Severe acute respiratory syndrome coronavirus 2

<400> SEQUENCE: 11
aaatgtgata gagccatgcc taacatgctt agaattatgg cctcacttgt tcttgctcgc    60
aaacatacaa cgtgttgtag cttgtcacac cgtttctata gattagctaa tgagtgtgct   120
caagtattga gtgaaatggt catgtgtggc ggttcactat atgttaaacc aggtggaacc   180
tcatcaggag atgccacaac tgcttatgct aatagtgttt ttaacatttg tcaagctgtc   240
acggccaatg ttaatgcact tttatctact gatggtaaca aaattgccga taagtatgtc   300

<210> SEQ ID NO 12
<211> LENGTH: 49
<212> TYPE: DNA
<213> ORGANISM: Artificial Sequence
<220> FEATURE:
<223> OTHER INFORMATION: Forward inner primer

<400> SEQUENCE: 12
cttgagcaca ctcattagct aatctttttt tgctcgcaaa catacaacg                49

<210> SEQ ID NO 13
<211> LENGTH: 18
<212> TYPE: DNA
<213> ORGANISM: Artificial Sequence
<220> FEATURE:
<223> OTHER INFORMATION: Forward outer primer

<400> SEQUENCE: 13
atggcctcac ttgttctt                                                  18

<210> SEQ ID NO 14
<211> LENGTH: 48
<212> TYPE: DNA
<213> ORGANISM: Artificial Sequence
<220> FEATURE:
<223> OTHER INFORMATION: Backward inner primer

<400> SEQUENCE: 14
gaaatggtca tgtgtggcgg ttctttttt gtggcatctc ctgatgag                  48

<210> SEQ ID NO 15
<211> LENGTH: 18
<212> TYPE: DNA
<213> ORGANISM: Artificial Sequence
<220> FEATURE:
<223> OTHER INFORMATION: Backward outer primer
```

-continued

<400> SEQUENCE: 15
taacattggc cgtgacag                                                          18

<210> SEQ ID NO 16
<211> LENGTH: 22
<212> TYPE: DNA
<213> ORGANISM: Artificial Sequence
<220> FEATURE:
<223> OTHER INFORMATION: Forward loop primer

<400> SEQUENCE: 16
aacggtgtga caagctacaa ca                                                     22

<210> SEQ ID NO 17
<211> LENGTH: 22
<212> TYPE: DNA
<213> ORGANISM: Artificial Sequence
<220> FEATURE:
<223> OTHER INFORMATION: Backward loop primer

<400> SEQUENCE: 17
actatatgtt aaaccaggtg ga                                                     22

<210> SEQ ID NO 18
<211> LENGTH: 22
<212> TYPE: DNA
<213> ORGANISM: Homo sapiens

<400> SEQUENCE: 18
agcagagggg gcagagatga tg                                                     22

<210> SEQ ID NO 19
<211> LENGTH: 19
<212> TYPE: DNA
<213> ORGANISM: Homo sapiens

<400> SEQUENCE: 19
cgtcttcacc accatggag                                                         19

<210> SEQ ID NO 20
<211> LENGTH: 22
<212> TYPE: DNA
<213> ORGANISM: Homo sapiens

<400> SEQUENCE: 20
tgttcgtcat gggtgtgaac ca                                                     22

<210> SEQ ID NO 21
<211> LENGTH: 20
<212> TYPE: DNA
<213> ORGANISM: Homo sapiens

<400> SEQUENCE: 21
ggaggcattg ctgatgatct                                                        20

<210> SEQ ID NO 22
<211> LENGTH: 18
<212> TYPE: DNA
<213> ORGANISM: Homo sapiens

<400> SEQUENCE: 22
ggtgcaggag gcattgct                                                          18

```
<210> SEQ ID NO 23
<211> LENGTH: 18
<212> TYPE: DNA
<213> ORGANISM: Homo sapiens

<400> SEQUENCE: 23
gtgcaggagg cattgctg                                                   18

<210> SEQ ID NO 24
<211> LENGTH: 25
<212> TYPE: DNA
<213> ORGANISM: Severe acute respiratory syndrome coronavirus 2

<400> SEQUENCE: 24 cttgag

<212> TYPE: PRT
<213> ORGANISM: Artificial Sequence
<220> FEATURE:
<223> OTHER INFORMATION: Strep-tag II

<400> SEQUENCE: 30

Trp Ser His Pro Gln Phe Glu Lys
1               5

<210> SEQ ID NO 31
<211> LENGTH: 6
<212> TYPE: PRT
<213> ORGANISM: Artificial Sequence
<220> FEATURE:
<223> OTHER INFORMATION: Throme cleavage site

<400> SEQUENCE: 31

Leu Val Pro Arg Gly Ser
1               5

<210> SEQ ID NO 32
<211> LENGTH: 47
<212> TYPE: DNA
<213> ORGANISM: Artificial Sequence
<220> FEATURE:
<223> OTHER INFORMATION: Forward inner primer

<400> SEQUENCE: 32
tccacagtct tctgggtggc attttttttgg tatcgtggaa ggactca        47

<210> SEQ ID NO 33
<211> LENGTH: 20
<212> TYPE: DNA
<213> ORGANISM: Artificial Sequence
<220> FEATURE:
<223> OTHER INFORMATION: Forward outer primer

<400> SEQUENCE: 33
gccaaggtca tccatgacaa        20

<210> SEQ ID NO 34
<211> LENGTH: 46
<212> TYPE: DNA
<213> ORGANISM: Artificial Sequence
<220> FEATURE:
<223> OTHER INFORMATION: Backward inner primer

<400> SEQUENCE: 34
cggggctctc cagaacatca tcttttttga tgaccttgcc cacagc        46

<210> SEQ ID NO 35
<211> LENGTH: 18
<212> TYPE: DNA
<213> ORGANISM: Artificial Sequence
<220> FEATURE:
<223> OTHER INFORMATION: Backward outer primer

<400> SEQUENCE: 35
gcttcccgtt cagctcag        18

<210> SEQ ID NO 36
<211> LENGTH: 21
<212> TYPE: DNA
<213> ORGANISM: Homo sapiens

<400> SEQUENCE: 36

```
tccacagtct tctgggtggc a                                                     21

<210> SEQ ID NO 37
<211> LENGTH: 20
<212> TYPE: DNA
<213> ORGANISM: Homo sapiens

<400> SEQUENCE: 37
tggtatcgtg gaaggactca                                                       20

<210> SEQ ID NO 38
<211> LENGTH: 22
<212> TYPE: DNA
<213> ORGANISM: Homo sapiens

<400> SEQUENCE: 38
cggggctctc cagaacatca tc                                                    22

<210> SEQ ID NO 39
<211> LENGTH: 18
<212> TYPE: DNA
<213> ORGANISM: Homo sapiens

<400> SEQUENCE: 39
gatgaccttg cccacagc                                                         18

<210> SEQ ID NO 40
<211> LENGTH: 45
<212> TYPE: DNA
<213> ORGANISM: Artificial Sequence
<220> FEATURE:
<223> OTHER INFORMATION: Forward inner primer

<400> SEQUENCE: 40
atcacgccac agtttcccgg tttttcaca gtccatgcca tcact                            45

<210> SEQ ID NO 41
<211> LENGTH: 18
<212> TYPE: DNA
<213> ORGANISM: Artificial Sequence
<220> FEATURE:
<223> OTHER INFORMATION: Backward outer primer

<400> SEQUENCE: 41
gtgagcttcc cgttcagc                                                         18

<210> SEQ ID NO 42
<211> LENGTH: 20
<212> TYPE: DNA
<213> ORGANISM: Homo sapiens

<400> SEQUENCE: 42
atcacgccac agtttcccgg                                                       20

<210> SEQ ID NO 43
<211> LENGTH: 19
<212> TYPE: DNA
<213> ORGANISM: Homo sapiens

<400> SEQUENCE: 43
cacagtccat gccatcact                                                        19
```

NUCLEIC ACID DETECTION KIT AND NUCLEIC ACID DETECTION METHOD

CROSS REFERENCE TO RELATED APPLICATION

This application claims the benefit of U.S. Provisional Application No. 63/152,492, filed on Feb. 23, 2021, the entirety of which is incorporated by reference herein.

The present application is based on, and claims priority from, Taiwan Application Serial Number 110143526, filed on Nov. 23, 2021, the disclosure of which is hereby incorporated by reference herein in its entirety.

INCORPORATION BY REFERENCE OF SEQUENCE LISTING

A sequence listing submitted as a text file via EFS-Web is incorporated herein by reference. The text file containing the sequence listing is named "9044B-A28212-US_Seq_Listing.txt"; its date of creation is Dec. 2, 2021; and its size is 14,472 bytes.

TECHNICAL FIELD

The technical field relates to a nucleic acid detection kit and a nucleic acid detection method, and in particular to a GAPDH nucleic acid detection kit, a target nucleic acid detection kit and a severe acute respiratory syndrome coronavirus 2 (SARS-CoV-2 or 2019-nCoV) nucleic acid detection kit and the detection methods thereof.

BACKGROUND

COVID-19 is caused by severe acute respiratory syndrome coronavirus 2 (SARS-CoV-2 or 2019-nCoV) infection. As of Feb. 20, 2021, 110 million people have been infected and more than 2.46 million have died worldwide. The clinical symptoms of COVID-19 are variable, ranging from severe pneumonia, respiratory distress, loss of taste, to asymptomatic infection.

The current method for detection of SARS-CoV-2 mainly comprises collecting upper respiratory tract specimens (nasopharyngeal or throat swabs) or lower respiratory tract specimens (sputum, endotracheal fluid or bronchoalveolar lavage fluid), subjecting the specimen to nucleic acid extraction, followed by quantitative reverse transcription polymerase reaction (RT-qPCR, Quantitative reverse transcription PCR), and the inspection time is about 4 hours. The inspectors must wear protective measures such as gloves, isolation gown and goggles, and the process requires a lot of manpower and equipment support. In addition, the collection of upper respiratory tract specimens (nasopharyngeal or pharyngeal swabs) or lower respiratory tract specimens is an invasive collection, which may cause discomfort to the subject and cause droplet production such as sneezing or coughing, thereby creating a potential risk of virus spread.

Therefore, there is an urgent need for a novel nucleic acid detection kit and method that not only has good detection sensitivity, but also can be performed using non-invasively collected specimens.

SUMMARY

The present disclosure provides a GAPDH nucleic acid detection kit, comprising a primer set for detecting GAPDH nucleic acids. The primer set for detecting GAPDH nucleic acids comprises a forward inner primer for GAPDH nucleic acids; a forward outer primer for GAPDH nucleic acids; a backward inner primer for GAPDH nucleic acids; and a backward outer primer for GAPDH nucleic acids. The forward inner primer for GAPDH nucleic acids consists of a first segment and a second segment, and the 3' end of the first segment is connected to the 5' end of the second segment, or the forward inner primer for GAPDH nucleic acids consists of a first segment, a first linker and a second segment, and the 3' end of the first segment is connected to the 5' end of the first linker, and the 3' end of the first linker is connected to the 5' end of the second segment. The first segment has 10-30 nucleotides and consists of a complementary strand of a first sequence section, and the first sequence section is located between position 134 and position 175 of the nucleotide sequence of SEQ ID NO. 1, and the second segment has 10-30 nucleotides and consists of a second sequence section, and the second sequence section is located between position 77 and position 115 of the nucleotide sequence of SEQ ID NO. 1, and the first linker consists of 1-6 thymines or peptide nucleic acids (PNAs). The forward outer primer for GAPDH nucleic acids has 10-30 nucleotides and consists of a third sequence section, and the third sequence section is located between position 42 and position 79 of the nucleotide sequence of SEQ ID NO. 1. The backward inner primer for GAPDH nucleic acids consists of a third segment and a fourth segment, and the 3' end of the third segment is connected to the 5' end of the fourth segment, or the backward inner primer for GAPDH nucleic acids consists of a third segment, a second linker and a fourth segment, and the 3' end of the third segment is connected to the 5' end of the second linker, and the 3' end of the second linker is connected to the 5' end of the fourth segment. The third segment has 10-30 nucleotides and consists of a fourth sequence section, and the fourth sequence section is located between position 156 and position 207 of the nucleotide sequence of SEQ ID NO. 1, and the fourth segment has 10-30 nucleotides and consists of a complementary strand of a fifth sequence section, and the fifth sequence section is located between position 211 and position 250 of the nucleotide sequence of SEQ ID NO. 1, and the second linker consists of 1-6 thymines or peptide nucleic acids. The backward outer primer for GAPDH nucleic acids has 10-30 nucleotides and consists of a complementary strand of a sixth sequence section, and the sixth sequence section is located between position 238 and position 275 of the nucleotide sequence of SEQ ID NO. 1. Moreover, the GAPDH nucleic acid detection kit is used in a loop-mediated isothermal amplification (LAMP), and the loop-mediated isothermal amplification comprises a standard loop-mediated isothermal amplification or a reverse transcription loop-mediated isothermal amplification (RT-LAMP).

The present disclosure also provides a target nucleic acid detection kit, comprising: a primer set for detecting GAPDH nucleic acids and a primer set for detecting target nucleic acids. The primer set for detecting GAPDH nucleic acids comprises a forward inner primer for GAPDH nucleic acids; a forward outer primer for GAPDH nucleic acids; a backward inner primer for GAPDH nucleic acids; and a backward outer primer for GAPDH nucleic acids. The forward inner primer for GAPDH nucleic acids consists of a first segment and a second segment, and the 3' end of the first segment is connected to the 5' end of the second segment, or the forward inner primer for GAPDH nucleic acids consists of a first segment, a first linker and a second segment, and the 3' end of the first segment is connected to the 5' end of the first linker, and the 3' end of the first linker is connected to the 5' end of the second segment. The first segment has 10-30 nucleotides and consists of a complementary strand of a first sequence section, and the first sequence section is located between position 134 and position 175 of the nucleotide sequence of SEQ ID NO. 1, and the second segment has 10-30 nucleotides and consists of a second sequence section, and the second sequence section is located between position 77 and position 115 of the nucleotide sequence of SEQ ID NO. 1, and the first linker consists of 1-6 thymines or peptide nucleic acids (PNAs). The forward outer primer for GAPDH nucleic acids has 10-30 nucleotides and consists of a third sequence section, and the third sequence section is located between position 42 and position 79 of the nucleotide sequence of SEQ ID NO. 1. The backward inner primer for GAPDH nucleic acids consists of a third segment and a fourth segment, and the 3' end of the third segment is connected to the 5' end of the fourth segment, or the backward inner primer for GAPDH nucleic acids consists of a third segment, a second linker and a fourth segment, and the 3' end of the third segment is connected to the 5' end of the second linker, and the 3' end of the second linker is connected to the 5' end of the fourth segment. The third segment has 10-30 nucleotides and consists of a fourth sequence section, and the fourth sequence section is located between position 156 and position 207 of the nucleotide sequence of SEQ ID NO. 1, and the fourth segment has 10-30 nucleotides and consists of a complementary strand of a fifth sequence section, and the fifth sequence section is located between position 211 and position 250 of the nucleotide sequence of SEQ ID NO. 1, and the second linker consists of 1-6 thymines or peptide nucleic acids. The backward outer primer for GAPDH nucleic acids has 10-30 nucleotides and consists of a complementary strand of a sixth sequence section, and the sixth sequence section is located between position 238 and position 275 of the nucleotide sequence of SEQ ID NO. 1. Moreover, the primer set for detecting target nucleic acids comprises a forward inner primer for target nucleic acids; a forward outer primer for target nucleic acids; a backward inner primer for target nucleic acids; and a backward outer primer for target nucleic acids. A detection target of the primer set for detecting target nucleic acids differs from a detection target of the primer set for detecting GAPDH nucleic acids. The primer set for detecting GAPDH nucleic acids and the primer set for detecting target nucleic acids are respectively used in a first loop-mediated isothermal amplification and a second loop-mediated isothermal amplification, and the first loop-mediated isothermal amplification and the second loop-mediated isothermal amplification independently comprises a standard loop-mediated isothermal amplification or a reverse transcription loop-mediated isothermal amplification. Furthermore, a result of the first loop-mediated isothermal amplification is used as an internal control.

The present disclosure further provides a SARS-CoV-2 detection kit, comprising a primer set for detecting SARS-CoV-2 nucleic acids. The primer set for detecting SARS-CoV-2 nucleic acids comprises a forward inner primer for SARS-CoV-2 nucleic acids; a forward outer primer for SARS-CoV-2 nucleic acids; a backward inner primer for SARS-CoV-2 nucleic acids; and a backward outer primer for SARS-CoV-2 nucleic acids. the forward inner primer for SARS-CoV-2 nucleic acids consists of a fifth segment and a sixth segment, and the 3' end of the fifth segment is connected to the 5' end of the sixth segment, or the forward inner primer for target nucleic acids consists of a fifth segment, a third linker and a sixth segment, and the 3' end of the fifth segment is connected to the 5' end of the third linker, and the 3' end of the third linker is connected to the 5' end of the sixth segment. The fifth segment has 10-30 nucleotides and consists of a complementary strand of a seventh sequence section, and the seventh sequence section is located between position 90 and position 134 of the nucleotide sequence of SEQ ID NO. 11, and the sixth segment has 10-30 nucleotides and consists of an eighth sequence section, and the eighth sequence section is located between position 45 and position 82 of the nucleotide sequence of SEQ ID NO. 11, and the third linker consists of 1-6 thymines or peptide nucleic acids. The forward outer primer for SARS-CoV-2 nucleic acids has 10-30 nucleotides and consists of a ninth sequence section, and the ninth sequence section is located between position 27 and position 64 of the nucleotide sequence of SEQ ID NO. 11. Moreover, the backward inner primer for SARS-CoV-2 nucleic acids consists of a seventh segment and an eighth segment, and the 3' end of the seventh segment is connected to the 5' end of the eighth segment, or the backward inner primer for target nucleic acids consists of a seventh segment, a fourth linker and an eighth segment, and the 3' end of the seventh segment is connected to the 5' end of the fourth linker, and the 3' end of the fourth linker is connected to the 5' end of the eighth segment. The seventh segment has 10-30 nucleotides and consists of a tenth sequence section, and the tenth sequence section is located between position 123 and position 165 of the nucleotide sequence of SEQ ID NO. 11, and the eighth segment has 10-30 nucleotides and consists of a complementary strand of an eleventh sequence section, and the eleventh sequence section is located between position 170 and position 208 of the nucleotide sequence of SEQ ID NO. 11, and the fourth linker consists of 1-6 thymines or peptide nucleic acids. The backward outer primer for SARS-CoV-2 nucleic acids has 10-30 nucleotides and consists of a complementary strand of a twelfth sequence section, and the nucleotide sequence of the twelfth sequence section is located between position 226 and position 263 of SEQ ID NO. 11. In addition, the SARS-CoV-2 nucleic acid detection kit is used in a loop-mediated isothermal amplification, and the loop-mediated isothermal amplification comprises a standard loop-mediated isothermal amplification or a reverse transcription loop-mediated isothermal amplification.

Moreover, the present disclosure provides a method for detecting GAPDH nucleic acids, comprising: (a) providing a sample to be tested; and (b) performing a loop-mediated isothermal amplification on the sample to be tested by the primer set for detecting GAPDH nucleic acids in the GAPDH nucleic acid detection kit mentioned above. If the sample to be tested contains GAPDH nucleic acid, a GAPDH nucleic acid amplification product is obtained from the loop-mediated isothermal amplification. The loop-mediated isothermal amplification comprises a standard loop-mediated isothermal amplification or a reverse transcription loop-mediated isothermal amplification.

The present disclosure also provides a method for detecting SARS-CoV-2 nucleic acids, comprising: (a) providing a sample to be tested; and (b) performing a loop-mediated isothermal amplification on the sample to be tested by the primer set for detecting SARS-CoV-2 nucleic acids in the SARS-CoV-2 detection kit mentioned above. If the sample to be tested contains SARS-CoV-2 nucleic acid, a nucleic acid amplification product of SARS-CoV-2 is obtained from the loop-mediated isothermal amplification. The loop-mediated isothermal amplification comprises a standard loop-mediated isothermal amplification or a reverse transcription loop-mediated isothermal amplification.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIG. 3A shows an electrophoresis analysis result of a product obtained by performing a reverse transcription loop-mediated isothermal amplification (one-step reaction) on total RNA of a saliva specimen containing the synthetic SARS-CoV-2 RNA control with RdRp primer set (the 5' end of the forward inner primer is labeled with FAM, and the 5' end of the backward inner primer is labeled with biotin). Positive control (PC): a product obtained by directly mixing synthetic SARS-CoV-2 RNA control with RdRp primer set and RT/Bst mix and performing a reverse transcription loop-mediated isothermal amplification thereon. No template control (NTC): a product obtained by mixing 1× RNAsecure™ RNase Inactivation Reagent (used to replace the total RNA template) with RdRp primer set and RT/Bst mix and performing a reverse transcription loop-mediated isothermal amplification thereon; M: DNA molecular weight standard; PC: positive control; NTC: no template control; $10^4$: a product obtained by performing a reverse transcription loop-mediated isothermal amplification on total RNA of a saliva specimen containing $10^4$ copies/mL of synthetic SARS-CoV-2 RNA control with RdRp primer set;

FIG. 3B shows an electrophoresis analysis result of a product obtained by performing a reverse transcription loop-mediated isothermal amplification (one-step reaction) on total RNA of a saliva specimen containing the synthetic SARS-CoV-2 RNA control with the GAPDH-103 primer set (the 5' end of the forward inner primer is labeled with DIG, and the 5' end of the backward inner primer is labeled with biotin). No template control (NTC): a product obtained by mixing 1× RNAsecure™ RNase Inactivation Reagent (used to replace the total RNA template) with GAPDH-103 primer set and RT/Bst mix and performing a reverse transcription loop-mediated isothermal amplification thereon. M: DNA molecular weight standard; NTC: no template control; $10^4$: a product obtained by performing a reverse transcription loop-mediated isothermal amplification on total RNA of a saliva specimen containing $10^4$ copies/mL of synthetic SARS-CoV-2 RNA control with GAPDH-103 primer set;

FIG. 3C shows a lateral flow immunoassay result of a mixture obtained by mixing equal amount of two products which are obtained by performing reverse transcription loop-mediated isothermal amplifications (one-step reaction) on total RNA of a saliva specimen containing the synthetic SARS-CoV-2 RNA control respectively with RdRp primer set and GAPDH-103 primer set. Positive control: a product obtained by directly mixing synthetic SARS-CoV-2 RNA control with RdRp primer set and RT/Bst mix and performing a reverse transcription loop-mediated isothermal amplification thereon; No template control (NTC): a mixture obtained by taking equal amount of the no template control for FIG. 3A and the no template control for FIG. 3B and mixing them with each other; $10^4$ copies/mL: a mixture obtained by mixing equal amount of the two product which are obtained by performing reverse transcription loop-mediated isothermal amplifications (one-step reaction) on total RNA of a saliva specimen containing the synthetic SARS-CoV-2 RNA control respectively with RdRp primer set and GAPDH-103 primer set; NTC: no template control; C: control line; T1: first test line; T2: second test line;

FIG. 10A shows an electrophoresis analysis result of a product obtained by performing a reverse transcription loop-mediated isothermal amplification with RdRp primer set on a sample obtained from performing a heat treatment on a SARS-CoV-2-negative saliva specimen added with inactivated SARS-CoV-2 virus suspension. M: DNA molecular weight standard; NTC: no template control;

FIG. 10B shows an electrophoresis analysis result of a product obtained by performing a reverse transcription loop-mediated isothermal amplification with GAPDH-103-B3-I primer set on a sample obtained from performing a heat treatment on a SARS-CoV-2-negative saliva specimen added with inactivated SARS-CoV-2 virus suspension. M: DNA molecular weight standard; NTC: no template control;

FIG. 10C shows a lateral flow immunoassay result of a mixture obtained by mixing respective products obtained by performing respective reverse transcription loop-mediated isothermal amplifications with RdRp primer set and GAPDH-103-B3-I primer set on a sample obtained from performing a heat treatment on a SARS-CoV-2-negative saliva specimen added with inactivated SARS-CoV-2 virus suspension. NTC: no template control; C: control line; T1: first test line; T2: second test line;

DETAILED DESCRIPTION

Figure 1A:
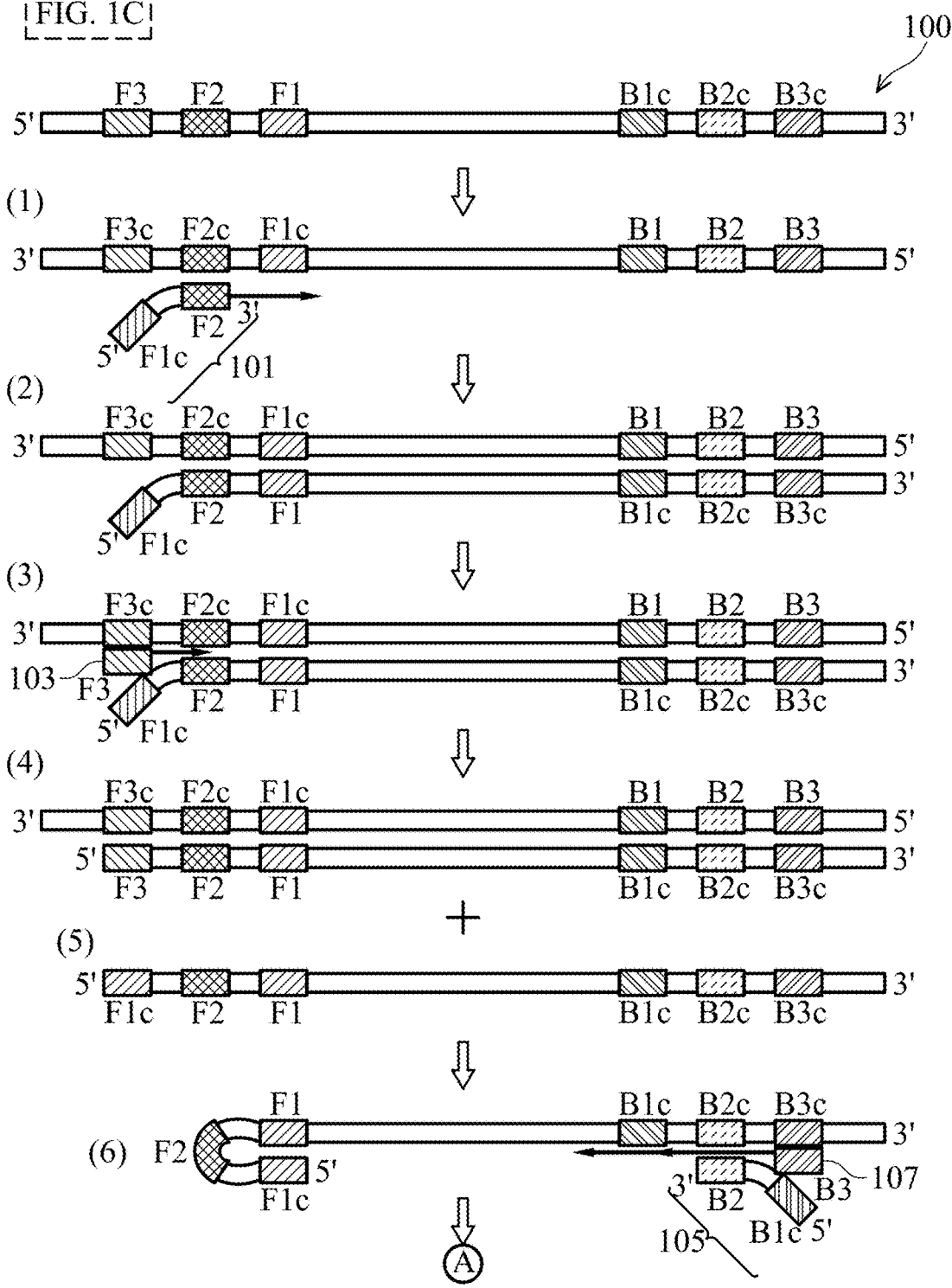
FIG. 1A, FIG. 1B and FIG. 1C show the design and operation principle for the primer set for detecting GAPDH nucleic acids in the GAPDH nucleic acid detection kit and in the target nucleic acid detection kit of the present disclosure and the design and operation principle for the primer set for detecting GAPDH nucleic acids and the primer set for detecting target nucleic acids in the target nucleic acid detection kit of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure may provide a GAPDH nucleic acid detection kit which may comprise a primer set for detecting GAPDH nucleic acids, but it is not limited thereto.

The primer set for detecting GAPDH nucleic acids in the GAPDH nucleic acid detection kit of the present disclosure mentioned above may be used in a loop-mediated isothermal amplification (LAMP) to determine whether GAPDH nucleic acids are present in a sample to be tested or not.

The loop-mediated isothermal amplification mentioned above may comprise a standard loop-mediated isothermal amplification or a reverse transcription loop-mediated isothermal amplification (RT LAMP), but it is not limited thereto.

The sample to be tested mentioned may be a sample without being subjected to any purification process, for example, without being subjected to a nucleic acid purification process. Namely, by the primer set for detecting GAPDH nucleic acids in the GAPDH nucleic acid detection kit of the present disclosure mentioned above, a nucleic acid amplification can be performed on a biosample without being subjected to any purification process to obtain an accurate GAPDH nucleic acid detection result to achieve an effect of reducing or eliminating processing a sample to be tested.

A source of the foregoing sample to be tested may comprise, but is not limited to a saliva specimen, a sputum specimen, a nose swab specimen, a throat swab specimen, a nasopharyngeal specimen, a urine specimen, a stool specimen, a rectal swab specimen, a cerebrospinal fluid (CSF) specimen, a body fluid specimen, etc.

In one embodiment, a source of the sample to be tested mentioned above may be a specimen obtained from a non-invasive sampling, such as a saliva specimen, a sputum specimen, a urine specimen and a stool specimen, but it is not limited thereto. In this embodiment, the GAPDH nucleic acid detection kit of the present disclosure may collocate with an isothermal reaction machine and a simple assay test strip, such as a lateral flow immunoassay test strip, to achieve home testing.

Moreover, the primer set for detecting GAPDH nucleic acids in the GAPDH nucleic acid detection kit of the present disclosure mentioned above may use a single-stranded RNA or first strand cDNA as an initial template to perform the loop-mediated isothermal amplification mentioned above, but it is not limited thereto.

Design of the primer set for detecting GAPDH nucleic acids in the GAPDH nucleic acid detection kit is based on an loop-mediated isothermal amplification, however, the designed primer set is not only suitable for the loop-mediated isothermal amplification. Design and operation principle for the primer set for detecting GAPDH nucleic acids in the GAPDH nucleic acid detection kit of the present disclosure mentioned above are shown in FIG. 1A, FIG. 1B and FIG. 1C.

Figure 1B:
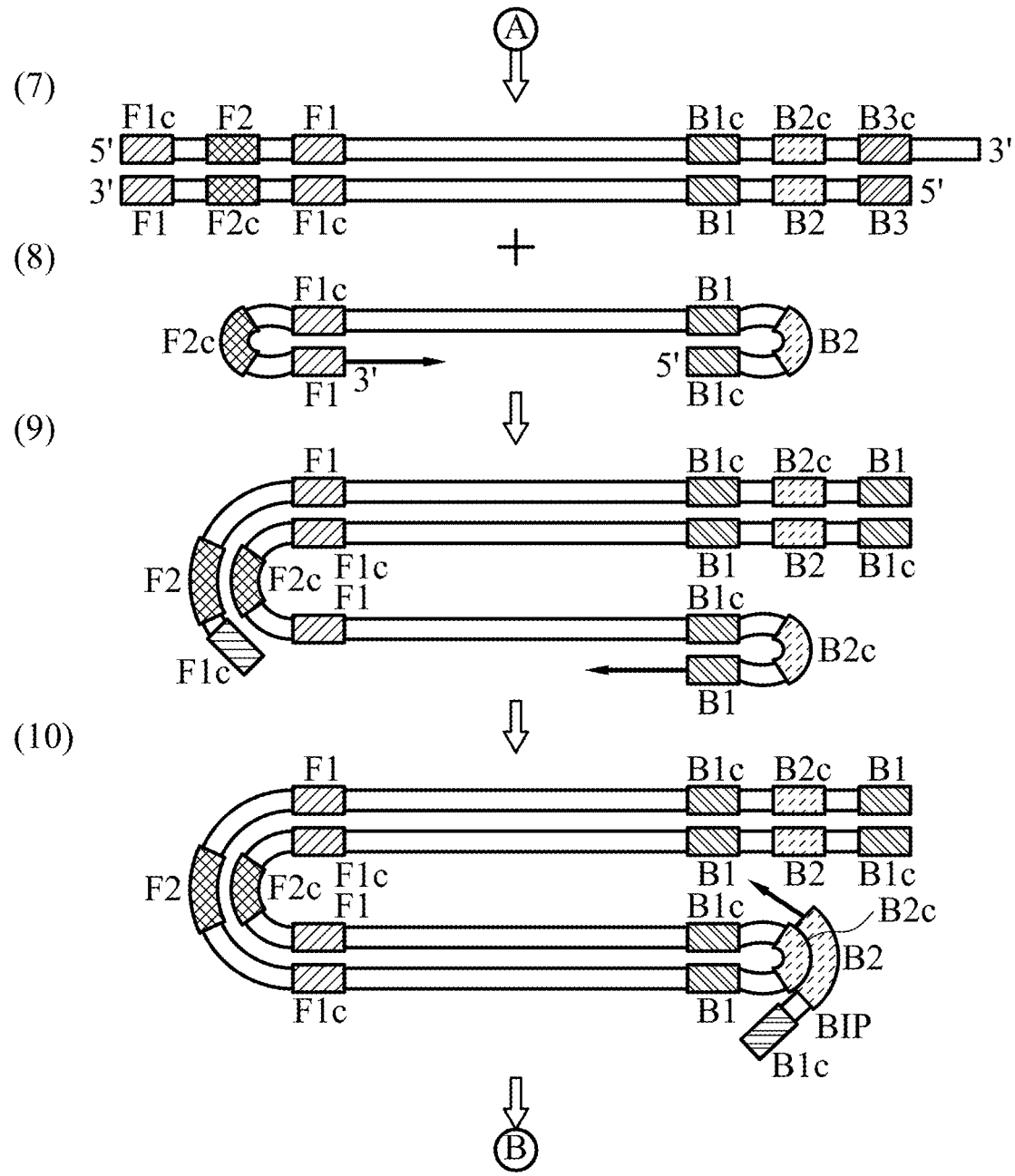
Figure 1C:
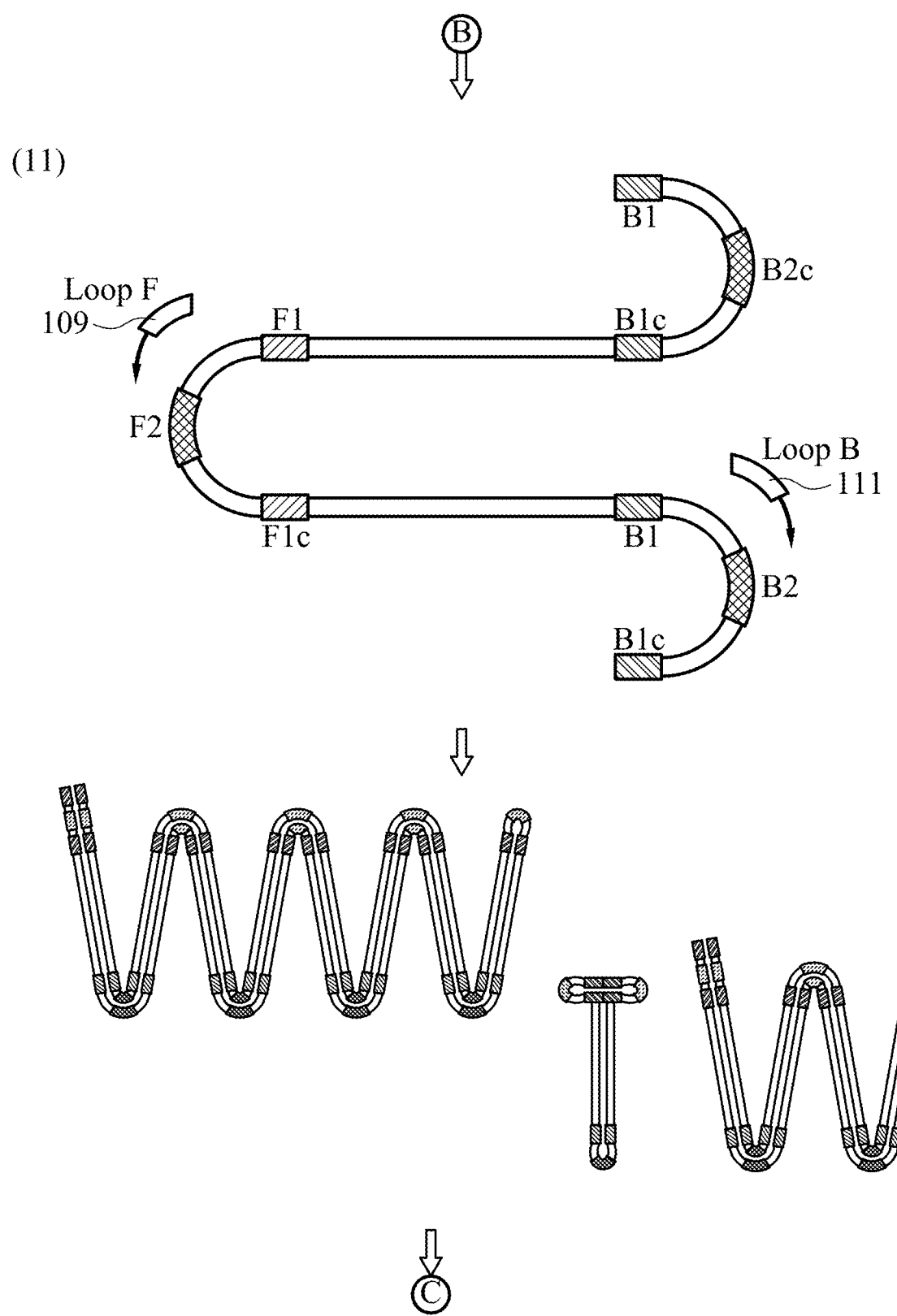

Please refer to FIG. 1A, FIG. 1B and FIG. 1C. According to FIG. 1A, it is understood that six regions are selected in a target nucleic acids (such as an RNA sequence) 100, which respectively are F1 region, F2 region, F3 region, B1c region, B2c region and B3c region (complementary sequences thereof respectively are to F1c region, F2c region, F3c region, B1 region, B2 region and B3 region). In this method, four primers are adopted, and they respectively are specially designed forward inner primer (FIP) 101, forward outer primer 103, backward inner primer (BIP) 105 and backward outer primer 107, wherein the sequence of the forward inner primer 101 consists of a first segment (a complementary strand of the sequence of F1 region, i.e. the sequence of F1c region) and a second segment (the sequence of F2 region), the sequence of the forward outer primer 103 consists of the sequence of F3 region, the sequence of the backward inner primer 105 consists of a third segment (the sequence of B1c region, i.e., a complementary strand of the sequence of B1 region) and a fourth segment (a complementary strand of the sequence of B2c region, i.e., the sequence of B2 region), and the sequence of the backward outer primer 107 consists of a complementary strand of the sequence of B3c region (i.e., the sequence of B3 region).

While performing the loop-mediated isothermal amplification, the second segment (the sequence of the F2 region) of the forward inner primer 101 will anneal to (a complementary strand (such as a cDNA) of F2c region of the target nucleic acids 100 mentioned above and proceed to a complementary strand synthesis reaction, and a first strand which has the sequences of the first segment (a complementary strand of the sequence of the F1 region, that is the sequence of the F1c region), second segment (the sequence of the F2 region), F1 region, B1c region, B2c region and B3c region is synthesized, and the forward outer primer 103 will push the strand aside and thus a second strand which has the sequences of F3 region, F2 region, F1 region, B1c region, B2c region and B3c region is synthesized. Next, the fourth segment (the sequence of the B2 region) of the backward inner primer 105 anneals to the B2c region of the foregoing first strand, and a third strand which has the sequences of B1c region, B2 region, B1 region, F1c region, F2c region and F1 region is synthesized by using the first strand as a template. After that, the backward outer primer 107 will push the third strand aside and thus a fourth strand which has the sequences of the B3 region, B2 region, B1 region, F1c region, F2c region and F1 region is synthesized. The B1c region of the third strand and B1 region of the third strand will result in self-annealing, and similarly the F1 region of the third strand and F1c region of the third strand will also result in self-annealing, and thus the third strand will become a strand with two ends each have a loop form. Then, the forward inner primer and backward inner primer continue the complementary strand synthesis reaction by using the complementary strand synthesis products of the third strand and/or the complementary strand thereof as the template in turn, and a double-strand product which has a plurality of loops is formed (please refer to FIG. 1A and FIG. 1B, again).

Furthermore, a forward loop primer (FLP) 109 may be designed between F1 region and F2 region, and a backward loop primer (BLP) 111 may be designed between B1c region and B2c region to raise the efficiency of the loop-mediated isothermal amplification (please refer to FIG. 1C).

Therefore, the primer set for detecting GAPDH nucleic acids in the GAPDH nucleic acid detection kit of the present disclosure mentioned above at least may comprise a forward inner primer for GAPDH nucleic acids, a forward outer primer for GAPDH nucleic acids, a backward inner primer for GAPDH nucleic acids and a backward outer primer for GAPDH nucleic acids, but it is not limited thereto.

A sequence of GAPDH nucleic acids for designing the primer set mentioned above may be the nucleotide sequence of SEQ ID NO. 1, which is a part of the mRNA sequence of GAPDH (NCBI accession number NM_001256799), but it is not limited thereto.

The forward inner primer for GAPDH nucleic acids mentioned above may consist of a first segment and a second segment, and the 3' end of the first segment mentioned above is connected to the 5' end of the second segment mentioned above, or the forward inner primer for GAPDH nucleic acids mentioned above may consist of a first segment, a first linker and a second segment, and the 3' end of the first segment mentioned above is connected to the 5' end of the first linker mentioned above, and the 3' end of the first linker mentioned above is connected to the 5' end of the second segment mentioned above. The first segment mentioned above may have about 10-30 nucleotides, and may consist of a complementary strand of a first sequence section, and the first sequence section mentioned above may be located between position 134 and position 175 of the nucleotide sequence of SEQ ID NO. 1, but it is not limited thereto. The second segment mentioned above may have about 10-30 nucleotides, and may consist of a second sequence section, and the second sequence section mentioned above may be located between position 77 and position 115 of the nucleotide sequence of SEQ ID NO. 1, but it is also not limited thereto. The first linker mentioned above may comprise about 1-6 thymines or peptide nucleic acids, but it is not limited thereto.

The forward outer primer for GAPDH nucleic acids mentioned above may have about 10-30 nucleotides and may consist of a third sequence section, and the third sequence section mentioned above may be located between position 42 and position 79 of the nucleotide sequence of SEQ ID NO. 1, but it is not limited thereto.

The backward inner primer for GAPDH nucleic acids mentioned above may consist of a third segment and a fourth segment, and the 3' end of the third segment mentioned above is connected to the 5' end of the fourth segment mentioned above, or the backward inner primer for GAPDH nucleic acids mentioned above may consist of a third segment, a second linker and a fourth segment, and the 3' end of the third segment mentioned above is connected to the 5' end of the second linker mentioned above, and the 3' end of the second linker mentioned above is connected to the 5' end of the fourth segment mentioned above. The third segment mentioned above may have about 10-30 nucleotides and may consist of a fourth sequence section, and the fourth sequence section mentioned above may be located between position 156 and position 207 of the nucleotide sequence of SEQ ID NO. 1, but it is not limited thereto. The fourth segment mentioned above may have about 10-30 nucleotides and may consist of a complementary strand of a fifth sequence section, and the fifth sequence section mentioned above may be located between position 211 and position 250 of the nucleotide sequence of SEQ ID NO. 1, but it is also not limited thereto. Moreover, the second linker mentioned above may comprise about 1-6 thymines or peptide nucleic acids, but it is not limited thereto.

The backward outer primer for GAPDH nucleic acids mentioned above may have about 10-30 nucleotides and may consist of a complementary strand of a sixth sequence section, and the sixth sequence section mentioned above may be located between position 238 and position 275 of the nucleotide sequence of SEQ ID NO. 1, but it is not limited thereto.

In one embodiment, in the primer set for detecting GAPDH nucleic acids in the GAPDH nucleic acid detection kit of the present disclosure mentioned above, the first sequence section mentioned above may be located between position 139 and position 170 of the nucleotide sequence of SEQ ID NO. 1, the second sequence section mentioned above may be located between position 82 and position 110 of the nucleotide sequence of SEQ ID NO. 1, the third sequence section mentioned above may be located between position 47 and position 74 of the nucleotide sequence of SEQ ID NO. 1, the fourth sequence section mentioned above may be located between position 161 and position 202 of the nucleotide sequence of SEQ ID NO. 1, the fifth sequence section mentioned above may be located between position 216 and position 245 of the nucleotide sequence of SEQ ID NO. 1, and the sixth sequence section mentioned above may be located between position 243 and position 270 of the nucleotide sequence of SEQ ID NO. 1.

Moreover, in one specific embodiment, in the primer set for detecting GAPDH nucleic acids in the GAPDH nucleic acid detection kit of the present disclosure mentioned above, the sequence of the forward inner primer for GAPDH nucleic acids mentioned above may comprise the nucleotide sequence of SEQ ID NO. 2, the sequence of the forward outer primer for GAPDH nucleic acids mentioned above may comprise the nucleotide sequence of SEQ ID NO. 3, the sequence of the backward inner primer for GAPDH nucleic acids mentioned above may comprise the nucleotide sequence of SEQ ID NO. 4, the nucleotide sequence of SEQ ID NO. 6 or the nucleotide sequence of SEQ ID NO. 7, and the sequence of the backward outer primer for GAPDH nucleic acids mentioned above may comprise the nucleotide sequence of SEQ ID NO. 5.

In another embodiment, in the primer set for detecting GAPDH nucleic acids in the GAPDH nucleic acid detection kit of the present disclosure mentioned above, for at least one of the forward inner primer for GAPDH nucleic acids mentioned above, the forward outer primer for GAPDH nucleic acids mentioned above, the backward inner primer for GAPDH nucleic acids mentioned above and the backward outer primer for GAPDH nucleic acids mentioned above, 1 to 10 nucleotides counted from any one position as a start point between position 4 and position 14 from the 3' end thereof may be independently substituted by inosine (I), guanine (G), uracil (U), etc., but it is not limited thereto. For example, in one embodiment, in the primer set for detecting GAPDH nucleic acids in the GAPDH nucleic acid detection kit of the present disclosure mentioned above, at least one of the forward inner primer for GAPDH nucleic acids mentioned above, the forward outer primer for GAPDH nucleic acids mentioned above, the backward inner primer for GAPDH nucleic acids mentioned above and the backward outer primer for GAPDH nucleic acids mentioned above may comprise, but are not limited to several substitution statuses as shown below: 2 to 7 nucleotides counted from any one position as a start point between position 5 and position 9 from the 3' end thereof may be independently substituted by inosine, guanin, uracil, etc., 3 to 5 nucleotides counted from position 7 from the 3' end thereof as a start point may be independently substituted by inosine, or 3 to 5 nucleotides counted from position 9 from the 3' end thereof as a start point may be independently substituted by inosine. For example, in the primer set for detecting GAPDH nucleic acids in the GAPDH nucleic acid detection kit of the present disclosure mentioned above, the sequence of the backward inner primer for GAPDH nucleic acids mentioned above may comprise the nucleotide sequence of SEQ ID NO. 8, or for example, in the primer set for detecting GAPDH nucleic acids in the GAPDH nucleic acid detection kit of the present disclosure mentioned above, the sequence of the backward outer primer for GAPDH nucleic acids mentioned above may comprise the nucleotide sequence of SEQ ID NO. 9. Furthermore, in one specific embodiment, in the primer set for detecting GAPDH nucleic acids in the GAPDH nucleic acid detection kit of the present disclosure mentioned above, the sequence of the forward inner primer for GAPDH nucleic acids mentioned above may comprise the nucleotide sequence of SEQ ID NO. 2, the sequence of the forward outer primer for GAPDH nucleic acids mentioned above may comprise the nucleotide sequence of SEQ ID NO. 3, the sequence of the backward inner primer for GAPDH nucleic acids mentioned above may comprise the nucleotide sequence of SEQ ID NO. 4, and the sequence of the backward outer primer for GAPDH nucleic acids mentioned above may comprise the nucleotide sequence of SEQ ID NO. 9. In addition, in another specific embodiment, in the primer set for detecting GAPDH nucleic acids in the GAPDH nucleic acid detection kit of the present disclosure mentioned above, the sequence of the forward inner primer for GAPDH nucleic acids mentioned above may comprise the nucleotide sequence of SEQ ID NO. 2, the sequence of the forward outer primer for GAPDH nucleic acids mentioned above may comprise the nucleotide sequence of SEQ ID NO. 3, the sequence of the backward inner primer for GAPDH nucleic acids mentioned above may comprise the nucleotide sequence of SEQ ID NO. 8, and the sequence of the backward outer primer for GAPDH nucleic acids mentioned above may comprise the nucleotide sequence of SEQ ID NO. 9.

Figure 2A:
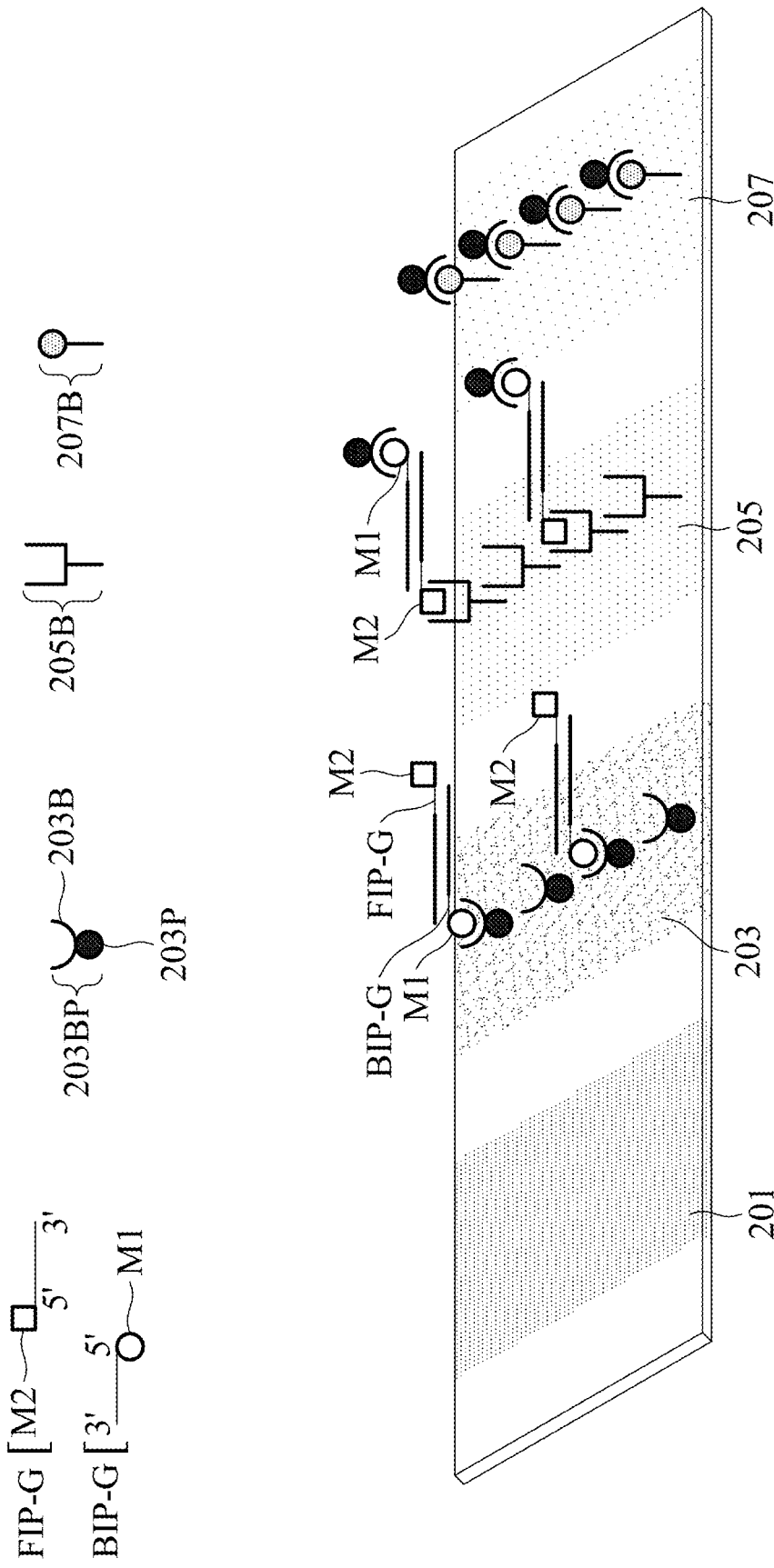
FIG. 2A shows a schematic diagram of an action mechanism of a lateral flow immunoassay test strip in one embodiment of the present disclosure.

Please refer to FIG. 2A which is a schematic diagram of an action mechanisms of a lateral flow immunoassay test strips in one embodiment of the present disclosure. The size, quantity, shape and/or structure, etc. of each element shown in FIG. 2A are for schema and easy illustration only and are not intended to represent the actual size, quantity, shape and/or structure, etc. of each element. In one embodiment, in the primer set for detecting GAPDH nucleic acids in the GAPDH nucleic acid detection kit of the present disclosure mentioned above, the 5' end of the backward inner primer for GAPDH nucleic acids BIP-G mentioned above may be labeled with a first label M1, and the 5' end of the forward inner primer for GAPDH nucleic acids FIP-G mentioned above may be labeled with a second label M2, wherein the foregoing first label M1 and the foregoing second label M2 mentioned above are different. The foregoing first label M1 may comprise biotin, avidin, streptavidin (SA), digoxigenin (DIG), fluorescein (FAM), etc., but it is not limited thereto. The foregoing second label M2 may also comprise, but is not limited to biotin, avidin, streptavidin, digoxigenin, fluorescein, etc. Furthermore, in this embodiment, the GAPDH nucleic acid detection kit of the present disclosure, in addition to the primer set for detecting GAPDH nucleic acids mentioned above, may further comprises a lateral flow immunoassay test strip 200, but it is not limited thereto. The material of the lateral flow immunoassay test strip 200 may comprise, but is not limited to nitrocellulose membrane, nylon membrane, polyvinylidene fluoride (PVDF) membrane, polyethersulfone (PES) membrane, etc.

Please refer to FIG. 2A, again. The lateral flow immunoassay test strip 200 mentioned above, according to a flow direction of an analyte, may sequentially comprise an analyte addition area 201, a binding area 203, a GAPDH detection area 205 and a test strip control area 207. The binding area 203 mentioned above has a first binding particle 203BP which has a first binding molecule 203B and a particle 203P linked to the first binding molecule 203B mentioned above, wherein the first binding molecule 203B mentioned above is capable of binding to the first label M1 mentioned above. The material of the particle 203P mentioned above may comprise, but is not limited to gold, carbon, latex, magnetic substances, etc. Alternatively, the binding area 203 mentioned above, in addition to the first binding particle 203BP mentioned above, may further comprise a control particle CP (no shown) coated with a specific substance. Example of material of the control particle CP may refer to the material of the particle 203P mentioned above, however, on the lateral flow immunoassay test strip 200, the materials of both of the control particle CP and the particle 203P may be the same or different. Moreover, the foregoing specific substance has no particular limitation, as long as there is a molecule capable of binding thereto, and example of the foregoing specific substance may comprise, but is not limited to serum (such as mouse serum, but it is not limited thereto). The GAPDH detection area 205 mentioned above is immobilized with a second binding molecule 205B which is capable of binding to the second label M2 mentioned above. Moreover, the test strip control area 207 mentioned above is immobilized with a third binding molecule 207B which is capable of binding to the first binding molecule 203B mentioned above of the first binding particle 203BP mentioned above, wherein the third binding molecule 207B mentioned above and the first label M1 mentioned above may be the same or different. Alternatively, under a condition of that the binding area 203 mentioned above in addition to the first binding particle 203BP, may further comprise a control particle CP (no shown), the third binding molecule 207B immobilized on the third the test strip control area 207 mentioned above may be capable of binding to the foregoing specific substance of the foregoing control particle CP. For example, when the specific substance coated on the control particle CP is mouse serum, the third binding molecule 207B may be an anti-mouse serum antibody.

The reaction of the lateral flow immunoassay test strip 200 shown in the schematic diagram of FIG. 2A is described below for each area during operation. Please refer to FIG. 2A. When a sample to be tested contains GAPDH nucleic acids, a reaction solution containing a GAPDH nucleic acid amplification product can be obtained by a loop-mediated isothermal amplification using the primer set for detecting GAPDH nucleic acids in the GAPDH nucleic acid detection kit of the present disclosure mentioned above, and the GAPDH nucleic acid amplification product has the first label M1 and the second label M2. After the foregoing reaction solution is added to the analyte addition area 201 of the lateral flow immunoassay test strip 200 mentioned above, the foregoing reaction solution moves to the binding area 203 mentioned above, and thus the first labels M1 of the GAPDH nucleic acid amplification product will bind to the first binding molecules 203B of part of the first binding particles 203BP on the binding area 203 mentioned above, and moves together with the remaining first binding particles 203BP which do not bind to any amplification product to the GAPDH detection area 205 mentioned above. In the GAPDH detection area 205 mentioned above, the second label M2 of the GAPDH nucleic acid amplification product that has been bound to the first binding molecule 203B of the first binding particle 203BP will bind to the second binding molecules 205B immobilized on the GAPDH detection area 205 mentioned above to allow the GAPDH nucleic acid amplification product stay on the GAPDH detection area 205 mentioned above and present the color of the first binding particles 203BP while the remaining first binding particles 203BP which do not bind to any amplification product will continue to move to the test strip control area 207 mentioned above. In the test strip control area 207 mentioned above, the first binding molecules 203B of the remaining first binding particles 203BP which do not bind to any amplification product will bind to the third binding molecules 207B immobilized on the test strip control area 207 mentioned above to allow the remaining first binding particles 203BP which do not bind to any amplification product to stay on the test strip control area 207 and present the color of the first binding particles 203BP. In contrast, when a sample to be tested does not contain GAPDH nucleic acids, a reaction solution without GAPDH nucleic acid amplification product will be obtained by a loop-mediated isothermal amplification using the primer set for detecting GAPDH nucleic acids in the GAPDH nucleic acid detection kit of the present disclosure mentioned above. After the foregoing reaction solution is added to the analyte addition area 201 of the lateral flow immunoassay test strip 200 mentioned above, the foregoing reaction solution moves to the binding area 203 mentioned above, however, since no GAPDH nucleic acid amplification product is present in the reaction solution, the first binding particle 203BP on the binding area 203 mentioned above will not bind to any amplification product (an amplification product bearing with first label M1 and second label M2 at the same time), and will move to the GAPDH detection area 205 mentioned above. Similarly, since the first binding particle 203BP does not bind to any amplification product (an amplification product bearing with first label M1 and second label M2 at the same time), it will not bind to the second binding molecule 205B immobilized on the GAPDH detection area 205 mentioned above and stay on the GAPDH detection area 205 mentioned above and present its color. After that, the first binding particle 203BP continues to move to the test strip control area 207 mentioned above. In the test strip control area 207 mentioned above, the first binding molecule 203B of the first binding particle 203BP will bind to the third binding molecules 207B immobilized on the test strip control area 207 mentioned above to allow the first binding particle 203BP to stay on the test strip control area 207 and present the color of the first binding particles 203BP.

In one specific embodiment, in the primer set for detecting GAPDH nucleic acids in the GAPDH nucleic acid detection kit of the present disclosure mentioned above, the 5' end of the backward inner primer for GAPDH nucleic acids BIP-G mentioned above is labeled with biotin and the 5' end of the forward inner primer for GAPDH nucleic acids FIP-G mentioned above is labeled with digoxigenin. Moreover, in this specific embodiment, the GAPDH nucleic acid detection kit of the present disclosure, in addition to the primer set for detecting GAPDH nucleic acids mentioned above, further comprises the lateral flow immunoassay test strip 200 mentioned above, and in the lateral flow immunoassay test strip 200, the binding area 203 mentioned above has the first binding particle 203BP and first binding molecule 203B of the first binding particle is avidin, the second binding molecule 205B of the GAPDH detection area 205 mentioned above is an antibody that can recognize digoxigenin, and the third binding molecule 207B in the test strip control area 207 mentioned above may be biotin or an antibody that can recognize avidin.

Furthermore, in one embodiment, the GAPDH nucleic acid detection kit of the present disclosure, in addition to the primer set for detecting GAPDH nucleic acids mentioned above may further comprise a polymerase and/or nucleotide substrate, but it is not limited thereto. The polymerase mentioned above may have a function of reverse transcriptase, but it is also not limited thereto. In one specific embodiment, the polymerase mentioned above is a Bst DNA polymerase, such as a Bst DNA polymerase the amino acid sequence of which comprises the amino acid sequence of SEQ ID NO. 10, but it is not limited thereto.

Moreover, in one embodiment, the GAPDH nucleic acid detection kit of the present disclosure, in add-on to the primer set for detecting GAPDH nucleic acids mentioned above, may further comprise a reverse transcriptase and/or nucleotide substrate, but it is not limited thereto. The reverse transcriptase mentioned above may have a function of a ribonuclease (RNase), but it is also not limited thereto. In one specific embodiment, the reverse transcriptase mentioned above may have a function of ribonuclease H (RNase H).

The present disclosure may further provide a target nucleic acid detection kit which may comprise, but is not limited to a primer set for detecting GAPDH nucleic acids and a primer set for detecting target nucleic acids, wherein a detection target of the primer set for detecting target nucleic acids mentioned above differs from a detection target of the primer set for detecting GAPDH nucleic acids mentioned above.

The primer set for detecting GAPDH nucleic acids and the primer set for detecting target nucleic acids in the target nucleic acid detection kit of the present disclosure mentioned above may be respectively used in a first loop-mediated isothermal amplification and a second loop-mediated isothermal amplification to determine whether target nucleic acids are present in a sample to be tested or not.

The first loop-mediated isothermal amplification and a second loop-mediated isothermal amplification mentioned above may comprise a standard loop-mediated isothermal amplification, a reverse transcription loop-mediated isothermal amplification, etc., but it is not limited thereto.

The sample to be tested mentioned above may be a sample not subjected to any purification process, for example, subjected to no nucleic acid purification process. Namely, by the primer set for detecting GAPDH nucleic acids and the primer set for detecting target nucleic acids in the target nucleic acid detection kit of the present disclosure mentioned above, nucleic acid amplifications can be performed on a biosample not subjected to any purification process to obtain an accurate target nucleic acid detection result to achieve an effect of reducing or eliminating processing a sample to be tested.

A source of the foregoing sample to be tested may comprise, but is not limited to a saliva specimen, a sputum specimen, a nose swab specimen, a throat swab specimen, a nasopharyngeal specimen, a urine specimen, a stool specimen, a rectal swab specimen, a cerebrospinal fluid (CSF) specimen, a body fluid specimen, etc.

In one embodiment, a source of the sample to be tested mentioned above may be a specimen obtained from a non-invasive sampling, such as a saliva specimen, a sputum specimen, a urine specimen and a stool specimen, but it is not limited thereto. In this embodiment, the target nucleic acid detection kit of the present disclosure may collocate with an isothermal reaction machine and a simple assay test strip, such as a lateral flow immunoassay test strip, to achieve a purpose of home testing.

Furthermore, the primer set for detecting GAPDH nucleic acids and the primer set for detecting target nucleic acids in the target nucleic acid detection kit of the present disclosure mentioned above both may use a single-stranded RNA or first strand cDNA as an initial template to respectively perform the first loop-mediated isothermal amplification and the second loop-mediated isothermal amplification mentioned above, but it is not limited thereto.

Design of the primer set for detecting GAPDH nucleic acids and the primer set for detecting target nucleic acids in the target nucleic acid detection kit of the present disclosure is also based on an loop-mediated isothermal amplification, however, the designed primer set is not only suitable for the loop-mediated isothermal amplification. Design and operation principle for the primer set for detecting GAPDH nucleic acids and the primer set for detecting target nucleic acids in the target nucleic acid detection kit of the present disclosure mentioned above are also shown in FIG. 1A, FIG. 1B and FIG. 1C. For the detailed descriptions for the design and operation principle of the primer set for detecting GAPDH nucleic acid and the primer set for detecting target nucleic acid in the target nucleic acid detection kit of the present disclosure, please refer the descriptions regarding to the design and operation principle of the primer set for detecting GAPDH nucleic acid in the GAPDH nucleic acid detection kit of the present disclosure in the previous paragraphs, and thus they will not be repeated herein.

Accordingly, the primer set for detecting GAPDH nucleic acids in the target nucleic acid detection kit of the present disclosure may be any primer set for detecting GAPDH nucleic acids in the GAPDH nucleic acid detection kit of the present disclosure mentioned above, and the primer set for detecting target nucleic acids in the target nucleic acid detection kit of the present disclosure mentioned above may comprise a forward inner primer for target nucleic acids, a forward outer primer for target nucleic acids, a backward inner primer for target nucleic acids and a backward outer primer for target nucleic acids, but it is not limited thereto.

A detection target of the primer set for detecting target nucleic acids in the target nucleic acid detection kit of the present disclosure has no particular limitation, as long as it is different from a detection target of the primer set for detecting GAPDH nucleic acids in the target nucleic acid detection set of the present disclosure.

In one embodiment, the detection target of the primer set for detecting target nucleic acids in the target nucleic acid detection kit of the present disclosure may be nucleic acids of an RNA virus. Example of the RNA virus may comprise a coronavirus, an influenza virus, a human immunodeficiency virus (HIV), Ebola virus, hepatitis C virus (HCV), but it is not limited thereto.

The coronavirus mentioned above may comprise, but is not limited to severe acute respiratory syndrome coronavirus (SARS-CoV), severe acute respiratory syndrome coronavirus 2 (SARS-CoV-2 or 2019-nCoV), Middle East respiratory syndrome coronavirus (MERS-CoV), etc.

In addition, nucleic acids of the severe acute respiratory syndrome coronavirus type 2 (SARS-CoV-2 or 2019-nCoV) mentioned above may comprise, but is not limited to nucleic acids within the range of ORF1ab (e.g., nucleic acids of the RdRp gene, but it is not limited thereto), nucleic acids of spike protein (S) gene, nucleic acids of envelope (E) gene, nucleic acids of membrane protein (M) gene, nucleic acids of nucleoprotein (N) gene, etc.

In one embodiment, the detection target of the primer set for detecting target nucleic acids in the target nucleic acid detection kit of the present disclosure may be nucleic acids of the RdRp gene of severe acute respiratory syndrome coronavirus type 2 (SARS-CoV-2 or 2019-nCoV).

In the embodiment in which the detection target of the primer set for detecting target nucleic acids in the target nucleic acid detection kit of the present disclosure may be nucleic acids of the RdRp gene of severe acute respiratory syndrome coronavirus type 2 (SARS-CoV-2 or 2019-nCoV), the sequence of the nucleic acids of RdRp gene used to design the primer set mentioned above may be the sequence of SEQ ID NO.11 which is part of the nucleic acid sequence of ORF1ab of severe acute respiratory syndrome coronavirus type 2 (NCBI Accession Number MN908947), but it is not limited thereto.

In the embodiment in which the detection target of the primer set for detecting target nucleic acids in the target nucleic acid detection kit of the present disclosure may be nucleic acids of the RdRp gene of severe acute respiratory syndrome coronavirus type 2 (SARS-CoV-2 or 2019-nCoV), the forward inner primer for target nucleic acids mentioned above may consist of a fifth segment and a sixth segment, and 3' end of the fifth segment mentioned above the is connected to the 5' end of the sixth segment mentioned above, or the forward inner primer for target nucleic acids mentioned above consists of a fifth segment, a third linker and a sixth segment, and the 3' end of the fifth segment mentioned above is connected to the 5' end of the third linker mentioned above, and the 3' end of the third linker mentioned above is connected to the 5' end of the sixth segment mentioned above. The fifth segment mentioned above may have about 10-30 nucleotides and may consist of a complementary strand of a seventh sequence section, and the seventh sequence section mentioned above may be located between position 90 and position 134 of the nucleotide sequence of SEQ ID NO. 11, but it is not limited thereto. The sixth segment mentioned above may have about 10-30 nucleotides and may consist of an eighth sequence section, and the eighth sequence section mentioned above may be located between position 45 and position 82 of the nucleotide sequence of SEQ ID NO. 11, but it is also not limited thereto. The third linker mentioned above may comprise about 1-6 thymines or peptide nucleic acids, but it is not limited thereto.

Moreover, the forward outer primer for target nucleic acids mentioned above may have about 10-30 nucleotides and may consist of a ninth sequence section, and the ninth sequence section mentioned above may be located between position 27 and position 64 of the nucleotide sequence of SEQ ID NO. 11, but it is not limited thereto.

The backward inner primer for target nucleic acids mentioned above may consist of a seventh segment and an eighth segment, and the 3' end the seventh segment mentioned above of is connected to the 5' end of the eighth segment mentioned above, or the backward inner primer for target nucleic acids mentioned above consists of a seventh segment, a fourth linker and an eighth segment, and the 3' end of the seventh segment mentioned above is connected to the 5' end of the fourth linker mentioned above, and the 3' end of the fourth linker mentioned above is connected to the 5' end of the eighth segment mentioned above. The seventh segment mentioned above may have about 10-30 nucleotides and may consist of a tenth sequence section, and the tenth sequence section mentioned above may be located between position 123 and position 165 of the nucleotide sequence of SEQ ID NO. 11, but it is not limited thereto. The eighth segment mentioned above may have about 10-30 nucleotides and may consist of a complementary strand of an eleventh sequence section, and the eleventh sequence section mentioned above may be located between position 170 and position 208 of the nucleotide sequence of SEQ ID NO. 11, but it is also not limited thereto. The fourth linker mentioned above may comprise about 1-6 thymines or peptide nucleic acids, but it is not limited thereto.

The backward outer primer for target nucleic acids mentioned above may have about 10-30 nucleotides and may consist of a complementary strand of a twelfth sequence section, and the twelfth sequence section mentioned above may be located between position 226 and position 263 of the nucleotide sequence of SEQ ID NO. 11, but it is not limited thereto.

In the embodiment in which the detection target of the primer set for detecting target nucleic acids in the target nucleic acid detection kit of the present disclosure may be nucleic acids of the RdRp gene of severe acute respiratory syndrome coronavirus type 2 (SARS-CoV-2 or 2019-nCoV), in one specific embodiment, in the target nucleic acid detection kit of the present disclosure mentioned above, the seventh sequence section mentioned above may be located between position 95 and position 129 of the nucleotide sequence of SEQ ID NO. 11, the eighth sequence section mentioned above may be located between position 50 and position 77 of the nucleotide sequence of SEQ ID NO. 11, the ninth sequence section mentioned above may be located between position 32 and position 59 of the nucleotide sequence of SEQ ID NO. 11, the tenth sequence section mentioned above may be located between position 128 and position 150 of the nucleotide sequence of SEQ ID NO. 11, the eleventh mentioned above sequence section may be located between position 175 and position 203 of the nucleotide sequence of SEQ ID NO. 11, and the twelfth sequence section mentioned above may be located between position 231 and position 258 of the nucleotide sequence of SEQ ID NO. 11.

Alternatively, in the embodiment in which the detection target of the primer set for detecting target nucleic acids in the target nucleic acid detection kit of the present disclosure may be nucleic acids of the RdRp gene of severe acute respiratory syndrome coronavirus type 2 (SARS-CoV-2 or 2019-nCoV), for one specific embodiment, in the target nucleic acid detection kit of the present disclosure mentioned above, the sequence of the forward inner primer for target nucleic acids mentioned above may comprise the nucleotide sequence of SEQ ID NO. 12, the sequence of the forward outer primer for target nucleic acids mentioned above may comprise the nucleotide sequence of SEQ ID NO. 13, the sequence of the backward inner primer for target nucleic acids mentioned above may comprise the nucleotide sequence of SEQ ID NO. 14, and the sequence of the backward outer primer for target nucleic acids mentioned above may comprise the nucleotide sequence of SEQ ID NO. 15.

In the embodiment in which the detection target of the primer set for detecting target nucleic acids in the target nucleic acid detection kit of the present disclosure may be nucleic acids of the RdRp gene of severe acute respiratory syndrome coronavirus type 2 (SARS-CoV-2 or 2019-nCoV), for one specific embodiment, the primer set for detecting target nucleic acids mentioned above may further comprise a forward loop primer for target nucleic acids and a backward loop primer for target nucleic acids, but it is not limited thereto.

The forward loop primer for target nucleic acids mentioned above may have about 10-30 nucleotides and may consist of a thirteenth sequence section, and the thirteenth sequence section mentioned above may be located between position 63 and position 104 of the nucleotide sequence of SEQ ID NO. 11. The backward loop primer for target nucleic acids mentioned above may have about 10-30 nucleotides and may consist of a fourteenth sequence section, and the fourteenth sequence section mentioned above may be located between position 146 and position 187 of the nucleotide sequence of SEQ ID NO. 11. Alternatively, the thirteenth sequence section mentioned above may be located between position 68 and position 99 of the nucleotide sequence of SEQ ID NO. 11, and the fourteenth sequence section mentioned above may be located between position 151 and position 182 of the nucleotide sequence of SEQ ID NO. 11.

Alternatively, in the specific embodiment mentioned above, in the primer set for detecting target nucleic acids in the target nucleic acid detection kit of the present disclosure, the sequence of the forward inner primer for target nucleic acids mentioned above may comprise the nucleotide sequence of SEQ ID NO. 12, the sequence of the forward outer primer for target nucleic acids mentioned above may comprise the nucleotide sequence of SEQ ID NO. 13, the sequence of the forward loop primer for target nucleic acids mentioned above may comprise the nucleotide sequence of SEQ ID NO. 16, the sequence of the backward inner primer for target nucleic acids mentioned above may comprise the nucleotide sequence of SEQ ID NO. 14, the sequence of the backward outer primer for target nucleic acids mentioned above may comprise the nucleotide sequence of SEQ ID NO. 15, and the sequence of the backward loop primer for target nucleic acids mentioned above may comprise the nucleotide sequence of SEQ ID NO. 17.

In another embodiment, in the primer set for detecting target nucleic acids in the target nucleic acid detection kit of the present disclosure, for at least one of the forward inner primer for target nucleic acids mentioned above, the forward outer primer for target nucleic acids mentioned above, the backward inner primer for target nucleic acids mentioned above and the backward outer primer for target nucleic acids mentioned above, 1 to 10 nucleotides counted from any one position as a start point between position 4 and position 14 from the 3' end thereof may be independently substituted by inosine (I), guanine (G), uracil (U), etc., but it is not limited thereto. For example, in one embodiment, in the primer set for detecting target nucleic acids in the target nucleic acid detection kit of the present disclosure mentioned above, at least one of the forward inner primer for target nucleic acids mentioned above, the forward outer primer for target nucleic acids mentioned above, the backward inner primer for target nucleic acids mentioned above and the backward outer primer for target nucleic acids mentioned above may comprise, but are not limited to several substitution statuses as shown below: 2 to 7 nucleotides counted from any one position as a start point between position 5 and position 9 from the 3' end thereof may be independently substituted by inosine, guanin, uracil, etc., 3 to 5 nucleotides counted from position 7 from the 3' end thereof as a start point may be independently substituted by inosine, or 3 to 5 nucleotides counted from position 9 from the 3' end thereof as a start point may be independently substituted by inosine.

FIG. 2B and FIG. 2C are schematic diagrams of action mechanisms of lateral flow immunoassay test strips in different embodiments of the present disclosure. The size, quantity, shape and/or structure, etc. of each element shown in FIG. 2B and FIG. 2C are for schema and easy illustration only and are not intended to represent the actual size, quantity, shape and/or structure, etc. of each element.

In one embodiment, in the target nucleic acid detection kit of the present disclosure mentioned above, the 5' end of the backward inner primer for GAPDH nucleic acids mentioned above BIP-G and the 5' end of the backward inner primer for target nucleic acids mentioned above BIP-T may be labeled with a first label M1, the 5' end of the forward inner primer for GAPDH nucleic acids mentioned above FIP-G may be labeled with a second label M2, and the 5' end of the forward inner primer for target nucleic acids mentioned above FIP-T may be labeled with a third label M3, wherein the foregoing first label M1, the foregoing second label M2 and the foregoing third label M3 are different. The foregoing first label M1 may comprise biotin, avidin, streptavidin (SA), digoxigenin (DIG), fluorescein (FAM), etc., but it is not limited thereto. The foregoing second label M2 may also comprise, but is not limited to biotin, avidin, streptavidin, digoxigenin, fluorescein, etc. Similarly, the foregoing third label M3 may also comprise, but is not limited to biotin, avidin, streptavidin, digoxigenin, fluorescein, etc. Furthermore, in this embodiment, the target nucleic acid detection kit of the present disclosure, in addition to the primer set for detecting GAPDH nucleic acids mentioned above and the primer set for detecting target nucleic acids mentioned above, may further comprises a lateral flow immunoassay test strip 200' or 200", but it is not limited thereto. The material of the lateral flow immunoassay test strip 200' or 200" may comprise, but is not limited to nitrocellulose membrane, nylon membrane, polyvinylidene fluoride membrane, polyethersulfone membrane, etc.

Please refer to FIG. 2B and FIG. 2C, again. The lateral flow immunoassay test strip 200' or 200" mentioned above, according to a flow direction of an analyte, may sequentially comprise an analyte addition area 201, a binding area 203, a GAPDH detection area 205, a target nucleic acid detection area 206 and a test strip control area 207 (the lateral flow immunoassay test strip 200'), or may comprise an analyte addition area 201, a binding area 203, a target nucleic acid detection area 206, a GAPDH detection area 205, and a test strip control area 207 in order (the lateral flow immunoassay test strip 200"). The binding area 203 mentioned above has a first binding particle 203BP which has a first binding molecule 203B and a particle 203P linked to the first binding molecule 203B mentioned above, wherein the first binding molecule 203B mentioned above is capable of binding to the first label M1 mentioned above. The material of the particle 203P mentioned above may comprise, but is not limited to gold, carbon, latex, magnetic substances, etc. Alternatively, the binding area 203 mentioned above, in addition to the first binding particle 203BP mentioned above, may further comprise a control particle CP (no shown) coated with a specific substance. Example of material of the control particle CP may refer to the material of the particle 203P mentioned above, however, on the lateral flow immunoassay test strip 200' or 200", the materials of both of the control particle CP and the particle 203P may be the same or different. Moreover, the foregoing specific substance has no particular limitation, as long as there is a molecule capable of binding thereto, and example of the foregoing specific substance may comprise, but is not limited to serum (such as mouse serum, but it is not limited thereto). The GAPDH detection area 205 mentioned above is immobilized with a second binding molecule 205B which is capable of binding to the second label M2 mentioned above. Moreover, the test strip control area 207 mentioned above is immobilized with a third binding molecule 207B which is capable of binding to the first binding molecule 203B mentioned above of the first binding particle 203BP mentioned above, wherein the third binding molecule 207B mentioned above and the first label M1 mentioned above may be the same or different. Alternatively, under a condition of that the binding area 203 mentioned above in addition to the first binding particle 203BP, may further comprise a control particle CP (no shown), the third binding molecule 207B immobilized on the third the test strip control area 207 mentioned above may be capable of binding to the foregoing specific substance of the foregoing control particle CP. For example, when the specific substance coated on the control particle CP is mouse serum, the third binding molecule 207B may be an anti-mouse serum antibody. Furthermore, the target nucleic acid detection area 206 mentioned above is immobilized with a fourth binding molecule 206B which is capable of binding to the third label M3 mentioned above.

Figure 2B:
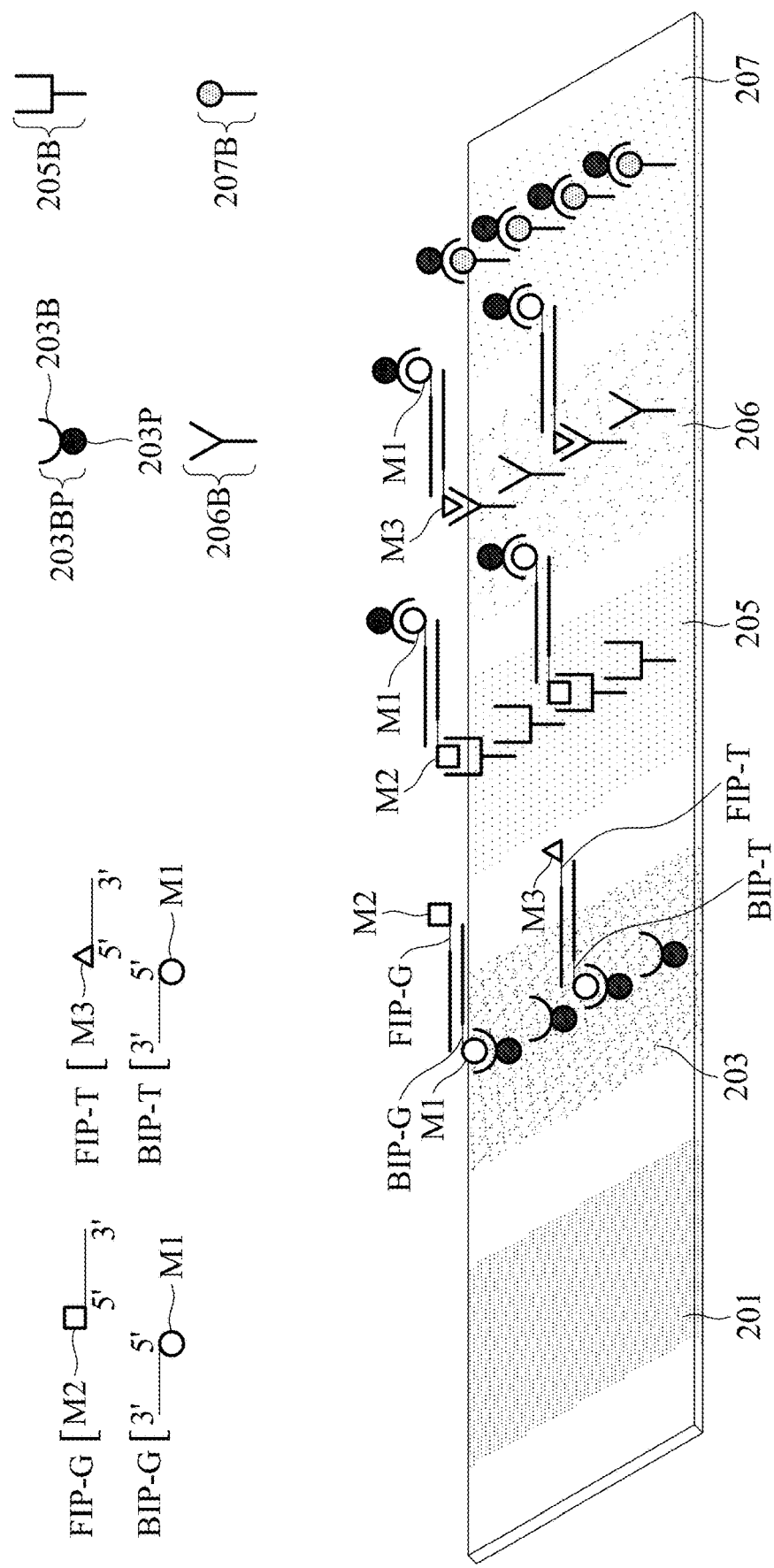
FIG. 2B shows a schematic diagram of an action mechanism of a lateral flow immunoassay test strip in another embodiment of the present disclosure.

The reaction of the lateral flow immunoassay test strip 200' shown in the schematic diagram of FIG. 2B is described below for each area during operation. Please refer to FIG. 2B. When a sample to be tested contains GAPDH nucleic acids and target nucleic acids, a first reaction solution containing a GAPDH nucleic acid amplification product and a second reaction solution containing a target nucleic acid amplification product can be respectively obtained by a first loop-mediated isothermal amplification using the primer set for detecting GAPDH nucleic acids in the target nucleic acid detection kit of the present disclosure mentioned above and a second loop-mediated isothermal amplification using the primer set for detecting target nucleic acids in the target nucleic acid detection kit of the present disclosure mentioned above, and the GAPDH nucleic acid amplification product has the first label M1 and the second label M2 while the target nucleic acid amplification product has the first label M1 and the third label M3. A mixture reaction solution is obtained by mixing the first reaction solution and the second reaction solution mentioned above. After the foregoing mixture reaction solution is added to the analyte addition area 201 of the lateral flow immunoassay test strip 200' mentioned above, the foregoing mixture reaction solution moves to the binding area 203 mentioned above, and thus the first labels M1 of the GAPDH nucleic acid amplification product and the first labels M1 of the target nucleic acid amplification product both will respectively bind to the first binding molecules 203B of part of the first binding particles 203BP on the binding area 203 mentioned above, and moves together with the remaining first binding particles 203BP which do not bind to any amplification product to the GAPDH detection area 205 mentioned above. In the GAPDH detection area 205 mentioned above, the second label M2 of the GAPDH nucleic acid amplification product that has been bound to the first binding molecule 203B of the first binding particle 203BP will bind to the second binding molecules 205B immobilized on the GAPDH detection area 205 mentioned above to allow the GAPDH nucleic acid amplification product stay on the GAPDH detection area 205 mentioned above and present the color of the first binding particles 203BP while the target nucleic acid amplification product that has been bound to the first binding molecule 203B of the first binding particle 203BP and the remaining first binding particles 203BP which do not bind to any amplification product will continue to move to the target nucleic acid detection area 206 mentioned above. In the target nucleic acid detection area 206 mentioned above, the third label M3 of the target nucleic acid amplification product that has been bound to the first binding molecule 203B of the first binding particle 203BP will bind to the fourth binding molecules 206B immobilized on the target nucleic acid detection area 206 mentioned above to allow the target nucleic acid amplification product stay on the target nucleic acid detection area 206 mentioned above and present the color of the first binding particles 203BP while the remaining first binding particles 203BP which do not bind to any amplification product will continue to move to the test strip control area 207 mentioned above. In the test strip control area 207 mentioned above, the first binding molecules 203B of the remaining first binding particles 203BP which do not bind to any amplification product will bind to the third binding molecules 207B immobilized on the test strip control area 207 mentioned above to allow the remaining first binding particles 203BP which do not bind to any amplification product to stay on the test strip control area 207 and present the color of the first binding particles 203BP. In contrast, when a sample to be tested contains GAPDH nucleic acids but does not contain target nucleic acids, a first reaction solution containing a GAPDH nucleic acid amplification product and a second reaction solution without target nucleic acid amplification product can be respectively obtained by a first loop-mediated isothermal amplification using the primer set for detecting GAPDH nucleic acids in the target nucleic acid detection kit of the present disclosure mentioned above and a second loop-mediated isothermal amplification using the primer set for detecting target nucleic acids in the target nucleic acid detection kit of the present disclosure mentioned above, and the GAPDH nucleic acid amplification product has the first label M1 and the second label M2. A mixture reaction solution is obtained by mixing the first reaction solution and the second reaction solution mentioned above. After the foregoing mixture reaction solution is added to the analyte addition area 201 of the lateral flow immunoassay test strip 200' mentioned above, the foregoing mixture reaction solution moves to the binding area 203 mentioned above, and thus the first labels M1 of the GAPDH nucleic acid amplification product will bind to the first binding molecules 203B of part of the first binding particles 203BP on the binding area 203 mentioned above, and moves together with the remaining first binding particles 203BP which do not bind to any amplification product to the GAPDH detection area 205 mentioned above. In the GAPDH detection area 205 mentioned above, the second label M2 of the GAPDH nucleic acid amplification product that has been bound to the first binding molecule 203B of the first binding particle 203BP will bind to the second binding molecules 205B immobilized on the GAPDH detection area 205 mentioned above to allow the GAPDH nucleic acid amplification product stay on the GAPDH detection area 205 mentioned above and present the color of the first binding particles 203BP while the remaining first binding particles 203BP which do not bind to any amplification product will continue to move to the target nucleic acid detection area 206 mentioned above. Since no target nucleic acid amplification product (an amplification product bearing with first label M1 and third label M3 at the same time) is present in the mixture reaction solution mentioned above, the remaining first binding particles 203BP which do not bind to any amplification product will bind to no target nucleic acid amplification product (an amplification product bearing with first label M1 and third label M3 at the same time) and will not bind to the fourth binding molecule 206B immobilized on the target nucleic acid detection area 206 mentioned above and stay on the target nucleic acid detection area 206 mentioned above and present its color. After that, the remaining first binding particle 203BP continues to move to the test strip control area 207 mentioned above. In the test strip control area 207 mentioned above, the first binding molecule 203B of the first binding particle 203BP will bind to the third binding molecules 207B immobilized on the test strip control area 207 mentioned above to allow the remaining first binding particle 203BP to stay on the test strip control area 207 and present the color of the first binding particles 203BP.

Figure 2C:
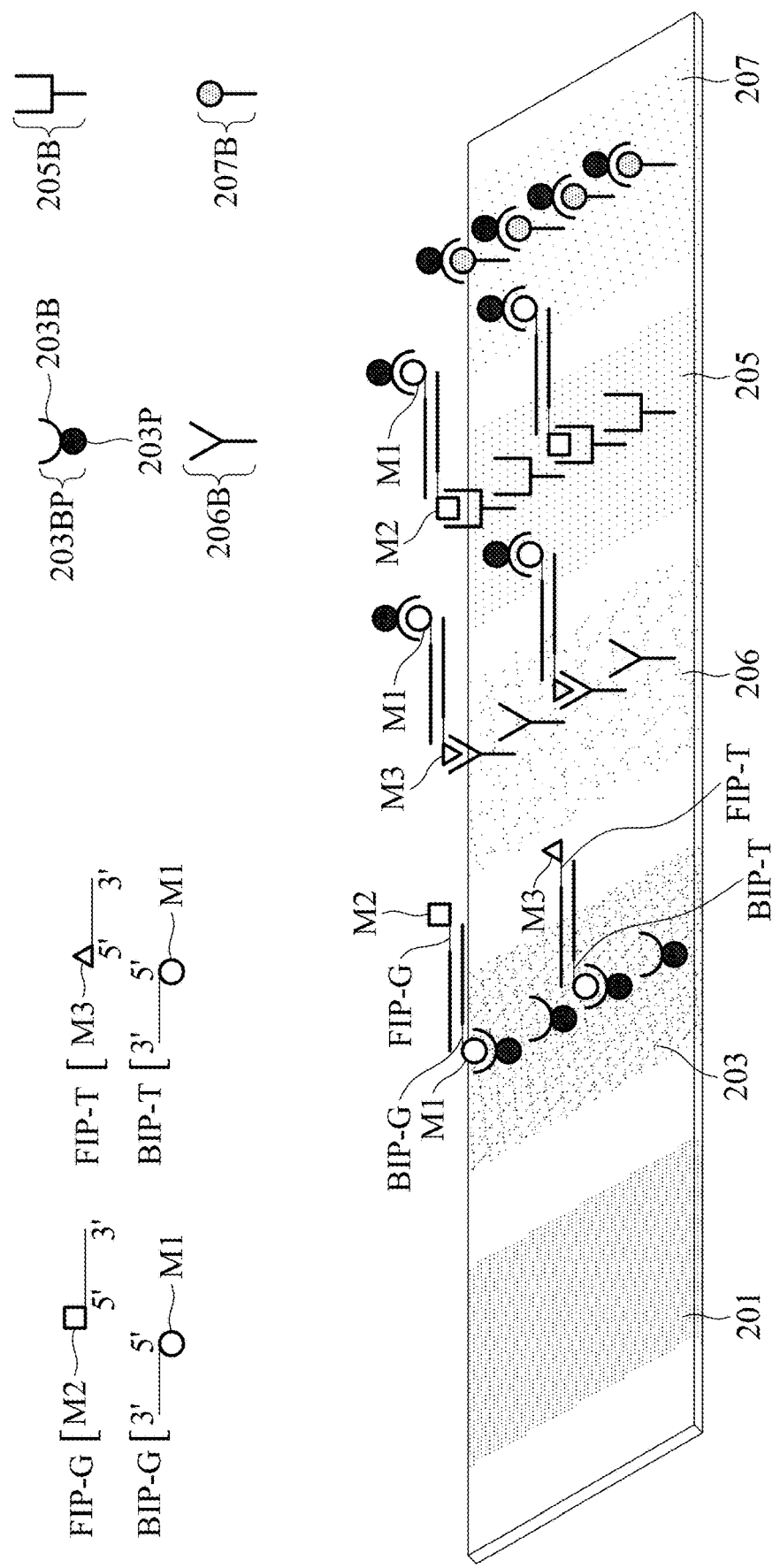
FIG. 2C shows a schematic diagram of an action mechanism of a lateral flow immunoassay test strip in yet another embodiment of the present disclosure.

The reaction principle of each area of the lateral flow immunoassay test strip 200" shown in the schematic diagram of FIG. 2C is similar to that of the lateral flow immunoassay test strip 200' shown in the schematic diagram of FIG. 2B, and thus it will not be repeated herein.

In one specific embodiment, in the primer set for detecting GAPDH nucleic acids and the primer set for detecting target nucleic acids in the target nucleic acid detection kit of the present disclosure mentioned above, the 5' end of the backward inner primer for GAPDH nucleic acids mentioned above BIP-G and the 5' end of the backward inner primer for target nucleic acids mentioned above BIP-T are labeled with biotin, the 5' end of the forward inner primer for GAPDH nucleic acids FIP-G mentioned above is labeled with digoxigenin and the 5' end of the forward inner primer for target nucleic acids FIP-T mentioned above is labeled with fluorescein. Moreover, in this specific embodiment, the target nucleic acid detection kit of the present disclosure, in addition to the primer set for detecting GAPDH nucleic acids mentioned above and the primer set for detecting target nucleic acids mentioned above, further comprises the lateral flow immunoassay test strip 200' or 200" mentioned above, and in the lateral flow immunoassay test strip 200' or 200", the binding area 203 mentioned above has the first binding particle 203BP and first binding molecule 203B of the first binding particle is avidin, the second binding molecule 205B of the GAPDH detection area 205 mentioned above is an antibody that can recognize digoxigenin, the fourth binding molecule 206B of the GAPDH detection area 206 mentioned above is an antibody that can recognize fluorescein, and the third binding molecule 207B in the test strip control area 207 mentioned above may be biotin or an antibody that can recognize avidin.

Furthermore, in one embodiment, the target nucleic acid detection kit of the present disclosure, in addition to the primer set for detecting GAPDH nucleic acids mentioned above and the primer set for detecting target nucleic acids mentioned above, may further comprise a polymerase and/or nucleotide substrate, but it is not limited thereto. The polymerase mentioned above may have a function of reverse transcriptase, but it is also not limited thereto. In one specific embodiment, the polymerase mentioned above is a Bst DNA polymerase, such as a Bst DNA polymerase the amino acid sequence of which comprises the amino acid sequence of SEQ ID NO. 10, but it is not limited thereto.

Moreover, in one embodiment, the target nucleic acid detection kit of the present disclosure, in addition to the primer set for detecting GAPDH nucleic acids mentioned above and the primer set for detecting target nucleic acids mentioned above, may further comprise a reverse transcriptase and/or nucleotide substrate, but it is not limited thereto. The reverse transcriptase mentioned above may have a function of a ribonuclease (RNase), but it is also not limited thereto. In one specific embodiment, the reverse transcriptase mentioned above may have a function of ribonuclease H (RNase H).

Based on the foregoing, the present disclosure may also provide a SARS-CoV-2 detection kit, which may comprise a primer set for detecting nucleic acids, but it is not limited thereto.

The primer set for detecting SARS-CoV-2 nucleic acid in the SARS-CoV-2 detection kit of the present disclosure may be any primer set for detecting target nucleic acids mentioned in all foregoing paragraphs regarding to the embodiment in which the detection target of the primer set for detecting target nucleic acids in the target nucleic acid detection kit of the present disclosure may be nucleic acids of the RdRp gene of severe acute respiratory syndrome coronavirus type 2 (SARS-CoV-2 or 2019-nCoV), but it is not limited thereto.

The primer set for detecting SARS-CoV-2 nucleic acids in the SARS-CoV-2 nucleic acid detection kit of the present disclosure mentioned above may be used in a loop-mediated isothermal amplification to determine whether SARS-CoV-2 nucleic acids are present in a sample to be tested or not.

The loop-mediated isothermal amplification mentioned above may comprise a standard loop-mediated isothermal amplification or a reverse transcription loop-mediated isothermal amplification, but it is not limited thereto.

The sample to be tested mentioned may be a sample without being subjected to any purification process, for example, without being subjected to a nucleic acid purification process. Namely, by the primer set for detecting SARS-CoV-2 nucleic acids in the SARS-CoV-2 nucleic acid detection kit of the present disclosure mentioned above, a nucleic acid amplification can be performed on a biosample without being subjected to any purification process to obtain an accurate SARS-CoV-2 nucleic acid detection result to achieve an effect of reducing or eliminating processing a sample to be tested.

A source of the foregoing sample to be tested may comprise, but is not limited to a saliva specimen, a sputum specimen, a nose swab specimen, a throat swab specimen, a nasopharyngeal specimen, a urine specimen, a stool specimen, a rectal swab specimen, a cerebrospinal fluid (CSF) specimen, a body fluid specimen, etc.

In one embodiment, a source of the sample to be tested mentioned above may be a specimen obtained from a non-invasive sampling, such as a saliva specimen, a sputum specimen, a urine specimen and a stool specimen, but it is not limited thereto. In this embodiment, the SARS-CoV-2 detection kit of the present disclosure may collocate with an isothermal reaction machine and a simple assay test strip, such as a lateral flow immunoassay test strip, to achieve home testing.

Moreover, the primer set for detecting SARS-CoV-2 nucleic acids in the SARS-CoV-2 detection kit of the present disclosure mentioned above may use a single-stranded RNA or first strand cDNA as an initial template to perform the loop-mediated isothermal amplification mentioned above, but it is not limited thereto.

In addition, in one embodiment, in the primer set for detecting SARS-CoV-2 nucleic acids in the SARS-CoV-2 detection kit of the present disclosure mentioned above, the 5' end of the backward inner primer for SARS-CoV-2 nucleic acids mentioned above may be labeled with a first label, and the 5' end of the forward inner primer for SARS-CoV-2 nucleic acids mentioned above may be labeled with a second label, wherein the foregoing first label and the foregoing second label mentioned above are different. The foregoing first label may comprise biotin, avidin, streptavidin (SA), digoxigenin (DIG), fluorescein (FAM), etc., but it is not limited thereto. The foregoing second label may also comprise, but is not limited to biotin, avidin, streptavidin, digoxigenin, fluorescein, etc.

Furthermore, in this embodiment, the SARS-CoV-2 detection kit of the present disclosure, in addition to the primer set for detecting SARS-CoV-2 nucleic acids mentioned above, may further comprises a lateral flow immunoassay test strip, but it is not limited thereto. The material of the lateral flow immunoassay test strip may comprise, but is not limited to nitrocellulose membrane, nylon membrane, polyvinylidene fluoride membrane, polyethersulfone membrane etc.

The lateral flow immunoassay test strip 200 mentioned above, based on an analyte flow direction, may sequentially comprise an analyte addition area, a binding area, a SARS-CoV-2 detection area and a test strip control area. The binding area mentioned above has a first binding particle which has a first binding molecule and a particle linked to the first binding molecule 203B mentioned above, in which the first binding molecule mentioned above is capable of binding to the first label M1 mentioned above. The material of the particle mentioned above may comprise, but is not limited to gold, carbon, latex, magnetic substances, etc. Alternatively, the binding area mentioned above, in addition to the first binding particle mentioned above, may further comprise a control particle coated with a specific substance. Example of material of the control particle may refer to the material of the particle mentioned above, however, on the lateral flow immunoassay test strip, the materials of both of the control particle and the particle may be the same or different. Moreover, the foregoing specific substance has no particular limitation, as long as there is a molecule capable of binding thereto, and example of the foregoing specific substance may comprise, but is not limited to serum (such as mouse serum, but it is not limited thereto). The SARS-CoV-2 detection area mentioned above is immobilized with a second binding molecule which is capable of binding to the second label mentioned above. Moreover, the test strip control area mentioned above is immobilized with a third binding molecule which is capable of binding to the first binding molecule mentioned above of the first binding particle mentioned above, wherein the third binding molecule mentioned above and the first label mentioned above may be the same or different. Alternatively, under a condition of that the binding area mentioned above in addition to the first binding particle, may further comprise a control particle, the third binding molecule immobilized on the third the test strip control area mentioned above may be capable of binding to the foregoing specific substance of the foregoing control particle. For example, when the specific substance coated on the control particle is mouse serum, the third binding molecule may be an anti-mouse serum antibody. In one specific embodiment, in the primer set for detecting SARS-CoV-2 nucleic acids in the SARS-CoV-2 detection kit of the present disclosure mentioned above, the 5' end of the backward inner primer for SARS-CoV-2 nucleic acids mentioned above is labeled with biotin and the 5' end of the forward inner primer for SARS-CoV-2 nucleic acids mentioned above is labeled with digoxigenin. Moreover, in this specific embodiment, the SARS-CoV-2 detection kit of the present disclosure, in addition to the primer set for detecting SARS-CoV-2 nucleic acids mentioned above, further comprises the lateral flow immunoassay test strip mentioned above, and in the lateral flow immunoassay test strip mentioned above, first binding molecule in the binding area is avidin, the second binding molecule in the SARS-CoV-2 detection area mentioned above is an antibody that can recognize digoxigenin, and the third binding molecule in the test strip control area mentioned above may be biotin or an antibody that can recognize avidin.

Moreover, in one embodiment, the SARS-CoV-2 detection kit of the present disclosure, in addition to the primer set for detecting SARS-CoV-2 nucleic acids mentioned above, may further comprise a polymerase and/or nucleotide substrate, but it is not limited thereto. The polymerase mentioned above may have a function of reverse transcriptase, but it is also not limited thereto. In one specific embodiment, the polymerase mentioned above is a Bst DNA polymerase, such as a Bst DNA polymerase the amino acid sequence of which comprises the amino acid sequence of SEQ ID NO. 10, but it is not limited thereto.

Furthermore, in one embodiment, the SARS-CoV-2 detection kit of the present disclosure, in addition to the primer set for detecting SARS-CoV-2 nucleic acids mentioned above, may further comprise a reverse transcriptase and/or nucleotide substrate, but it is not limited thereto. The reverse transcriptase mentioned above may have a function of a ribonuclease (RNase), but it is also not limited thereto. In one specific embodiment, the reverse transcriptase mentioned above may have a function of ribonuclease H (RNase H).

In addition, based on the foregoing, the present disclosure may also provide a method for detecting GAPDH nucleic acids. The method for detecting GAPDH nucleic acids of the present disclosure may comprise, but is not limited to the following steps.

First, a sample to be tested is provided. The relevant description for a source of the sample to be tested can be the same as the relevant description for the source of the sample to be tested mentioned in the foregoing paragraphs regarding to the GAPDH nucleic acid detection kit of the present disclosure, and thus it will be not repeated herein. In one embodiment, the source of the sample to be tested mentioned above may be a saliva specimen.

Next, a loop-mediated isothermal amplification is performed on the sample to be tested mentioned above by any foregoing primer set for detecting GAPDH nucleic acids in the GAPDH nucleic acid detection kit of the present disclosure. If the sample to be tested contains GAPDH nucleic acid, a GAPDH nucleic acid amplification product may be obtained from the loop-mediated isothermal amplification mentioned above.

Furthermore, in one embodiment, in the method for detecting GAPDH nucleic acid of the present disclosure, a determining manner for presence of the GAPDH nucleic acid amplification product has no particular limitation, as long as the presence of the GAPDH nucleic acid amplification product can be determined. For example, the determining manner for presence of the GAPDH nucleic acid amplification product may comprise, a gel electrophoresis analysis, a lateral flow immunoassay, etc., but it is not limited thereto.

In the method for detecting GAPDH nucleic acid of the present disclosure, the loop-mediated isothermal amplification mentioned above may use a single-stranded RNA or first strand cDNA as an initial template, but it is not limited thereto.

In one embodiment, in the method for detecting GAPDH nucleic acids of the present disclosure, the sample to be tested mentioned above may be a sample not subjected to any purification process, for example, subjected to no nucleic acid purification process. Namely, the method for detecting GAPDH nucleic acids of the present disclosure may perform the loop-mediated isothermal amplification mentioned above on a sample not subjected to any purification process and obtain an accurate GAPDH nucleic acid detection result to achieve an effect of reducing or eliminating processing a sample to be tested. In one specific embodiment, the sample to be tested mentioned above may be a primitive saliva specimen.

In one embodiment, the method for detecting GAPDH nucleic acids of the present disclosure may further comprise performing a pretreatment on a biosample to obtain the sample to be tested before providing the sample to be tested. The pretreatment mentioned above may comprise, but is not limited to one of the following steps:

(i) performing a heat treatment step on the biosample;
(ii) performing a nucleic acid purification step on the biosample;
(iii) performing a reverse transcription step on the biosample;
(iv) performing a reverse transcription step on the biosample after performing a nucleic acid purification step on the biosample;
(v) performing an RNA removal step after performing a reverse transcription step on the biosample; and
(vi) performing a reverse transcription step and then an RNA removal step on the biosample after performing a nucleic acid purification step on the biosample.

Temperature of the foregoing heat treatment step may be about 45-100° C., such as about 50-95° C., about 55-90° C., about 60° C., about 70° C., about 80° C., about 90° C., about 95° C., but it is not limited thereto.

The foregoing biosample may comprise, a saliva specimen, a sputum specimen, a nose swab specimen, a throat swab specimen, a nasopharyngeal specimen, a urine specimen, a stool specimen, a rectal swab specimen, a cerebrospinal fluid (CSF) specimen, a body fluid specimen, etc., but it is not limited thereto. In one embodiment, the foregoing biosample may be a saliva specimen.

In addition, in the method for detecting GAPDH nucleic acids of the present disclosure mentioned above, the loop-mediated isothermal amplification mentioned above may comprise a standard loop-mediated isothermal amplification, a reverse transcription loop-mediated isothermal amplification, etc., but it is not limited thereto.

In one embodiment, the loop-mediated isothermal amplification in the method for detecting GAPDH nucleic acids of the present disclosure mentioned above may be a reverse transcription loop-mediated isothermal amplification. In one specific embodiment, in the reverse transcription loop-mediated isothermal amplification mentioned above, a reverse transcription procedure and a loop-mediated isothermal amplification procedure are performed in one step, and in the reverse transcription loop-mediated isothermal amplification mentioned above, a polymerase with a function of reverse transcriptase, such as a Bst DNA polymerase may be used, but it is not limited thereto. Example of the Bst DNA polymerase mentioned above may comprise, but is not limited to a Bst DNA polymerase of which the sequence may comprise the amino acid sequence of SEQ ID NO. 10. In another specific embodiment, in the reverse transcription loop-mediated isothermal amplification mentioned above, a loop-mediated isothermal amplification procedure is performed after a reverse transcription procedure, and in this specific embodiment, the reverse transcription procedure may be performed by a reverse transcriptase with a function of a ribonuclease (RNase), but it is not limited thereto, and the ribonuclease (RNase) mentioned above may comprise, but is not limited to ribonuclease H (RNase H), etc.

In addition, according to the foregoing, the present disclosure may also provide a method for detecting target nucleic acids.

The method for detecting the target nucleic acids of the present disclosure may comprise, but is not limited to the following steps.

First, a sample to be tested is provided. The relevant description for a source of the sample to be tested can be the same as the relevant description for the source of the sample to be tested mentioned in the foregoing paragraphs regarding to the target nucleic acid detection kit of the present disclosure, and thus it will be not repeated herein. In one embodiment, the source of the sample to be tested mentioned above may be a saliva specimen.

Next, a first loop-mediated isothermal amplification and a second loop-mediated isothermal amplification are respectively performed on the sample to be tested mentioned above by the primer set for detecting GAPDH nucleic acids and the primer set for detecting target nucleic acids in any target nucleic acid detection kit of the present disclosure mentioned above. If the sample to be tested mentioned above contains the target nucleic acid mentioned above, a GAPDH nucleic acid amplification product as an internal control may be obtained from the first loop-mediated isothermal amplification mentioned above, and a target nucleic acid amplification product may be obtained from the second loop-mediated isothermal amplification mentioned above.

Furthermore, in one embodiment, in the method for detecting target nucleic acid of the present disclosure, a determining manner for presence of the GAPDH nucleic acid amplification product mentioned above or the target nucleic acid amplification product mentioned above has no particular limitation, as long as the presence of the GAPDH nucleic acid amplification product mentioned above or the target nucleic acid amplification product mentioned above can be determined. The determining manner for presence of the GAPDH nucleic acid amplification product mentioned above or the target nucleic acid amplification product mentioned above may comprise, a gel electrophoresis analysis, a lateral flow immunoassay, etc., but it is not limited thereto.

In the method for detecting target nucleic acid of the present disclosure, the first loop-mediated isothermal amplification and the second loop-mediated isothermal amplification mentioned above may use a single-stranded RNA or first strand cDNA as an initial template, but it is not limited thereto.

In one embodiment, in the method for detecting target nucleic acids of the present disclosure, the sample to be tested mentioned above may be a sample not subjected to any purification process, for example, subjected to no nucleic acid purification process. Namely, the method for detecting target nucleic acids of the present disclosure may perform the first loop-mediated isothermal amplification and the second loop-mediated isothermal amplification mentioned above on a sample not subjected to any purification process and obtain an accurate target nucleic acid detection result to achieve an effect of reducing or eliminating processing a sample to be tested. In one specific embodiment, the sample to be tested mentioned above may be a primitive saliva specimen.

In one embodiment, the method for detecting target nucleic acids of the present disclosure may further comprise performing a pretreatment on a biosample to obtain the sample to be tested before providing the sample to be tested.

The pretreatment mentioned above may comprise, but is not limited to one of the following steps:
(i) performing a heat treatment step on the biosample;
(ii) performing a nucleic acid purification step on the biosample;
(iii) performing a reverse transcription step on the biosample;
(iv) performing a reverse transcription step on the biosample after performing a nucleic acid purification step on the biosample;
(v) performing an RNA removal step after performing a reverse transcription step on the biosample; and
(vi) performing a reverse transcription step and then an RNA removal step on the biosample after performing a nucleic acid purification step on the biosample.

Temperature of the foregoing heat treatment step may be about 45-100° C., such as about 50-95° C., about 55-90° C., about 60° C., about 70° C., about 80° C., about 90° C., about 95° C., but it is not limited thereto.

The foregoing biosample may comprise, a saliva specimen, a sputum specimen, a nose swab specimen, a throat swab specimen, a nasopharyngeal specimen, a urine specimen, a stool specimen, a rectal swab specimen, a cerebrospinal fluid (CSF) specimen, a body fluid specimen, etc., but it is not limited thereto. In one embodiment, the foregoing biosample may be a saliva specimen.

In addition, in the method for detecting target nucleic acids of the present disclosure mentioned above, the first loop-mediated isothermal amplification mentioned above or the second loop-mediated isothermal amplification mentioned above may comprise a standard loop-mediated isothermal amplification, a reverse transcription loop-mediated isothermal amplification, etc., but it is not limited thereto.

In one embodiment, the first loop-mediated isothermal amplification mentioned above or the second loop-mediated isothermal amplification mentioned above in the method for detecting target nucleic acids of the present disclosure mentioned above may be a reverse transcription loop-mediated isothermal amplification. In one specific embodiment, in the reverse transcription loop-mediated isothermal amplification mentioned above, a reverse transcription procedure and a loop-mediated isothermal amplification procedure are performed in one step, and in the reverse transcription loop-mediated isothermal amplification mentioned above, a polymerase with a function of reverse transcriptase, such as a Bst DNA polymerase may be used, but it is not limited thereto. Example of the Bst DNA polymerase mentioned above may comprise, but is not limited to a Bst DNA polymerase of which the sequence may comprise the amino acid sequence of SEQ ID NO. 10. In another specific embodiment, in the reverse transcription loop-mediated isothermal amplification mentioned above, a loop-mediated isothermal amplification procedure is performed after a reverse transcription procedure, and in this specific embodiment, the reverse transcription procedure may be performed by a reverse transcriptase with a function of a ribonuclease (RNase), but it is not limited thereto, and the ribonuclease (RNase) mentioned above may comprise, but is not limited to ribonuclease H (RNase H), etc.

In one embodiment, the detection target of the method for detecting target nucleic acids of the present disclosure may be nucleic acids of an RNA virus. Example of the RNA virus may comprise a coronavirus, an influenza virus, a human immunodeficiency virus (HIV), Ebola virus, hepatitis C virus (HCV), but it is not limited thereto.

The coronavirus mentioned above may comprise, but is not limited to severe acute respiratory syndrome coronavirus (SARS-CoV or 2019-nCoV), severe acute respiratory syndrome coronavirus 2 (SARS-CoV-2 or 2019-nCoV), Middle East respiratory syndrome coronavirus (MERS-CoV), etc.

In addition, nucleic acids of the severe acute respiratory syndrome coronavirus type 2 (SARS-CoV-2 or 2019-nCoV) mentioned above may comprise, but is not limited to nucleic acids within the range of ORF1ab (e.g., nucleic acids of the RdRp gene, but it is not limited thereto), nucleic acids of spike protein (S) gene, nucleic acids of envelope (E) gene, nucleic acids of membrane protein (M) gene, nucleic acids of nucleoprotein (N) gene, etc.

In one embodiment, the detection target of the method for detecting target nucleic acids of the present disclosure may be nucleic acids of the RdRp gene of severe acute respiratory syndrome coronavirus type 2 (SARS-CoV-2 or 2019-nCoV).

In the embodiment in which the detection target of the method for detecting target nucleic acids of the present disclosure may be nucleic acids of the RdRp gene of severe acute respiratory syndrome coronavirus type 2 (SARS-CoV-2 or 2019-nCoV), the primer set for detecting target nucleic acids in the target nucleic acid detection kit of the present disclosure which is adopted may be any primer set for detecting target nucleic acids mentioned in the paragraphs for the related embodiments when the detection target of the primer set for detecting target nucleic acids in the target nucleic acid detection kit of the present disclosure mentioned above may be nucleic acids of the RdRp gene of severe acute respiratory syndrome coronavirus type 2 (SARS-CoV-2 or 2019-nCoV), but it is not limited thereto.

Furthermore, based on the foregoing, the present disclosure may also provide a method for detecting SARS-CoV-2.

The method for detecting SARS-CoV-2 of the present disclosure may comprise, but is not limited to the following steps.

First, a sample to be tested is provided. The relevant description for a source of the sample to be tested can be the same as the relevant description for the source of the sample to be tested mentioned in the foregoing paragraphs regarding to the target nucleic acid detection kit of the present disclosure, and thus it will be not repeated herein. In one embodiment, the source of the sample to be tested mentioned above may be a saliva specimen.

Next, a loop-mediated isothermal amplification is performed on the sample to be tested mentioned above by any foregoing primer set for detecting SARS-CoV-2 nucleic acids in the SARS-CoV-2 detection kit of the present disclosure. If the sample to be tested contains SARS-CoV-2, a SARS-CoV-2 nucleic acid amplification product may be obtained from the loop-mediated isothermal amplification mentioned above.

Furthermore, in one embodiment, in the method for detecting SARS-CoV-2 of the present disclosure, a determining manner for presence of the SARS-CoV-2 nucleic acid amplification product has no particular limitation, as long as the presence of the SARS-CoV-2 nucleic acid amplification product can be determined. For example, the determining manner for presence of the SARS-CoV-2 nucleic acid amplification product may comprise, a gel electrophoresis analysis, a lateral flow immunoassay, etc., but it is not limited thereto.

In the method for detecting SARS-CoV-2 of the present disclosure, the loop-mediated isothermal amplification mentioned above may use a single-stranded RNA or first strand cDNA as an initial template, but it is not limited thereto.

In one embodiment, in the method for detecting SARS-CoV-2 of the present disclosure, the sample to be tested mentioned above may be a sample not subjected to any purification process, for example, subjected to no nucleic acid purification process. Namely, the method for detecting SARS-CoV-2 of the present disclosure may perform the loop-mediated isothermal amplification mentioned above on a sample not subjected to any purification process and obtain an accurate SARS-CoV-2 detection result to achieve an effect of reducing or eliminating processing a sample to be tested. In one specific embodiment, the sample to be tested mentioned above may be a primitive saliva specimen.

In one embodiment, the method for detecting SARS-CoV-2 of the present disclosure may further comprise performing a pretreatment on a biosample to obtain the sample to be tested before providing the sample to be tested. The pretreatment mentioned above may comprise, but is not limited to one of the following steps:

(i) performing a heat treatment step on the biosample;
(ii) performing a nucleic acid purification step on the biosample;
(iii) performing a reverse transcription step on the biosample;
(iv) performing a reverse transcription step on the biosample after performing a nucleic acid purification step on the biosample;
(v) performing an RNA removal step after performing a reverse transcription step on the biosample; and
(vi) performing a reverse transcription step and then an RNA removal step on the biosample after performing a nucleic acid purification step on the biosample.

Temperature of the foregoing heat treatment step may be about 45-100° C., such as about 50-95° C., about 55-90° C., about 60° C., about 70° C., about 80° C., about 90° C., about 95° C., but is not limited thereto.

The foregoing biosample may comprise, a saliva specimen, a sputum specimen, a nose swab specimen, a throat swab specimen, a nasopharyngeal specimen, a urine specimen, a stool specimen, a rectal swab specimen, a cerebrospinal fluid (CSF) specimen, a body fluid specimen, etc., but it is not limited thereto. In one embodiment, the foregoing biosample may be a saliva specimen.

In addition, in the method for detecting SARS-CoV-2 of the present disclosure mentioned above, the loop-mediated isothermal amplification mentioned above may comprise a standard loop-mediated isothermal amplification, a reverse transcription loop-mediated isothermal amplification, etc., but it is not limited thereto.

In one embodiment, the loop-mediated isothermal amplification in the method for detecting SARS-CoV-2 of the present disclosure mentioned above may be a reverse transcription loop-mediated isothermal amplification. In one specific embodiment, in the reverse transcription loop-mediated isothermal amplification mentioned above, a reverse transcription procedure and a loop-mediated isothermal amplification procedure are performed in one step, and in the reverse transcription loop-mediated isothermal amplification mentioned above, a polymerase with a function of reverse transcriptase, such as a Bst DNA polymerase may be used, but it is not limited thereto. Example of the Bst DNA polymerase mentioned above may comprise, but is not limited to a Bst DNA polymerase of which the sequence may comprise the amino acid sequence of SEQ ID NO. 10. In another specific embodiment, in the reverse transcription loop-mediated isothermal amplification mentioned above, a loop-mediated isothermal amplification procedure is performed after a reverse transcription procedure, and in this specific embodiment, the reverse transcription procedure may be performed by a reverse transcriptase with a function of a ribonuclease (RNase), but it is not limited thereto, and the ribonuclease (RNase) mentioned above may comprise, but is not limited to ribonuclease H (RNase H), etc.

Moreover, nucleic acids of the SARS-CoV-2 mentioned above may comprise, but is not limited to nucleic acids within the range of ORF1ab (e.g., nucleic acids of the RdRp gene, but it is not limited thereto), nucleic acids of spike protein (S) gene, nucleic acids of envelope (E) gene, nucleic acids of membrane protein (M) gene, nucleic acids of nucleoprotein (N) gene, etc.

In one embodiment, the detection target of the method for detecting SARS-CoV-2 of the present disclosure may be nucleic acids of the RdRp gene of SARS-CoV-2.

EXAMPLES

A. Materials and Methods

A-1. Inactivated Severe Acute Respiratory Syndrome Coronavirus Type 2 (SARS-CoV-2)

The inactivated SARS-CoV-2 virus was purchased from BEI Resources (Catalog No. NR-52286; Lot: 70034991).

A-2. Preparation of Synthetic SARS-CoV-2 RNA Control

Synthetic SARS-CoV-2 RNA (GenBank ID: MT007544.1; Model: 102019) was purchased from Twist Bioscience.

The synthetic SARS-CoV-2 RNA was diluted with sterile 1× RNAsecure™ RNase Inactivation Reagent (brand: Thermo Fisher Scientific Inc.; model: AM7006) to a final concentration of $2.5 \times 10^4$ copies/mL, as the positive control for each reverse transcription loop-mediated isothermal amplification (RT-LAMP).

A-3. Primers Used in Reverse Transcription Loop-Mediated Isothermal Amplification:

1. Primer Sets for GAPDH

Part of the mRNA sequence of GAPDH (NCBI Accession Number NM_001256799) (SEQ ID NO. 1) was used to design primer sets for GAPDH.

Five primer sets designed for use in the reverse transcription loop-mediated isothermal amplification are shown in Table 1 below.

TABLE 1

Selected six regions and designed primer set for nucleotide sequence of SEQ ID NO. 1

| Design of primer set based on nucleotide sequence of SEQ ID NO. 1 Primer set GAPDH-103 | | | | |
|---|---|---|---|---|
| Selected regions and designed primers | 5' end position | 3' end position | Length | Sequence |
| F3 region (Forward outer primer) | 52 | 69 | 18 | GATGCTGGCGCTGAGTAC (SEQ ID NO. 3) |

TABLE 1-continued

Selected six regions and designed primer set for nucleotide sequence of SEQ ID NO. 1

| | | | | |
|---|---|---|---|---|
| F2 region | 87 | 105 | 19 | CGTCTTCACCACCATGGAG (SEQ ID NO. 19) |
| F1c region | 144 | 165 | 22 | AGCAGAGGGGGCAGAGAT GATG (SEQ ID NO. 18) |
| B1c region | 176 | 197 | 22 | TGTTCGTCATGGGTGTGAA CCA (SEQ ID NO. 20) |
| B2 region | 221 | 240 | 20 | GGAGGCATTGCTGATGATC T (SEQ ID NO. 21) |
| B3 region (Backward outer primer) | 248 | 265 | 18 | GGGGTGCTAAGCAGTTGG (SEQ ID NO. 5) |
| FIP (Forward inner primer) | | | 47 | AGCAGAGGGGGCAGAGAT GATGTTTTTCGTCTTCAC CACCATGGAG (SEQ ID NO. 2) |
| BIP (Backward inner primer) | | | 48 | TGTTCGTCATGGGTGTGAA CCATTTTTTGGAGGCATTG CTGATGATCT (SEQ ID NO. 4) |

Primer set GAPDH-103-B3-I

| Selected regions and designed primers | 5' end position | 3' end position | Length | Sequence |
|---|---|---|---|---|
| F3 region (Forward outer primer) | 52 | 69 | 18 | GATGCTGGCGCTGAGTAC (SEQ ID NO. 3) |
| F2 region | 87 | 105 | 19 | CGTCTTCACCACCATGGAG (SEQ ID NO. 19) |
| F1c region | 144 | 165 | 22 | AGCAGAGGGGGCAGAGAT GATG (SEQ ID NO. 18) |
| B1c region | 176 | 197 | 22 | TGTTCGTCATGGGTGTGAA CCA (SEQ ID NO. 20) |
| B2 region | 221 | 240 | 20 | GGAGGCATTGCTGATGATC T (SEQ ID NO. 21) |
| B3 region (Backward outer primer) | 248 | 265 | 18 | GGGGTGCIIIIIAGTTGG (SEQ ID NO. 9) |
| FIP (Forward inner primer) | | | 47 | AGCAGAGGGGGCAGAGAT GATGTTTTTCGTCTTCAC CACCATGGAG (SEQ ID NO. 2) |
| BIP (Backward inner primer) | | | 48 | TGTTCGTCATGGGTGTGAA CCATTTTTTGGAGGCATTG CTGATGATCT (SEQ ID NO. 4) |

Primer set GAPDH-103-BIP-3

| Selected regions and designed primers | 5' end position | 3' end position | Length | Sequence |
|---|---|---|---|---|
| F3 region (Forward outer primer) | 52 | 69 | 18 | GATGCTGGCGCTGAGTAC (SEQ ID NO. 3) |
| F2 region | 87 | 105 | 19 | CGTCTTCACCACCATGGAG (SEQ ID NO. 19) |

TABLE 1-continued

Selected six regions and designed primer set for nucleotide sequence of SEQ ID NO. 1

| | | | | |
|---|---|---|---|---|
| F1c region | 144 | 165 | 22 | AGCAGAGGGGGCAGAGAT GATG (SEQ ID NO. 18) |
| B1c region | 176 | 197 | 22 | TGTTCGTCATGGGTGTGAA CCA (SEQ ID NO. 20) |
| B2 region | 229 | 246 | 18 | GGTGCAGGAGGCATTGCT (SEQ ID NO. 22) |
| B3 region (Backward outer primer) | 248 | 265 | 18 | GGGGTGCTAAGCAGTTGG (SEQ ID NO. 5) |
| FIP (Forward inner primer) | | | 47 | AGCAGAGGGGGCAGAGAT GATGTTTTTCGTCTTCAC CACCATGGAG (SEQ ID NO. 2) |
| BIP (Backward inner primer) | | | 46 | TGTTCGTCATGGGTGTGAA CCATTTTTTGGTGCAGGAG GCATTGCT (SEQ ID NO. 6) |

Primer set GAPDH-103-B3/BIP-3-I

| Selected regions and designed primers | 5' end position | 3' end position | Length | Sequence |
|---|---|---|---|---|
| F3 region (Forward outer primer) | 52 | 69 | 18 | GATGCTGGCGCTGAGTAC (SEQ ID NO. 3) |
| F2 region | 87 | 105 | 19 | CGTCTTCACCACCATGGAG (SEQ ID NO. 19) |
| F1c region | 144 | 165 | 22 | AGCAGAGGGGGCAGAGAT GATG (SEQ ID NO. 18) |
| B1c region | 176 | 197 | 22 | TGTTCGTCATGGGTGTGAA CCA (SEQ ID NO. 20) |
| B2 region | 229 | 246 | 18 | GGTGCAGGAGGCATTGCT (SEQ ID NO. 22) |
| B3 region (Backward outer primer) | 248 | 265 | 18 | GGGGTGCIIIIIAGTTGG (SEQ ID NO. 9) |
| FIP (Forward inner primer) | | | 47 | AGCAGAGGGGGCAGAGAT GATGTTTTTCGTCTTCAC CACCATGGAG (SEQ ID NO. 2) |
| BIP (Backward inner primer) | | | 46 | TGTTCGTCATGGGTGTGAA CCATTTTTTGGTGCIIIIIGCA TTGCT (SEQ ID NO. 8) |

Primer set GAPDH-103-BIP-4

| Selected regions and designed primers | 5' end position | 3' end position | Length | Sequence |
|---|---|---|---|---|
| F3 region (Forward outer primer) | 52 | 69 | 18 | GATGCTGGCGCTGAGTAC (SEQ ID NO. 3) |
| F2 region | 87 | 105 | 19 | CGTCTTCACCACCATGGAG (SEQ ID NO. 19) |
| F1c region | 144 | 165 | 22 | AGCAGAGGGGGCAGAGAT GATG (SEQ ID NO. 18) |

TABLE 1-continued

Selected six regions and designed primer set for nucleotide sequence of SEQ ID NO. 1

| | | | | |
|---|---|---|---|---|
| B1c region | 176 | 197 | 22 | TGTTCGTCATGGGTGTGAACCA (SEQ ID NO. 20) |
| B2 region | 228 | 245 | 18 | GTGCAGGAGGCATTGCTG (SEQ ID NO. 23) |
| B3 region (Backward outer primer) | 248 | 265 | 18 | GGGGTGCTAAGCAGTTGG (SEQ ID NO. 5) |
| FIP (Forward inner primer) | | | 47 | AGCAGAGGGGGCAGAGATGATGTTTTTTCGTCTTCACCACCATGGAG (SEQ ID NO. 2) |
| BIP (Backward inner primer) | | | 46 | TGTTCGTCATGGGTGTGAACCATTTTTTGTGCAGGAGGCATTGCTG (SEQ ID NO. 7) |

Note:
I represents inosine

2. Primer Set for RdRp Gene of Severe Acute Respiratory Syndrome Coronavirus Type 2

Part of the ORF1ab nucleic acids of severe acute respiratory syndrome coronavirus type 2 (NCBI Accession Number MN908947) (SEQ ID NO. 11) was used to design a primer set for the nucleic acids of the RdRp gene.

One primer set designed for use in the reverse transcription loop-mediated isothermal amplification are shown in Table 2 below.

TABLE 2

Selected eight regions and designed primer set for nucleotide sequence of SEQ ID NO. 11
Design of primer set based on nucleotide sequence of SEQ ID NO. 11
Primer set RdRp

| Selected regions and designed primers | 5' end position | 3' end position | Length | Sequence |
|---|---|---|---|---|
| F3 region (Forward outer primer) | 37 | 54 | 18 | ATGGCCTCACTTGTTCTT (SEQ ID NO. 13) |
| F2 region | 55 | 72 | 18 | GCTCGCAAACATACAACG (SEQ ID NO. 25) |
| F1c region | 100 | 124 | 25 | CTTGAGCACACTCATTAGCTAATCT (SEQ ID NO. 24) |
| B1c region | 133 | 155 | 23 | GAAATGGTCATGTGTGGCGGTTC (SEQ ID NO. 26) |
| B2 region | 180 | 198 | 19 | TGTGGCATCTCCTGATGAG (SEQ ID NO. 27) |
| B3 region (Backward outer primer) | 236 | 253 | 18 | TAACATTGGCCGTGACAG (SEQ ID NO. 15) |
| FIP (Forward inner primer) | | | 49 | CTTGAGCACACTCATTAGCTAATCTTTTTTTGCTCGCAAACATACAACG (SEQ ID NO. 12) |
| BIP (Backward inner primer) | | | 48 | GAAATGGTCATGTGTGGCGGTTCTTTTTTTGTGGCATCTCCTGATGAG (SEQ ID NO. 14) |
| FLP (Forward loop primer) | 73 | 94 | 22 | AACGGTGTGACAAGCTACAACA (SEQ ID NO. 16) |

TABLE 2-continued

Selected eight regions and designed primer set for nucleotide sequence
of SEQ ID NO. 11
Design of primer set based on nucleotide sequence of SEQ ID NO. 11
Primer set RdRp

| Selected regions and designed primers | 5' end position | 3' end position | Length | Sequence |
|---|---|---|---|---|
| BLP (Backward loop primer) | 156 | 177 | 22 | ACTATATGTTAAACCAGGT GGA (SEQ ID NO. 17) |

A-5. Reverse Transcription Loop-Mediated Isothermal Amplification

1. Concentration Used for Primers:

In the reverse transcription loop-mediated isothermal amplification, the concentration used for each primer is as follows.

The final concentration of each primer used to amplify the human GAPDH gene: FIP/BIP was 0.8 µM; F3/B3 was 0.1 µM.

The final concentration of each primer used to amplify the nucleic acid sequence of SARS-CoV-2 RdRp: FIP/BIP was 0.8 µM; F3/B3 was 0.1 µM; FLP/BLP was 0.2 µM.

2. Reaction Reagents and Conditions (1) Commercial RT/Bst Mix Reagents as Polymerase The reverse transcription loop-mediated isothermal amplification was performed by a commercial RT/Bst mix reagent (WarmStart LAMP kit (Cat No. E1700L); New England Biolabs).

The reaction temperature was 65° C. and the reaction time was 60 minutes. Each ingredient required for the reaction and volume thereof are shown in Table 3.

TABLE 3

| Ingredients | Experimental group | Positive quality control | Negative quality control |
|---|---|---|---|
| RT/Bst mix | 10 µL | 10 µL | 10 µL |
| Primer set | 1 µL | 1 µL | 1 µL |
| Sample to be tested* | 9 µL | 0 µL | 0 µL |
| Synthesized SARS-CoV-2 RNA control | 0 µL | 9 µL | 0 µL |
| 1X RNAsecure™ RNase Inactivation Reagent | 0 µL | 0 µL | 9 µL |
| Total volume | 20 µL | 20 µL | 20 µL |

*The sample to be tested may be saliva containing SARS-CoV-2 virus or SARS-CoV-2 RNA control, or genomic DNA or total RNA of Expi293 cells.

(2) Recombinant Bst DNA Polymerase Large Fragment as Polymerase

Recombinant Bst DNA polymerase large fragment was used as a polymerase, and the amino acid thereof (SEQ ID NO. 10) is shown in the following:

MGSSHHHHHHSGGPEQKLISEEDLPGGSWSHPQFEKSGLVPRGSGRAV

QTDEGEKPLAGMDFAIADSVTDEMLADKAALVVEVVGDNYHHAPIVGIA

LANERGRFFLRPETALADPKFLAWLGDETKKKTMFDSKRAAVALKWKGI

ELRGVVFDLLLAAYLLDPAQAAGDVAAVAKMHQYEAVRSDEAVYGKGAK

RTVPDEPTLAEHLVRKAAAIWALEEPLMDELRRNEQDRLLTELEQPLAG

ILANMEFTGVKVDTKRLEQMGAELTEQLQAVERRIYELAGQEFNINSPK

QLGTVLFDKLQLPVLKKTKTGYSTSADVLEKLAPHHEIVEHILHYRQLG

KLQSTYIEGLLKVVHPVTGKVHTMFNQALTQTGRLSSVEPNLQNIPIRL

EEGRKIRQAFVPSEPDWLIFAADYSQIELRVLAHIAEDDNLIEAFRRGL

DIHTKTAMDIFHVSEEDVTANMRRQAKAVNFGIVYGISDYGLAQNLNIT

RKEAAEFIERYFASFPGVKQYMDNIVQEAKQKGYVTTLLHRRRYLPDIT

SRNFNVRSFAERTAMNTPIQGSAADIIKKAMIDLSVRLREERLQARLLL

QVHDELILEAPKEEIERLCRLVPEVMEQAVALRVPLKVDYHYGPTWYDA

K

Histidine-tag (HHHHHH) (SEQ ID NO. 28), c-myc-tag (EQKLISEEDL) (SEQ ID NO. 29), Strep-tag II (WSHPQFEK) (SEQ ID NO. 30) and thrombin cleavage site (LVPRGS) (SEQ ID NO. 31) contained in the N-terminal sequence are shown in bold and underlined.

The reaction temperature was 65° C. and the reaction time was 60 minutes. Each ingredient required for the reaction and volume thereof are shown in Table 4.

TABLE 4

| Ingredients | BEI | No template control (NTC) |
|---|---|---|
| 10× isothermal amplification buffer (pH 8.8) | 2 µL | 2 µL |
| 100 mM MgSO$_4$ | 1.2 µL | 1.2 µL |
| RdRp primer set | 1 µL | 1 µL |
| 10 mM dNTP | 2.8 µL | 2.8 µL |
| Bst DNA polymerase large fragment | 1 µL | 1 µL |
| RNA template | 9 µL | 0 µL |
| H$_2$O | 3 µL | 12 µL |
| Total volume | 20 µL | 20 µL |

Ingredients of 10× isothermal amplification buffer (pH 8.8) are shown in the following:
  200 mM Tris-HCl
  100 mM (NH$_4$)$_2$SO$_4$
  500 mM KCl
  20 mM MgSO$_4$
  1% Tween-20

A-6. Lateral Flow Immunoassay

A commercial nucleic acid lateral flow immunoassay (NALFIA) test strip, PCRD FLEX Dipstick (model FG-FD51676, brand Abingdon Health), was used for lateral flow immunoassay.

The PCRD FLEX Dipstick has an analyte addition area, a binding area, a first test line (T1), a second test line (T2) and a control line (C), sequentially according to the flow direction of the analyte. When the analyte addition area of the test strip is inserted into a reaction sample containing a product of reverse transcription loop-mediated isothermal amplification, the carbon particles of which the surface is coated with NeutrAvidin on the binding area of the test strip will bind to the digoxigenin (DIG)/biotin of a DNA amplification product labeled with digoxigenin (DIG)/biotin and the fluorescein (FAM)/biotin of a DNA amplification product labeled with fluorescein (FAM))/biotin contained in the reaction sample, and move along the nitrocellulose membrane through the capillary phenomenon.

If the reaction sample contains a DNA amplification product labeled with digoxigenin (DIG)/biotin, the digoxigenin (DIG) of the DNA amplification product labeled with digoxigenin (DIG)/biotin will bind to anti-DIG antibody on the T1 test line to form a dark gray complex and can be recognizable by the naked eye; if the reaction sample contains a DNA amplification product labeled with fluorescein (FAM)/biotin, the fluorescein (FAM) of the DNA amplification product labeled with fluorescein (FAM)/biotin will bind to anti-FAM antibody on the T2 test line to form a dark gray line visible to the naked eye.

Finally, the carbon particles coated with mouse serum will be grabbed at the control line to form a dark gray line visible to the naked eye, which serves as the quality control line for the nuclear acid lateral flow immunoassay test strip.

B. Results

Example 1

Detection of SARS-CoV-2 RdRp and Human GAPDH in Saliva by Reverse Transcription Loop-Mediated Isothermal Amplification (One-Step Reaction)

The synthetic SARS-CoV-2 RNA control (Twist Bioscience) was added to a SARS-CoV-2-negative saliva specimen at a final concentration of $1 \times 10^4$ copies/mL.

After that, the foregoing saliva specimen containing the synthetic SARS-CoV-2 RNA control was extracted with QIAamp Viral RNA Mini Kit (brand: Qiagen, model: 52906) to obtain total RNA.

9 μL of total RNA was used as a nucleic acid template, mixed with RdRp primer set (the 5' end of the forward inner primer was labeled with FAM, the 5' end of the backward inner primer was labeled with biotin) and RT/Bst mix and subjected to a reverse transcription loop-mediated isothermal amplification. Moreover, 9 μL of total RNA was used as a nucleic acid template, mixed with GAPDH-103 primer set (the 5' end of the forward inner primer was labeled with DIG, the 5' end of the backward inner primer was labeled with biotin) and RT/Bst mix and subjected to another reverse transcription loop-mediated isothermal amplification. On the other hand, 9 μL of 1× RNAsecure™ RNase Inactivation Reagent was used to replace the total RNA template, RdRp primer set and GAPDH-103 primer set were respectively added thereto, RT/Bst mix was mixed therewith, and reverse transcription loop-mediated isothermal amplifications were performed as no template controls (NTCs). In addition, the synthetic SARS-CoV-2 RNA control was directly mixed with RdRp primer set (the 5' end of the forward inner primer was labeled with FAM, the 5' end of the backward inner primer was labeled with biotin) and RT/Bst mix and subjected to a reverse transcription loop-mediated isothermal amplification as a positive control.

The two products obtained by respectively performing reverse transcription loop-mediated isothermal amplifications with RdRp primer set and GAPDH-103 primer set on the foregoing saliva specimen containing the synthetic SARS-CoV-2 RNA control were subjected to an electrophoresis by 2% agarose gel. The results are shown in FIG. 3A and FIG. 3B, respectively.

The mixture obtained by mixing the two products which were obtained by respectively performing reverse transcription loop-mediated isothermal amplifications with RdRp primer set and GAPDH-103 primer set on the foregoing saliva specimen containing the synthetic SARS-CoV-2 RNA control were subjected to a lateral flow immunoassay. The results are shown in FIG. 3C.

FIG. 3A shows that performing a reverse transcription loop-mediated isothermal amplification on the total RNA extracted from the saliva specimen containing the synthetic SARS-CoV-2 RNA control with the RdRp primer set can obtain a ladder-like amplification product. The positive control can also obtain a ladder-like amplification product.

FIG. 3B also shows that performing a reverse transcription loop-mediated isothermal amplification on the total RNA extracted from the saliva specimen containing the synthetic SARS-CoV-2 RNA control with the GAPDH-103 primer set can obtain a ladder-like amplification product.

FIG. 3C shows that the two products obtained by respectively performing reverse transcription loop-mediated isothermal amplifications with RdRp primer set and GAPDH-103 primer set on the foregoing saliva specimen containing the synthetic SARS-CoV-2 RNA control can respectively form dark gray lines on T1 test line and T2 test line of one lateral flow immunoassay test strip. The product of the positive control only form a dark gray lines on T2 test line while the product of the no template control present no dark gray line on both of T1 test line and T2 test line.

Based on the results mentioned above, it is understood that the RdRp primer set of the present disclosure can detect SARS-CoV-2 in a saliva specimen, indeed, and the GAPDH primer set of the present disclosure indeed can obtain a product in a reverse transcription loop-mediated isothermal amplification for total RNA of a saliva specimen, and the product can be used as an internal control.

Example 2

Detection of SARS-CoV-2 RdRp by Reverse Transcription Loop-Mediated Isothermal Amplification (Two-Step Reaction)

The synthetic SARS-CoV-2 RNA control (Twist Bioscience) (a final concentration of $1 \times 10^4$ copies/mL) (single-stranded RNA) was used as a template and mixed with SuperScript IV reverse transcriptase (Invitrogen) for reverse transcription (50° C. for reacting 15 minutes) to form an RNA-cDNA hybrid.

Next, the reverse transcription product was heated at 95° C. for 3 minutes to degrade the RNA to obtain single-stranded cDNA. After that, the cDNA was diluted 5 folds and 10 folds, respectively.

2 μL of cDNA (undiluted, 5-fold diluted or 10-fold diluted) was subjected to a loop-mediated isothermal amplification. The products of the loop-mediated isothermal amplification were analyzed by electrophoresis with 2% agarose gel. The results are shown in FIG. 4, respectively.

Figure 4:
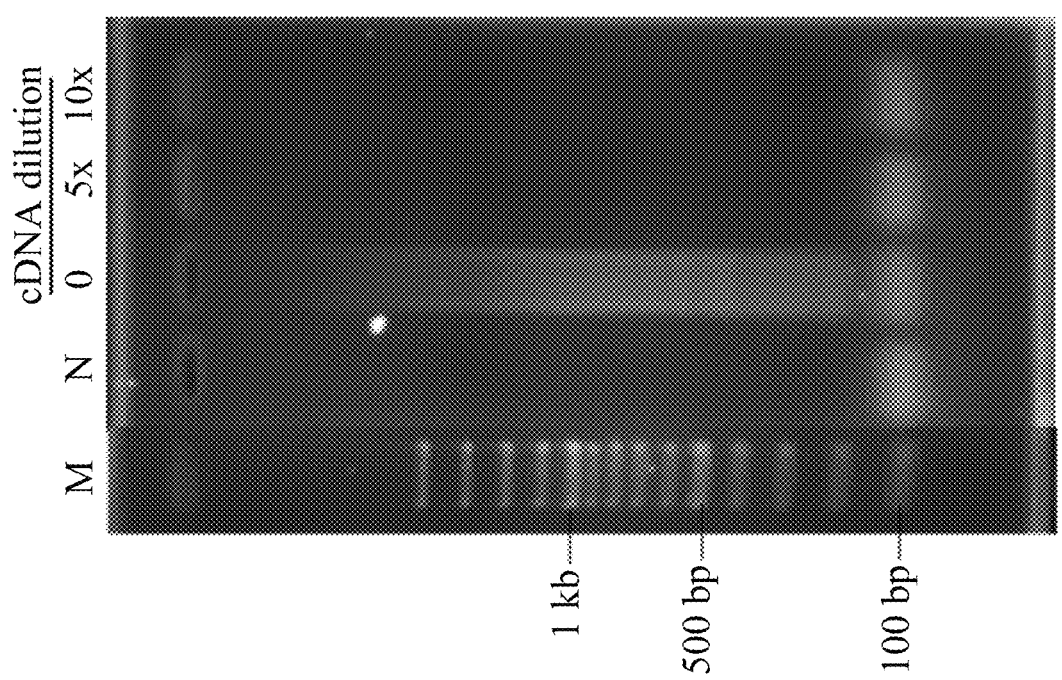
FIG. 4 shows an electrophoresis analysis result of a product obtained by performing a reverse transcription loop-mediated isothermal amplification (two-step reaction) on synthetic SARS-CoV-2 RNA control with RdRp primer set. M: DNA molecular weight standard; N: no template control.
Figures 5A, 5B:
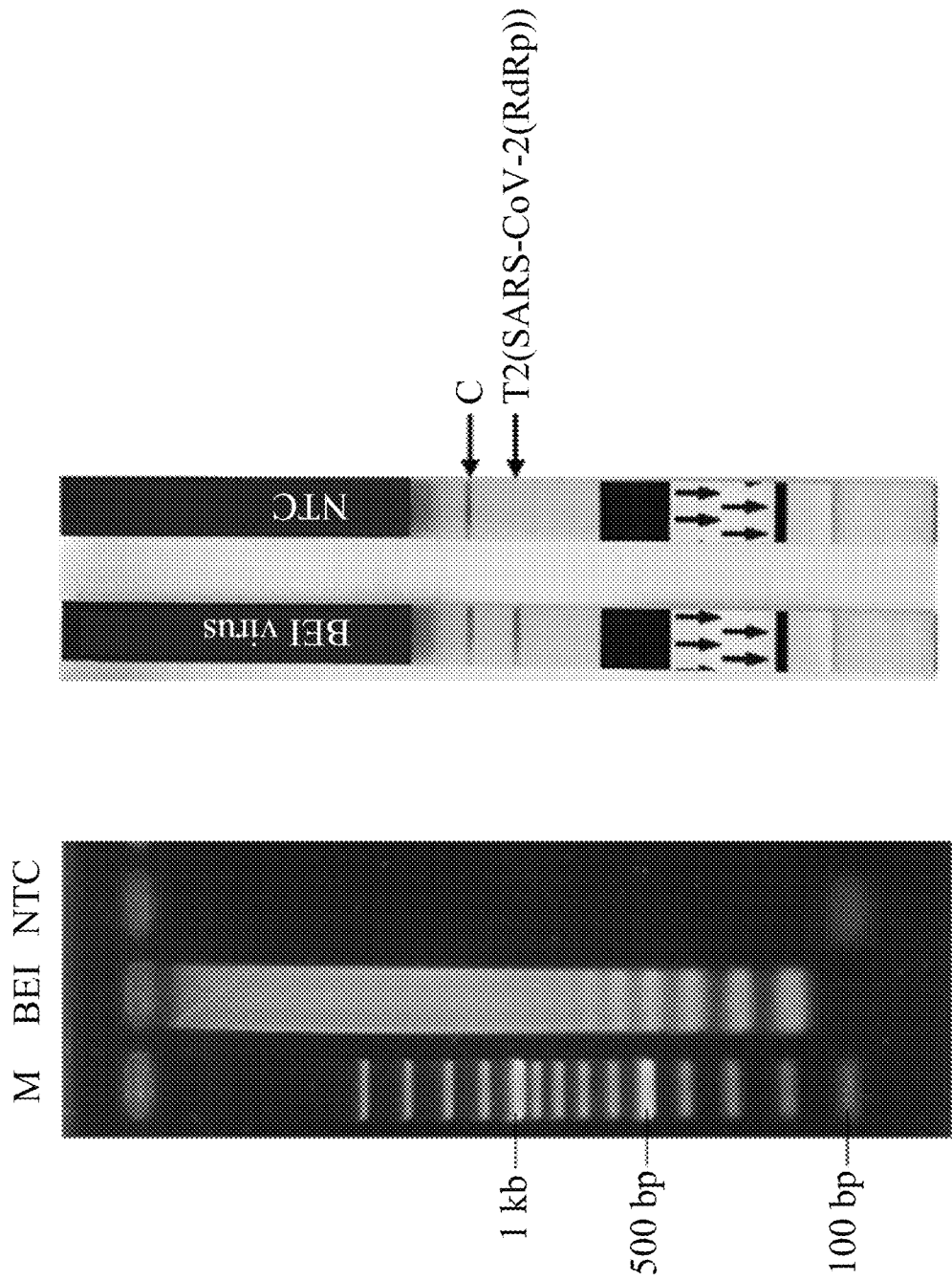
FIG. 5A shows an electrophoresis analysis result of a product obtained by performing a reverse transcription loop-mediated isothermal amplification on SARS-CoV-2 virus RNA with RdRp primer set by using Bst DNA polymerase large fragment as a polymerase. M: DNA molecular weight standard; BEI: inactivated SARS-CoV-2 virus suspension; NTC: no template control.
FIG. 5B shows a lateral flow immunoassay result of a product obtained by performing a reverse transcription loop-mediated isothermal amplification on SARS-CoV-2 virus RNA with RdRp primer set by using Bst DNA polymerase large fragment as a polymerase. M: DNA molecular weight standard; BEI: inactivated SARS-CoV-2 virus suspension; NTC: no template control; C: control line; T2: second test line.
Figure 6:
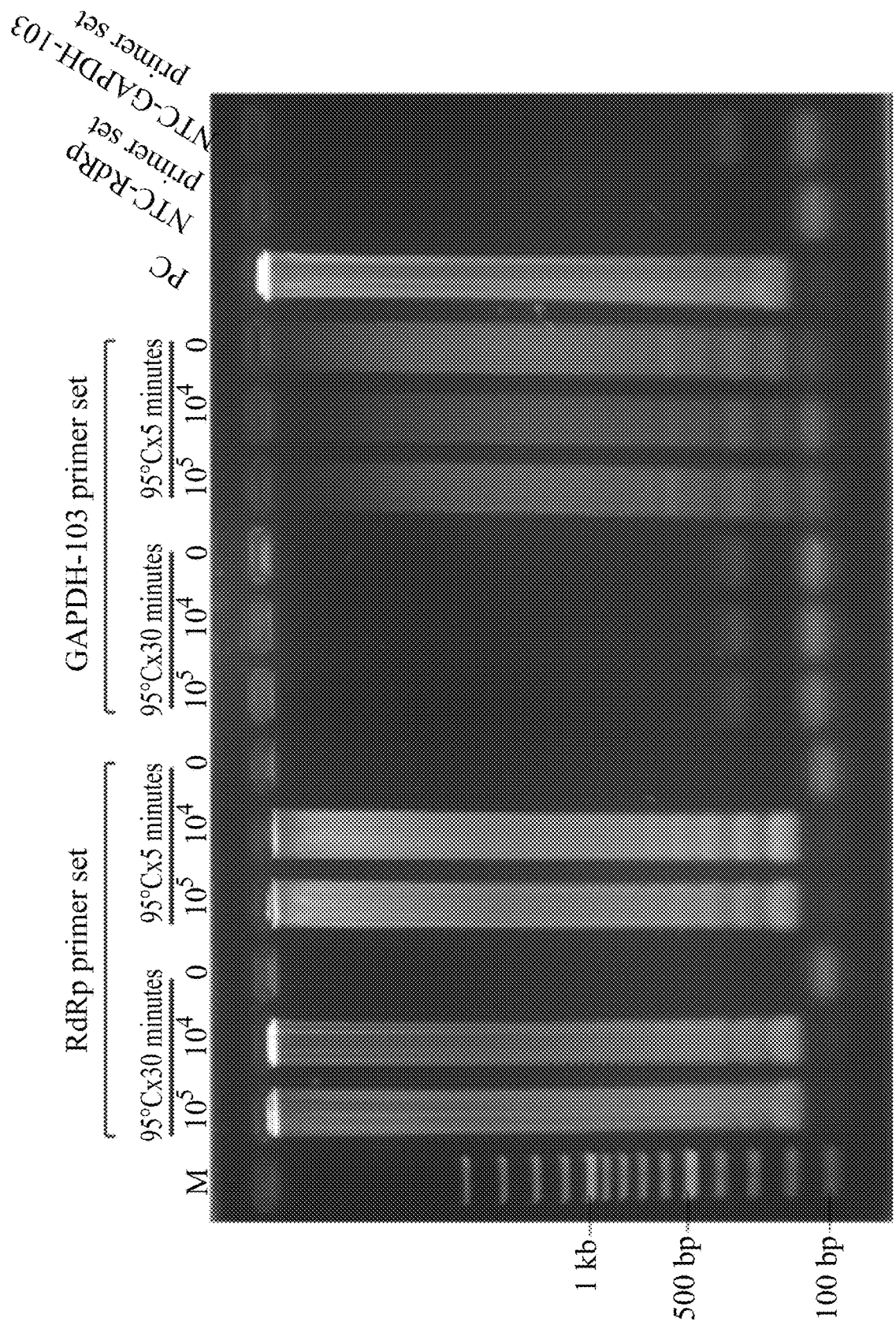
FIG. 6 shows electrophoresis analysis results of respective products obtained by directly performing respective reverse transcription loop-mediated isothermal amplifications with RdRp primer set and GAPDH-103 primer set on a sample obtained from performing a heat treatment on a SARS-CoV-2-negative saliva specimen added with inactivated SARS-CoV-2 virus suspension. M: DNA molecular weight standard; PC: positive control group; NTC-RdRp: no template control for RdRp primer set; NTC-GAPDH: no template control of GAPDH-103 primer set.
Figure 7:
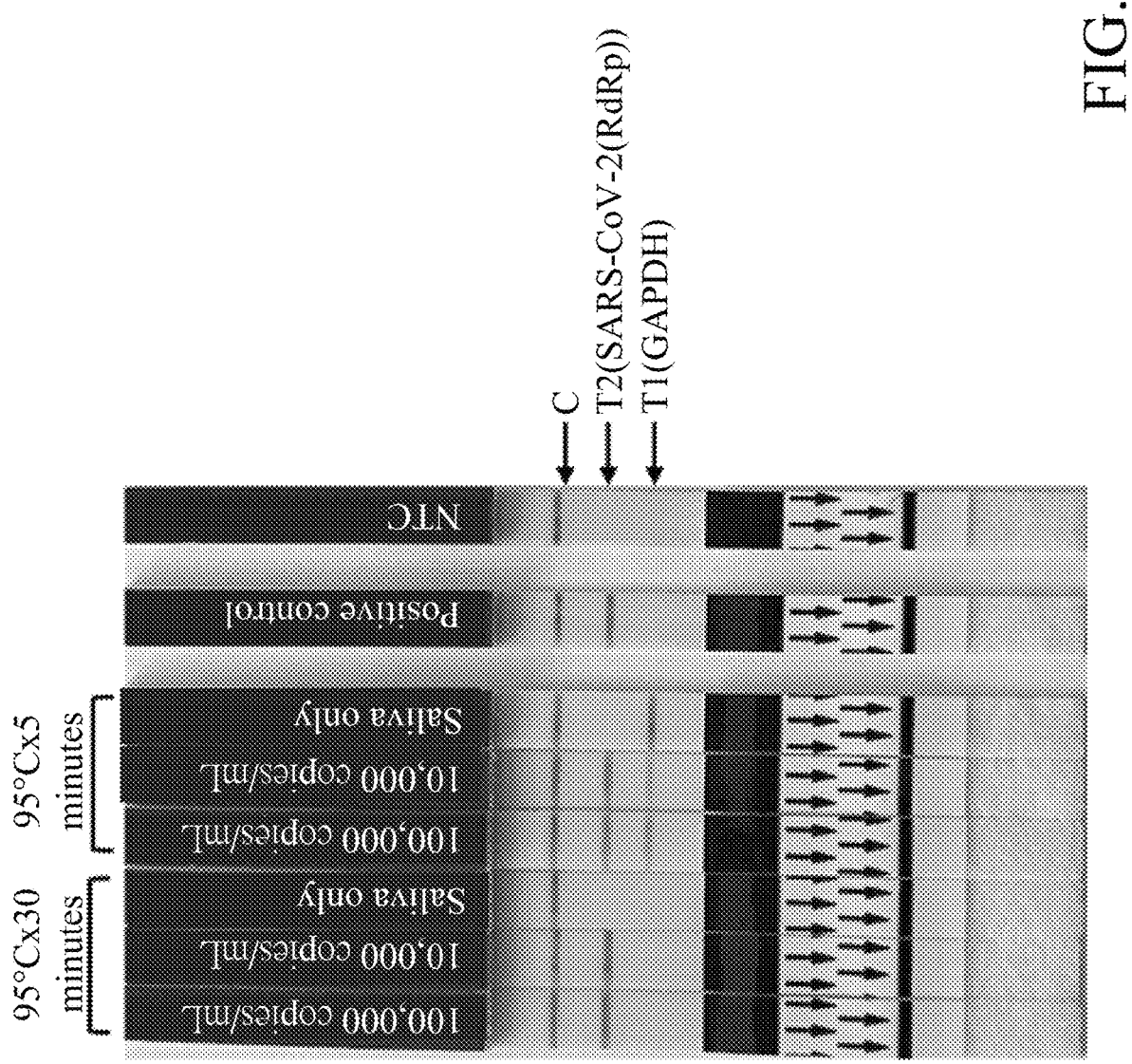
FIG. 7 shows a lateral flow immunoassay result of a mixture obtained by mixing respective products obtained by directly performing respective reverse transcription loop-mediated isothermal amplifications with RdRp primer set and GAPDH-103 primer set on a sample obtained from performing a heat treatment on a SARS-CoV-2-negative saliva specimen added with inactivated SARS-CoV-2 virus suspension. PC: positive control; NTC: no template control; C: control line; T1: first test line; T2: second test line.
Figure 8A:
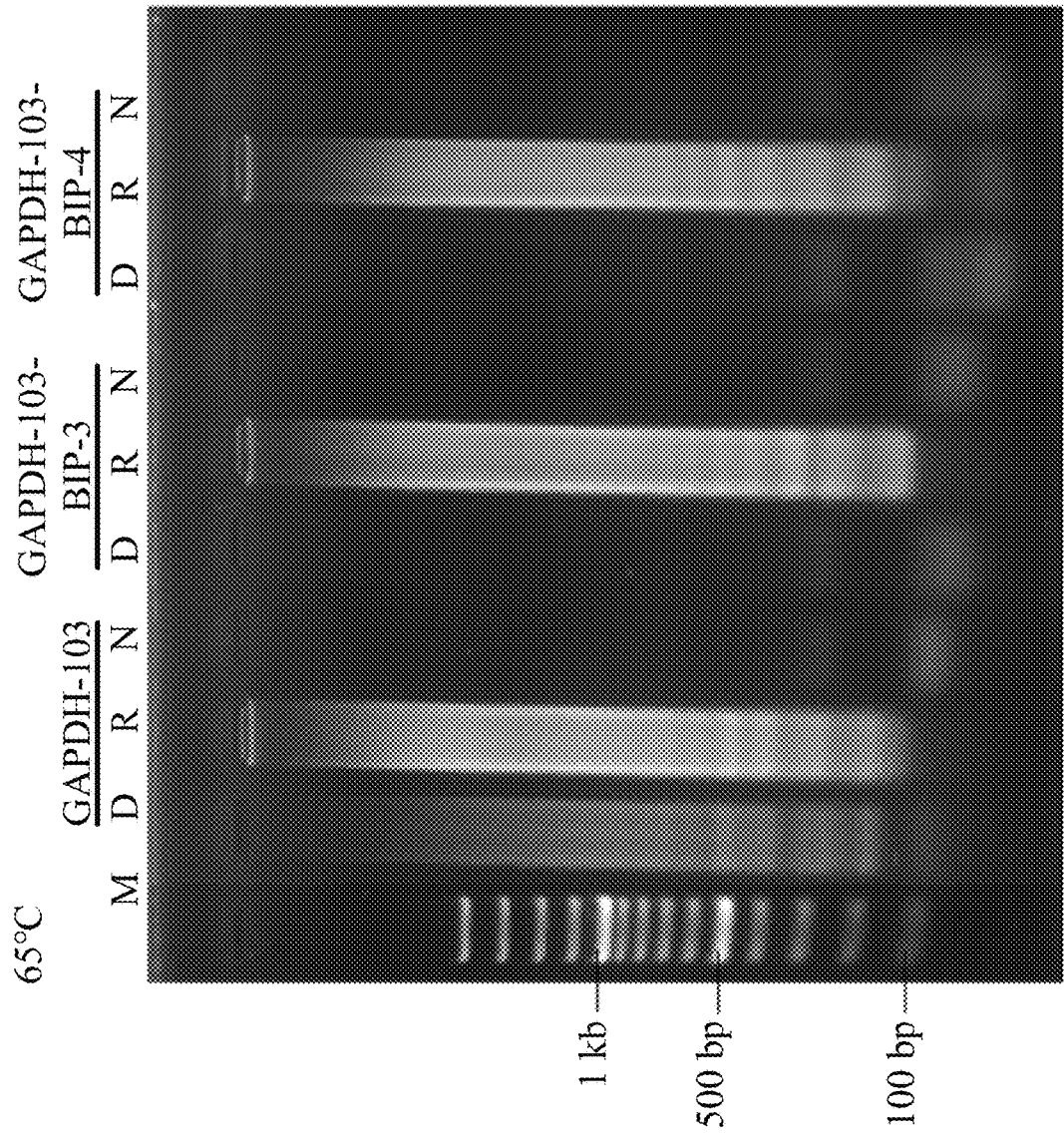
FIG. 8A shows electrophoresis analysis results of the products produced by performing loop-mediated isothermal amplifications with different GAPDH primer sets at a reaction temperature of 65° C. M: DNA molecular weight standard; D: Expi293 cell genomic DNA; R: Expi293 cell total RNA; N: no template control.
Figure 8B:
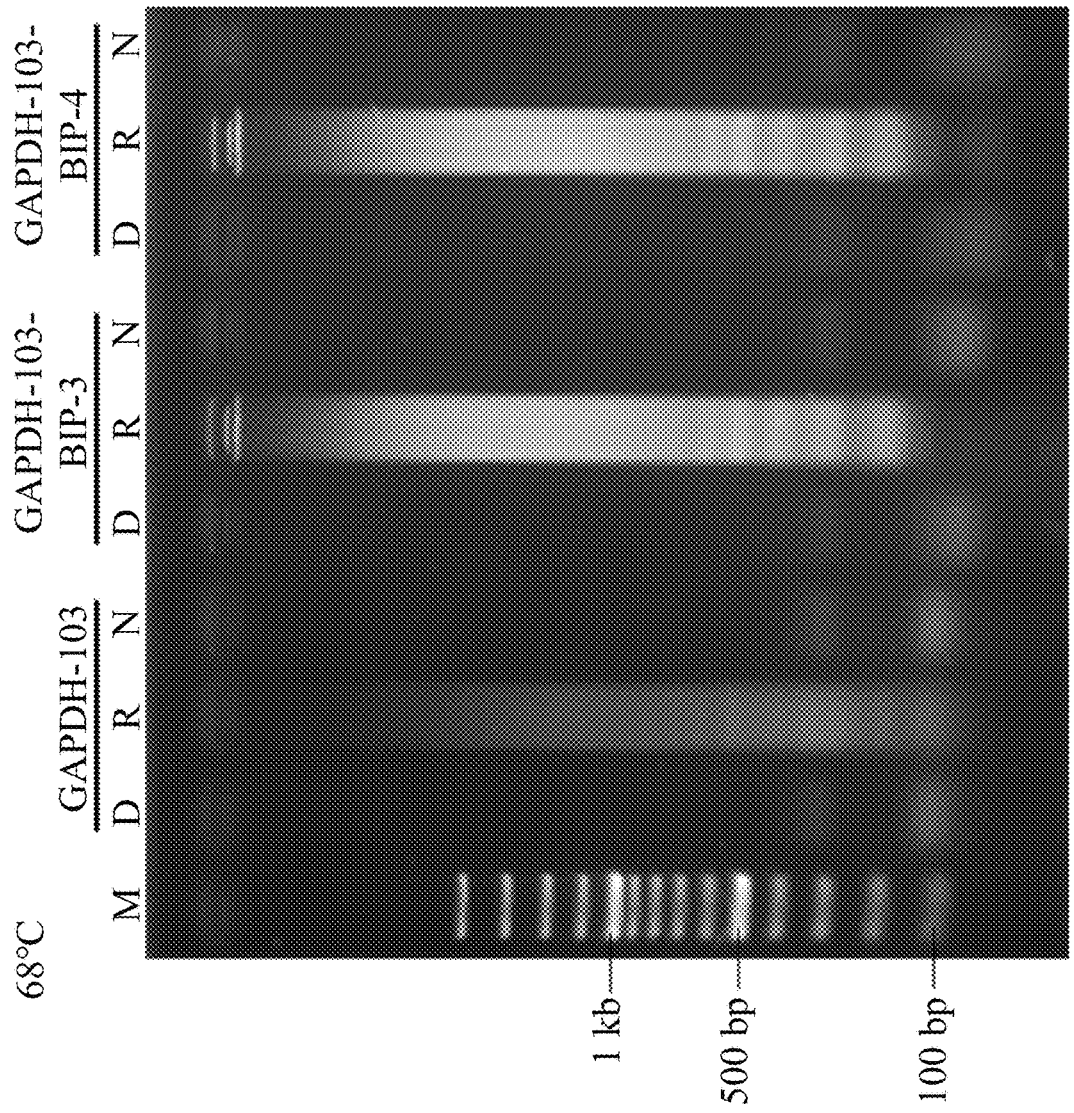
FIG. 8B shows electrophoresis analysis results of the products produced by performing loop-mediated isothermal amplifications with different GAPDH primer sets at a reaction temperature of 68° C. M: DNA molecular weight standard; D: Expi293 cell genomic DNA; R: Expi293 cell total RNA; N: no template control.
Figure 8C:
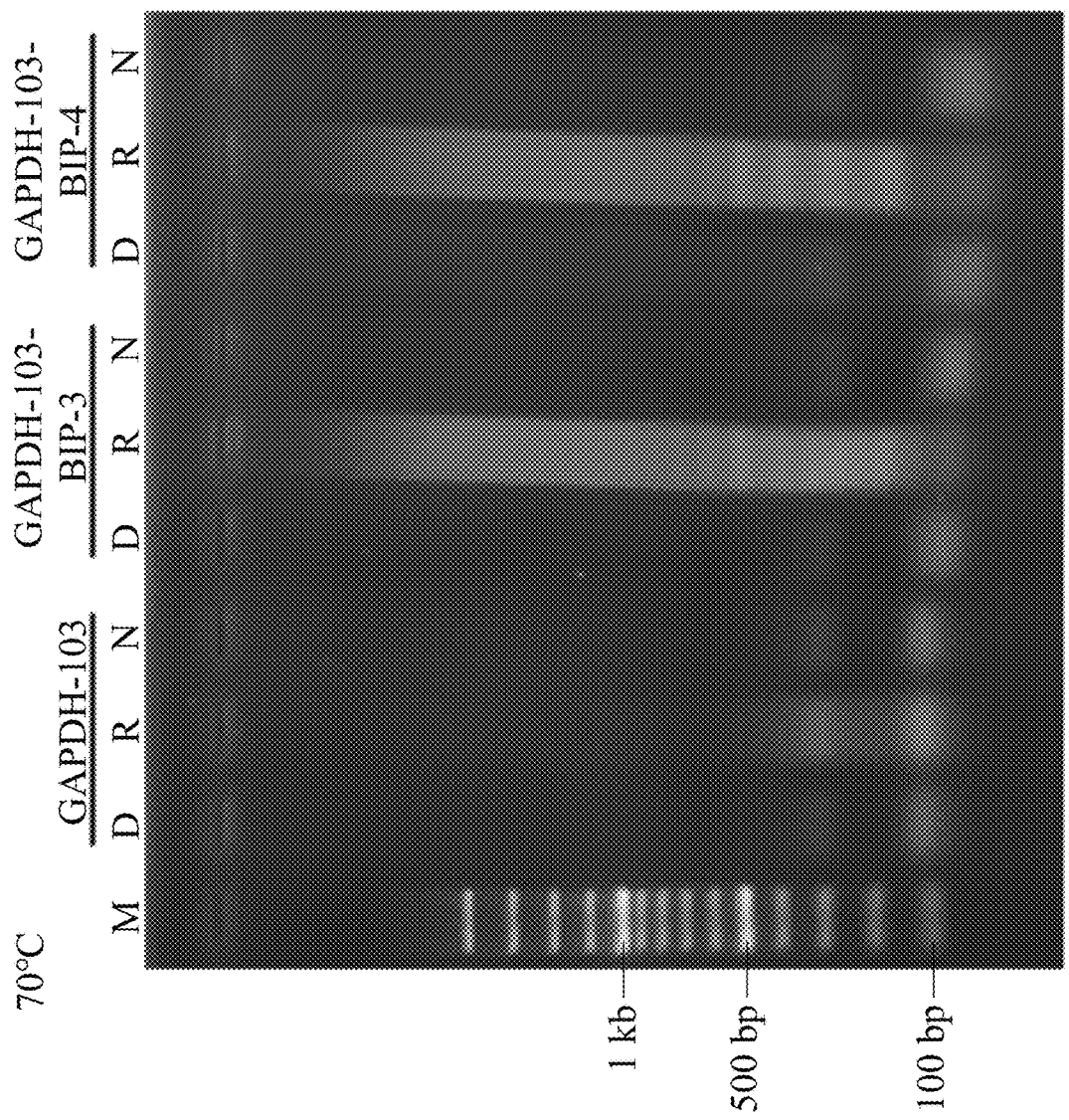
FIG. 8C shows electrophoresis analysis results of the products produced by performing loop-mediated isothermal amplifications with different GAPDH primer sets at a reaction temperature of 70° C. M: DNA molecular weight standard; D: Expi293 cell genomic DNA; R: Expi293 cell total RNA; N: no template control.
Figure 9:
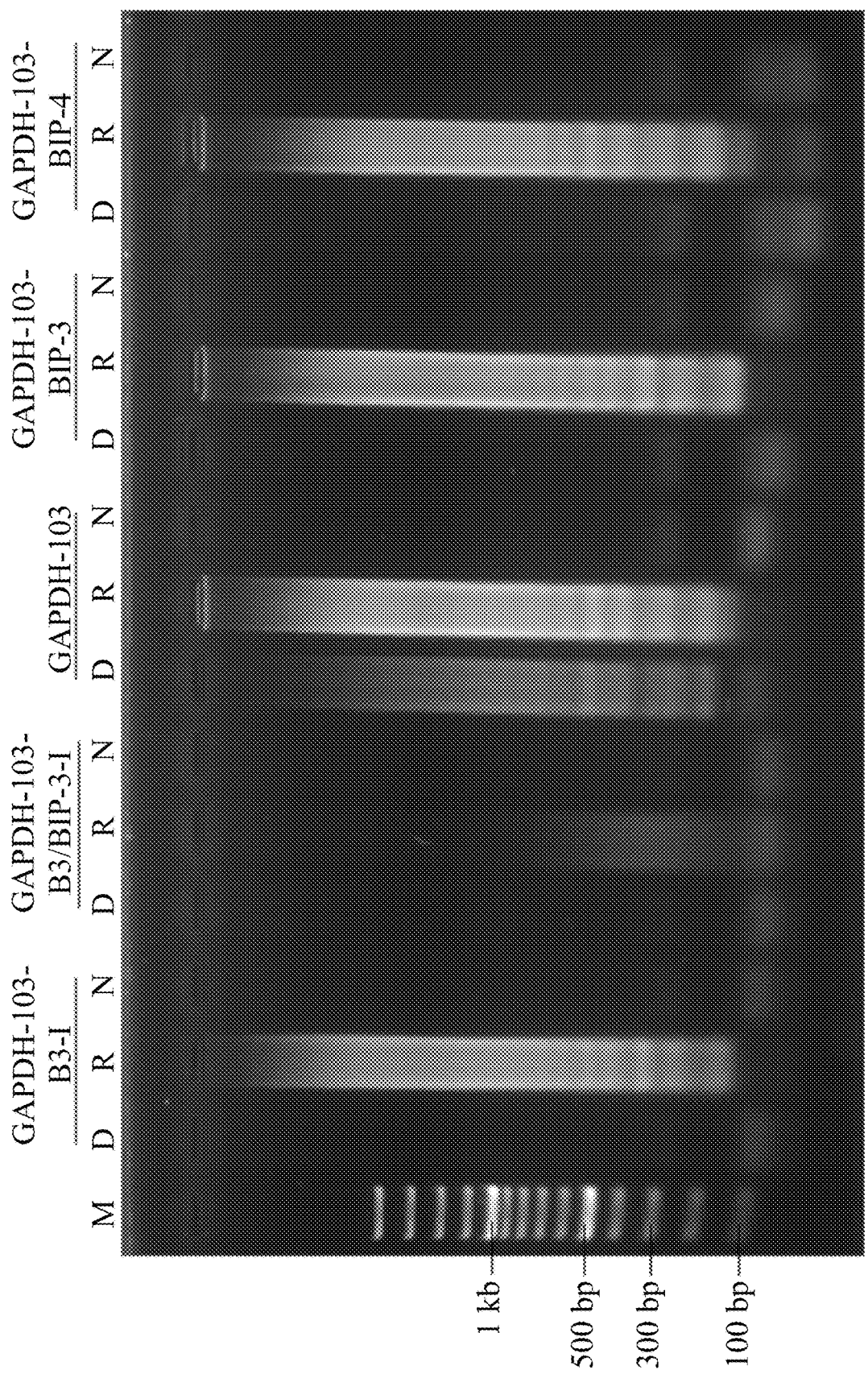
FIG. 9 shows electrophoresis analysis results of the products produced by performing loop-mediated isothermal amplifications with different modified GAPDH primer sets at a reaction temperature of 65° C. M: DNA molecular weight standard; D: Expi293 cell genomic DNA; R: Expi293 cell total RNA; N: no template control.

FIG. 4 shows that the RdRp primer set of the present disclosure can perform a loop-mediated isothermal amplification by single-stranded cDNA as a template and obtain a product.

Example 3

Detection of SARS-CoV-2 Viral RNA by Reverse Transcription Loop-Mediated Isothermal Amplification with Recombinant Bst DNA Polymerase Large Fragment as Polymerase 15,000 copies/mL of inactivated SARS-CoV-2 virus suspension (BEI Resources, Catalog No. NR-52286; Lot: 70034991) was added to a SARS-CoV-2 negative saliva specimen.

The foregoing saliva specimen containing the inactivated SARS-CoV-2 virus suspension was subjected to nucleic acid purification to obtain total RNA.

9 μL of total RNA was used as a template with the RdRp primer set and the recombinant Bst DNA polymerase large fragment to perform a reverse transcription loop-mediated isothermal amplification at 65° C. for 1 hour. The obtained products were subjected to electrophoresis analysis with 2% agarose gel and lateral flow immunoassay. The results are shown in FIG. 5A and FIG. 5B, respectively.

FIG. 5A and FIG. 5B both show that the loop-mediated isothermal amplification mentioned above can indeed obtain amplification products. Based on the experimental results, it is understood that the recombinant Bst DNA polymerase large fragment has endogenous reverse transcriptase activity, and the RdRp primer set of the present disclosure can perform a reverse transcription loop-mediated isothermal amplification at 65° C. with single-stranded RNA as a template by using this recombinant Bst DNA polymerase large fragment.

Example 4

Detection of SARS-CoV-2 Virus in Heat-Treated Saliva Directly by Reverse Transcription Loop-Mediated Isothermal Amplification Inactivated SARS-CoV-2 virus was added to 50 μL of a SARS-CoV-2 negative saliva specimen at a final concentration of 10,000 copies/mL or 100,000 copies/mL. The sample mentioned above and a negative saliva specimen without virus addition were treated in the following two ways:

(1) 50 μL DPBS and 2× RNAsecure were added to the sample mentioned above, and heated at 95° C. for 30 minutes;

(2) Proteinase K and 2× RNAsecure were added to the sample mentioned above, and heated at 95° C. for 5 minutes.

After the two treatment ways, 9 μL of the heated supernatant was used as a nucleic acid template and mixed with RdRp primer set or GAPDH-103 primer set to perform a reverse transcription loop-mediated isothermal amplification, and the obtained product was subjected to electrophoresis analysis with 2% agarose gel. The results are shown in FIG. 6.

The products respectively amplified from RdRp and GAPDH at the same virus concentration were mixed, and subjected to a lateral flow immunoassay. The results are shown in FIG. 7.

According to the experimental results, it is understood that by the RdRp primer set or GAPDH primer set of the present disclosure, a saliva specimen can be directly subjected to a reverse transcription loop-mediated isothermal amplification with RT/Bst mix as a polymerase without undergoing nucleic acid purification steps, to obtain amplification products of the RdRp RNA of SARS-CoV-2 virus and human GAPDH gene.

Example 5

RT-LAMP Reaction Temperature Test for GAPDH Primer Set

Expi293 cells were harvested. A part of the cells were extracted with genomic DNA using QIAamp genomic DNA kits (Qiagen), and then treated with RNase A/T1 (Thermo Scientific). The other part of the cells were extracted with Direct-zol RNA Miniprep (Zymo Research) for total RNA, and digested with DNase I on the column.

The purified genomic DNA and total RNA were used as nucleic acid templates for testing the GAPDH primer sets. The reaction temperatures of the reverse transcription loop-mediated isothermal amplifications were set to 65° C., 68° C. and 70° C. for testing. When the reaction temperature was set to 65° C., GAPDH-103 primer set could amplify the GAPDH gene in genomic DNA and total RNA at the same time while GAPDH-103-BIP-3 primer set and GAPDH-103-BIP-4 primer set can only amplify GAPDH gene in total RNA (FIG. 8A).

When the reaction temperature was increased to 68° C., GAPDH-103-BIP-3 primer set and GAPDH-103-BIP-4 primer set still retained the property only amplifying the GAPDH gene in total RNA. For GAPDH-103 primer set, increasing the temperature could increase the discrimination between genomic DNA and total RNA for this primer set (FIG. 8B).

When the reaction temperature was increased to 70° C., GAPDH-103 primer set only slightly amplified the GAPDH gene in total RNA while GAPDH-103-BIP-3 primer set and GAPDH-103-BIP-4 primer set still had the property of only amplifying the GAPDH gene in total RNA (FIG. 8C).

The experimental results mentioned above show that compared to GAPDH-103 primer set, GAPDH-103-BIP-3 primer set and GAPDH-103-BIP-4 primer set have a wider temperature tolerance.

Example 6

Amplification Test for GAPDH Primer Set:

Expi293 cells were harvested. A part of the cells were extracted with genomic DNA using QIAamp genomic DNA kits (Qiagen), and then treated with RNase A/T1 (Thermo Scientific). The other part of the cells were extracted with Direct-zol RNA Miniprep (Zymo Research) for total RNA, and digested with DNase I on the column.

The purified genomic DNA and total RNA were used as nucleic acid templates for testing the GAPDH primer sets. The reaction temperature of the reverse transcription loop-mediated isothermal amplification was set to 65° C.

Substitution of five nucleic acids on B3 in the GAPDH-103 primer set with inosine (shown as GAPDH-103-B3-I) could allow the primer set amplify the GAPDH gene by only using total RNA as a template (FIG. 9). This result shows that after the primer set for human GAPDH gene is modified by inosine, it can be not interfered by the genomic DNA sequence and only perform the reverse transcription loop-mediated isothermal amplification on mRNA.

In addition, a partial sequence of BIP in the GAPDH-103 primer set was shifted to form two primer sets of GAPDH-103-BIP-3 and GAPDH-103-BIP-4. The experimental results show that the two primer sets only use total RNA as a template to specifically amplify the GAPDH gene.

Example 7

Detection of RdRp and GAPDH RNA in Heat-Treated Samples:

Inactivated SARS-CoV-2 virus was added to 50 μL of a SARS-CoV-2 negative saliva specimen at a final concentration of 10,000 copies/mL or 100,000 copies/mL. The sample mentioned above and a negative saliva specimen without virus addition were heated at 95° C. for 5 minutes to obtain heat-treated samples.

9 μL of the heated sample was used as a template and separately mixed with RdRp primer set and GAPDH primer set with inosine substitution (GAPDH-103-B3-I) to perform reverse transcription loop-mediated isothermal amplifications at 65° C., and the obtained products were subjected to electrophoresis analysis with 2% agarose gel. The results are shown in FIG. 10A and FIG. 10B, respectively.

A mixture obtained by mixing the two products obtained by performing reverse transcription loop-mediated isothermal amplifications on the heat-treated samples mentioned above respectively with the RdRp primer set and the GAPDH primer set (GAPDH-103-B3-I) was subjected to a lateral flow immunoassay. The results are shown in FIG. 10C.

The experimental results show that by the RdRp primer set or GAPDH primer set of the present disclosure, a saliva specimen can be directly subjected to a reverse transcription loop-mediated isothermal amplification with RT/Bst mix as a polymerase without undergoing nucleic acid purification steps, to obtain amplification products of the RdRp RNA of SARS-CoV-2 virus and human GAPDH gene, and the amplification products can be confirmed by electrophoresis analysis and lateral flow immunoassay. Both the RdRp primer set and the GAPDH primer set with inosine substitutions (GAPDH-103-B3-I) can be used in heat-treated samples, and through the GAPDH amplification product, it can be confirmed that the sample RNA can be released during the heat treatment.

Example 8

Reverse transcription loop-mediated isothermal amplification by reverse transcriptase with RNase H activity:

An in vitro-transcribed RdRp RNA was used as a template and mixed with RocketScript reverse transcriptase (Bioneer) with RNase H activity to reverse transcribe the RNA into cDNA, and then subjected a loop-mediated isothermal amplification.

Figures 11A, 11B:
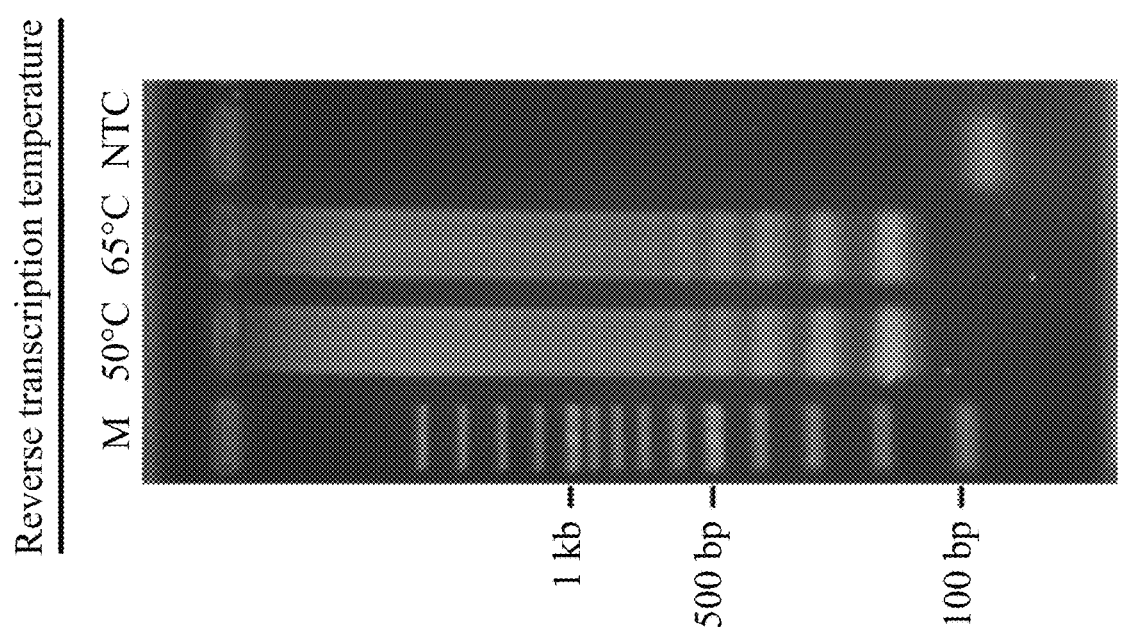
FIG. 11A shows electrophoresis analysis results of products obtained by performing reverse transcriptions with a reverse transcriptase with RNase H activity at different temperatures and then performing loop-mediated isothermal amplifications with recombinant Bst DNA polymerase (two-step reaction) on in vitro transcribed RdRp RNA. M: DNA molecular weight standard; NTC: no template control.
FIG. 11B shows lateral flow immunoassay result of products obtained by performing reverse transcriptions with a reverse transcriptase with RNase H activity at different temperatures and then performing loop-mediated isothermal amplifications with recombinant Bst DNA polymerase (two-step reaction) on in vitro transcribed RdRp RNA. C: control line; T2: second test line.

In the two-step reverse transcription loop-mediated isothermal amplification, the in vitro-transcribed RdRp RNA was added at a final concentration of $6\times10^6$ copies/mL, and separately reacted at 50° C. and 65° C. for 15 minutes, and then heated at 95° C. for 5 minutes. 2 μL of the reverse transcription product was mixed with a recombinant Bst DNA polymerase large fragment and the RdRp primer set, and subjected loop-mediated isothermal amplification at 65° C. for 1 hour. The obtained products were subjected to electrophoresis analysis with 2% agarose gel and lateral flow immunoassay. The results are shown in FIG. 11A and FIG. 11B, respectively.

Figures 12A, 12B:
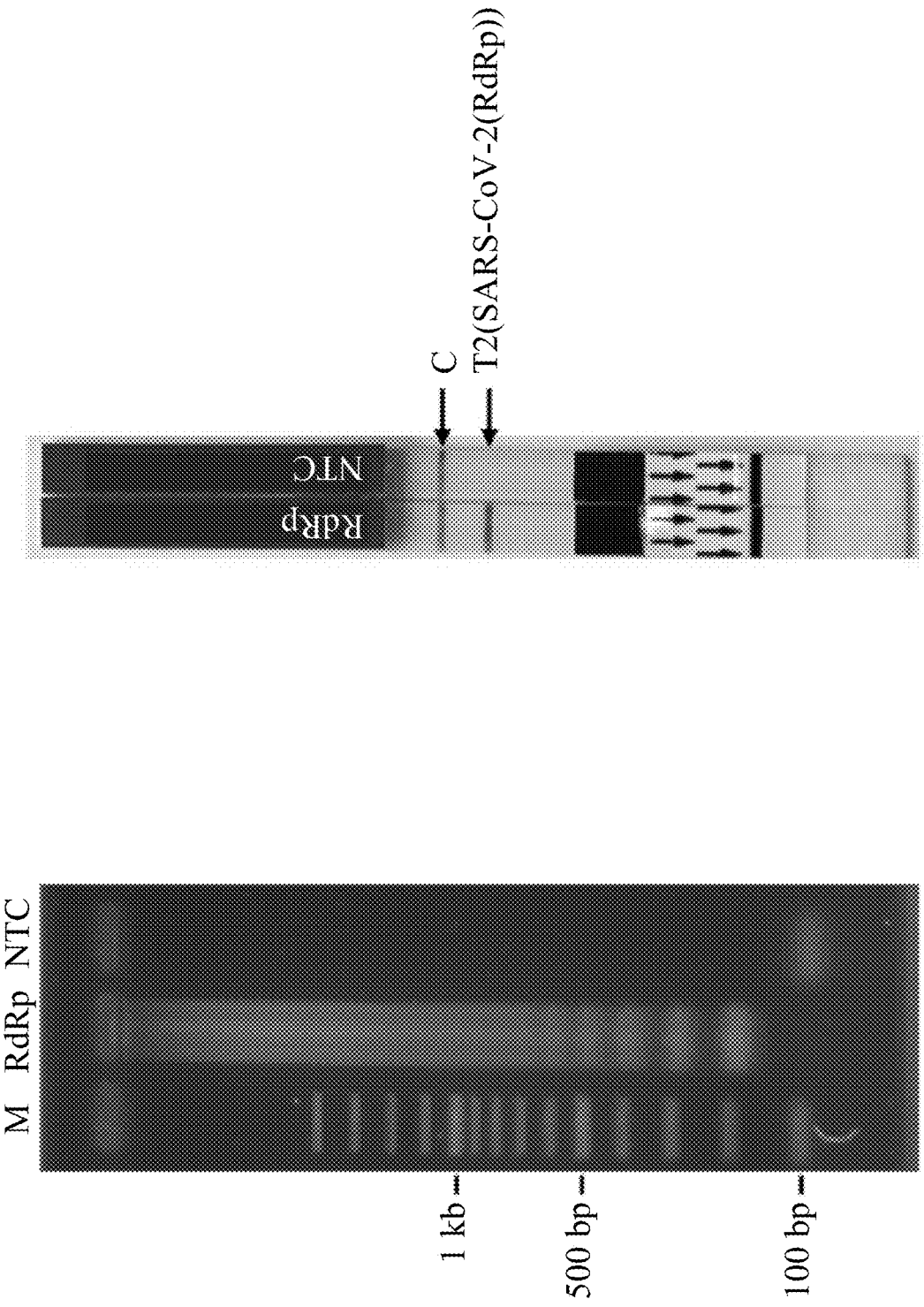
FIG. 12A shows an electrophoresis analysis result of a product obtained by performing a reverse transcription loop-mediated isothermal amplification with a reverse transcriptase with RNase H activity and recombinant Bst DNA polymerase (one-step reaction) at 65° C. on in vitro transcribed RdRp RNA. M: DNA molecular weight standard; NTC: no template control.
FIG. 12B shows lateral flow immunoassay result of products obtained by performing reverse transcriptions with a reverse transcriptase with RNase H activity and recombinant Bst DNA polymerase (one-step reaction) at 65° C. on in vitro transcribed RdRp RNA. C: control line; T2: second test line.

In the one-step reverse transcription loop-mediated isothermal amplification, the in vitro-transcribed RdRp RNA ($1\times10^4$ copies) was mixed with the RdRp primer set, RocketScript Reverse Transcriptase and a recombinant Bst DNA polymerase large fragment and reacted at 65° C. for 1 hour. The obtained products were subjected to electrophoresis analysis with 2% agarose gel and lateral flow immunoassay. The results are shown in FIG. 12A and FIG. 12B, respectively.

Based on the experimental results, it is understood that the RdRp primer set of the present disclosure can perform reverse transcription with single-stranded RNA as a template by using a reverse transcriptase with RNase H activity.

Example 9

Comparison of Primer Sets

The primer set of the present disclosure, GAPDH-103 primer set, and the primer sets not designed in the design region of the present disclosure, GAPDH-5 primer set and GAPDH-90 primer set, were respectively subjected to reverse transcription loop-mediated isothermal amplifications. The designed region and sequences thereof for GAPDH-5 primer set and GAPDH-90 primer set are shown in Table 5.

Expi293 cells were harvested, and Expi293 cells were extracted with Direct-zol RNA Miniprep (Zymo Research) for total RNA. Afterwards, the extracted total RNA was digested with DNase I on the column. A SARS-CoV-2-negative saliva sample was extracted with QIAamp Viral RNA Mini Kit to obtain the total RNA of the SARS-CoV-2-negative saliva.

Figure 13:
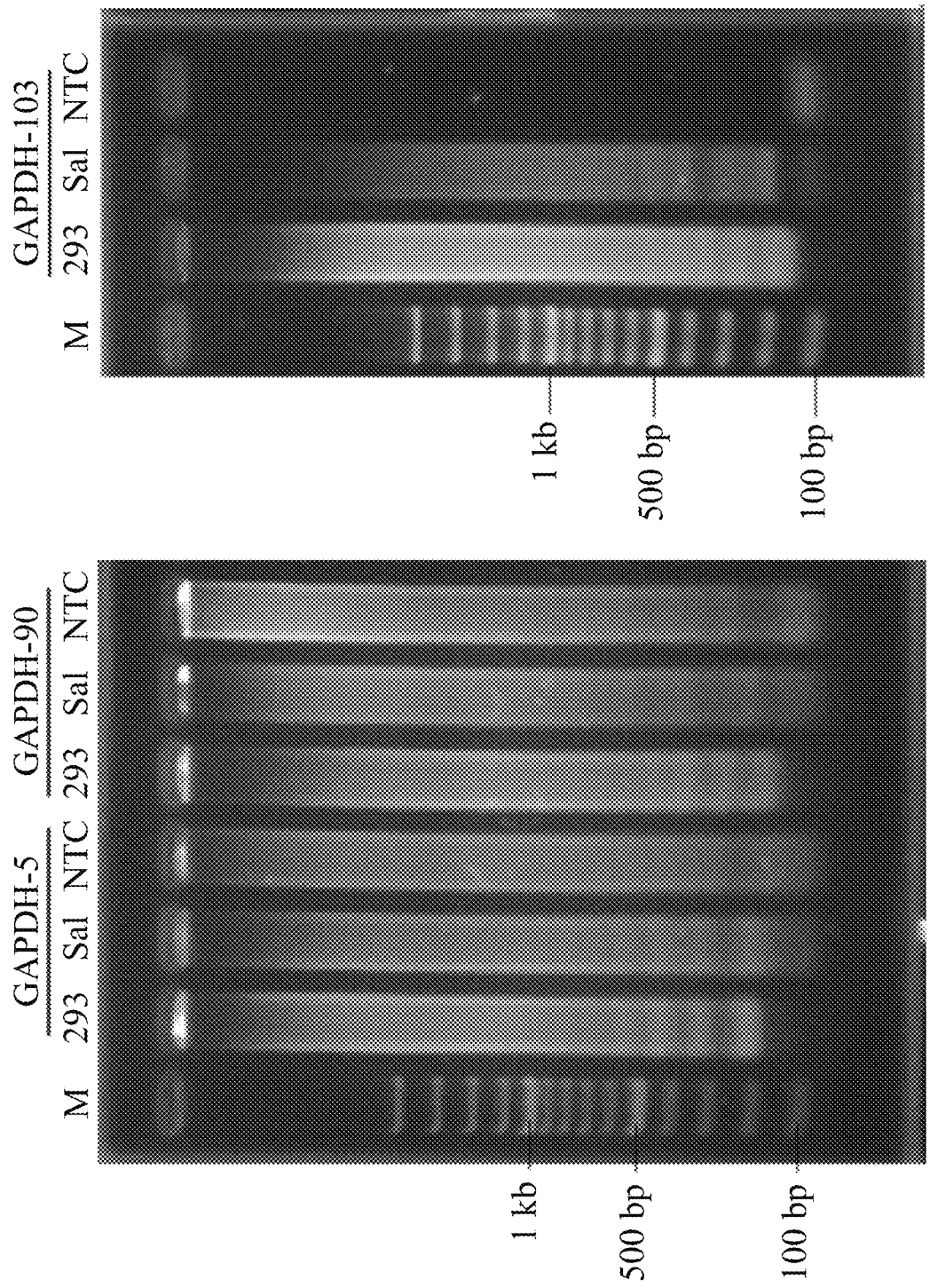
FIG. 13 shows electrophoresis analysis results of respective products obtained by performing respective reverse transcription loop-mediated isothermal amplifications with GAPDH-103 primer set of the present disclosure and primer set GAPDH-5 and primer set GAPDH-90 which are not designed in the design region of the present disclosure. M: DNA molecular weight standard; 293: total RNA of Expi293 cells; Sal: total RNA of SARS-CoV-2-negative saliva; NTC: no template control.

The total RNA of Expi293 cells was taken 9 μL as a nucleic acid template, and added to the tubes respectively containing the GAPDH-5 primer set, GAPDH-90 primer set and GAPDH-103 primer set, and after mixed with RT/Bst mix, placed at 65° C. to perform reverse transcription loop-mediated isothermal amplifications for 1 hour. The total RNA extracted from the SARS-CoV-2-negative saliva mentioned above was taken 9 μL as a nucleic acid template, and added to the tubes respectively containing the GAPDH-5 primer set, GAPDH-90 primer set and GAPDH-103 primer set, and after mixed with RT/Bst mix, placed at 65° C. to perform reverse transcription loop-mediated isothermal amplifications for 1 hour. The obtained products were subjected to electrophoresis analysis with 2% agarose gel, and the results are shown in FIG. 13.

TABLE 5

Design of primer set based on the nucleotide sequence of SEQ ID NO. 11
Primer set GAPDH-5

| Selected regions and designed primers | 5' end position | 3' end position | Length | Sequence |
|---|---|---|---|---|
| F3 region (Forward outer primer) | 268 | 287 | 20 | GCCAAGGTCATCCATGACAA (SEQ ID NO. 33) |
| F2 region | 291 | 310 | 20 | TGGTATCGTGGAAGGACTCA (SEQ ID NO. 37) |
| F1c region | 333 | 353 | 21 | TCCACAGTCTTCTGGGTGGCA (SEQ ID NO. 36) |

TABLE 5-continued

| | | | | |
|---|---|---|---|---|
| B1c region | 387 | 408 | 22 | CGGGGCTCTCCAGAACATC ATC (SEQ ID NO. 38) |
| B2 region | 433 | 450 | 18 | GATGACCTTGCCCACAGC (SEQ ID NO. 39) |
| B3 region (Backward outer primer) | 452 | 469 | 18 | GCTTCCCGTTCAGCTCAG (SEQ ID NO. 35) |
| FIP (Forward inner primer) | | | 47 | TCCACAGTCTTCTGGGTGG CATTTTTTGGTATCGTGG AAGGACTCA (SEQ ID NO. 32) |
| BIP (Backward inner primer) | | | 46 | CGGGGCTCTCCAGAACATC ATCTTTTTTGATGACCTTG CCCACAGC (SEQ ID NO. 34) |

Primer set GAPDH-90

| Selected regions and designed primers | 5' end position | 3' end position | Length | Sequence |
|---|---|---|---|---|
| F3 region (Forward outer primer) | 291 | 310 | 20 | TGGTATCGTGGAAGGACTC A (SEQ ID NO. 37) |
| F2 region | 315 | 333 | 19 | CACAGTCCATGCCATCACT (SEQ ID NO. 43) |
| F1c region | 362 | 381 | 20 | ATCACGCCACAGTTTCCCG G (SEQ ID NO. 42) |
| B1c region | 387 | 408 | 22 | CGGGGCTCTCCAGAACATC ATC (SEQ ID NO. 38) |
| B2 region | 433 | 450 | 18 | GATGACCTTGCCCACAGC (SEQ ID NO. 39) |
| B3 region (Backward outer primer) | 456 | 473 | 18 | GTGAGCTTCCCGTTCAGC (SEQ ID NO. 41) |
| FIP (Forward inner primer) | | | 45 | ATCACGCCACAGTTTCCCG GTTTTTTCACAGTCCATGC CATCACT (SEQ ID NO. 40) |
| BIP (Backward inner primer) | | | 46 | CGGGGCTCTCCAGAACATC ATCTTTTTTGATGACCTTG CCCACAGC (SEQ ID NO. 34) |

The results are shown in FIG. 13.

The experimental results show that, compared to GAPDH-103 primer set, GAPDH-5 primer set and GAPDH-90 primer set also produce amplification products in the no template control, and thus cannot be used as a primer set for detecting GAPDH.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A GAPDH nucleic acid detection kit, comprising:
a primer set for detecting GAPDH nucleic acids, comprising:
a forward inner primer for GAPDH nucleic acids;
a forward outer primer for GAPDH nucleic acids;
a backward inner primer for GAPDH nucleic acids; and
a backward outer primer for GAPDH nucleic acids,
wherein
the forward inner primer for GAPDH nucleic acids consists of a first segment and a second segment, and the 3' end of the first segment is connected to the 5' end of the second segment, or the forward inner primer for GAPDH nucleic acids consists of a first segment, a first linker and a second segment, and the 3' end of the first segment is connected to the 5' end of the first linker, and the 3' end of the first linker is connected to the 5' end of the second segment, wherein
the first segment has 10-30 nucleotides and consists of a complementary strand of a first sequence section, and the first sequence section is located between position 134 and position 175 of the nucleotide sequence of SEQ ID NO. 1, and
the second segment has 10-30 nucleotides and consists of a second sequence section, and the second sequence section is located between position 77 and position 115 of the nucleotide sequence of SEQ ID NO. 1, and
the first linker consists of 1-6 thymines or peptide nucleic acids (PNAs),
the forward outer primer for GAPDH nucleic acids has 10-30 nucleotides and consists of a third sequence section, and the third sequence section is located between position 42 and position 79 of the nucleotide sequence of SEQ ID NO. 1,
the backward inner primer for GAPDH nucleic acids consists of a third segment and a fourth segment, and the 3' end of the third segment is connected to the 5' end of the fourth segment, or the backward inner primer for GAPDH nucleic acids consists of a third segment, a second linker and a fourth segment, and the 3' end of the third segment is connected to the 5' end of the second linker, and the 3' end of the second linker is connected to the 5' end of the fourth segment,
wherein
the third segment has 10-30 nucleotides and consists of a fourth sequence section, and the fourth sequence section is located between position 156 and position 207 of the nucleotide sequence of SEQ ID NO. 1, and
the fourth segment has 10-30 nucleotides and consists of a complementary strand of a fifth sequence section, and the fifth sequence section is located between position 211 and position 250 of the nucleotide sequence of SEQ ID NO. 1, and
the second linker consists of 1-6 thymines or peptide nucleic acids,
the backward outer primer for GAPDH nucleic acids has 10-30 nucleotides and consists of a complementary strand of a sixth sequence section, and the sixth sequence section is located between position 238 and position 275 of the nucleotide sequence of SEQ ID NO. 1,
wherein the GAPDH nucleic acid detection kit is used in a loop-mediated isothermal amplification (LAMP), and the loop-mediated isothermal amplification comprises a standard loop-mediated isothermal amplification or a reverse transcription loop-mediated isothermal amplification (RT-LAMP).

2. The GAPDH nucleic acid detection kit as claimed in claim 1, wherein
the sequence of the forward inner primer for GAPDH nucleic acids comprises the nucleotide sequence of SEQ ID NO. 2;
the sequence of the forward outer primer for GAPDH nucleic acids comprises the nucleotide sequence of SEQ ID NO. 3;
the sequence of the backward inner primer for GAPDH nucleic acids comprises the nucleotide sequence of SEQ ID NO. 4, the nucleotide sequence of SEQ ID NO. 6 or the nucleotide sequence of SEQ ID NO. 7, and
the sequence of the backward outer primer for GAPDH nucleic acids comprises the nucleotide sequence of SEQ ID NO. 5.

3. The GAPDH nucleic acid detection kit as claimed in claim 1, wherein for at least one of the forward inner primer for GAPDH nucleic acids, the forward outer primer for GAPDH nucleic acids, the backward inner primer for GAPDH nucleic acids and the backward outer primer for GAPDH nucleic acids, 1 to 10 nucleotides counted from any one position as a start point between position 4 and position 14 from the 3' end thereof is/are independently substituted by one of the following nucleotides:
inosine (I);
guanine (G); and
uracil (U).

4. The GAPDH nucleic acid detection kit as claimed in claim 3, wherein the sequence of backward inner primer for GAPDH nucleic acids comprises the nucleotide sequence of SEQ ID NO. 8 and/or the sequence of the backward outer primer for GAPDH nucleic acids comprises the nucleotide sequence of SEQ ID NO. 9.

5. The GAPDH nucleic acid detection kit as claimed in claim 3, wherein
the sequence of the forward inner primer for GAPDH nucleic acids comprises the nucleotide sequence of SEQ ID NO. 2;
the sequence of the forward outer primer for GAPDH nucleic acids comprises the nucleotide sequence of SEQ ID NO. 3;
the sequence of the backward inner primer for GAPDH nucleic acids comprises the nucleotide sequence of SEQ ID NO. 4 or the nucleotide sequence of SEQ ID NO. 8, and
the sequence of the backward outer primer for GAPDH nucleic acids comprises the nucleotide sequence of SEQ ID NO. 9.

6. The GAPDH nucleic acid detection kit as claimed in claim 1, wherein the 5' end of the backward inner primer for GAPDH nucleic acids is labeled with a first label, the 5' end of the forward inner primer for GAPDH nucleic acids is labeled with a second label, and the first label and the second label are different, and wherein the first label comprises biotin, avidin, streptavidin (SA), digoxigenin or fluorescein, and the second label comprises biotin, avidin, streptavidin, digoxigenin or fluorescein.

7. The GAPDH nucleic acid detection kit as claimed in claim 6, further comprising a lateral flow immunoassay test strip which, according to a flow direction of an analyte, sequentially comprises an analyte addition area, a binding area, a GAPDH detection area and a test strip control area, wherein
the binding area has a first binding particle which has a first binding molecule and a particle linked to the first binding molecule, wherein the first binding molecule is capable of binding the first label,
the GAPDH detection area is immobilized with a second binding molecule which is capable of binding to the second label, and
the test strip control area is immobilized with a third binding molecule which is capable of binding the first binding molecule of the first binding particle, wherein the third binding molecule and the first label are the same or different.

8. The GAPDH nucleic acid detection kit as claimed in claim 1, further comprising a polymerase and/or nucleotide substrate, wherein the polymerase has a function of reverse transcriptase, and the polymerase is a Bst DNA polymerase and the sequence thereof comprises the amino acid sequence of SEQ ID NO. 10.

9. A target nucleic acid detection kit, comprising:
a primer set for detecting GAPDH nucleic acids, comprising:
a forward inner primer for GAPDH nucleic acids;
a forward outer primer for GAPDH nucleic acids;
a backward inner primer for GAPDH nucleic acids; and
a backward outer primer for GAPDH nucleic acids,
wherein
the forward inner primer for GAPDH nucleic acids consists of a first segment and a second segment, and the 3' end of the first segment is connected to the 5' end of the second segment, or the forward inner primer for GAPDH nucleic acids consists of a first segment, a first linker and a second segment, and the 3' end of the first segment is connected to the 5' end of the first linker, and the 3' end of the first linker is connected to the 5' end of the second segment,
wherein
the first segment has 10-30 nucleotides and consists of a complementary strand of a first sequence section, and the first sequence section is located between position 134 and position 175 of the nucleotide sequence of SEQ ID NO. 1, and
the second segment has 10-30 nucleotides and consists of a second sequence section, and the second sequence section is located between position 77 and position 115 of the nucleotide sequence of SEQ ID NO. 1, and
the first linker consists of 1-6 thymines or peptide nucleic acids,
the forward outer primer for GAPDH nucleic acids has 10-30 nucleotides and consists of a third sequence section, and the third sequence section is located between position 42 and position 79 of the nucleotide sequence of SEQ ID NO. 1,
the backward inner primer for GAPDH nucleic acids consists of a third segment and a fourth segment, and the 3' end of the third segment is connected to the 5' end of the fourth segment, or the backward inner primer for GAPDH nucleic acids consists of a third segment, a second linker and a fourth segment, and the 3' end of the third segment is connected to the 5' end of the second linker, and the 3' end of the second linker is connected to the 5' end of the fourth segment,
wherein
the third segment has 10-30 nucleotides and consists of a fourth sequence section, and the fourth sequence section is located between position 156 and position 207 of the nucleotide sequence of SEQ ID NO. 1, and
the fourth segment has 10-30 nucleotides and consists of a complementary strand of a fifth sequence section, and the fifth sequence section is located between position 211 and position 250 of the nucleotide sequence of SEQ ID NO. 1, and
the second linker consists of 1-6 thymines or peptide nucleic acids,
the backward outer primer for GAPDH nucleic acids has 10-30 nucleotides and consists of a complementary strand of a sixth sequence section, and the sixth sequence section is located between position 238 and position 275 of the nucleotide sequence of SEQ ID NO. 1; and
a primer set for detecting target nucleic acids, comprising:
a forward inner primer for target nucleic acids;
a forward outer primer for target nucleic acids;
a backward inner primer for target nucleic acids; and
a backward outer primer for target nucleic acids,
wherein a detection target of the primer set for detecting target nucleic acids differs from a detection target of the primer set for detecting GAPDH nucleic acids, and
wherein the primer set for detecting GAPDH nucleic acids and the primer set for detecting target nucleic acids are respectively used in a first loop-mediated isothermal amplification and a second loop-mediated isothermal amplification, and the first loop-mediated isothermal amplification and the second loop-mediated isothermal amplification independently comprises a standard loop-mediated isothermal amplification or a reverse transcription loop-mediated isothermal amplification, and
wherein a result of the first loop-mediated isothermal amplification is used as an internal control.

10. The target nucleic acid detection kit as claimed in claim 9, wherein
the sequence of the forward inner primer for GAPDH nucleic acids comprises the nucleotide sequence of SEQ ID NO. 2;
the sequence of the forward outer primer for GAPDH nucleic acids comprises the nucleotide sequence of SEQ ID NO. 3;
the sequence of the backward inner primer for GAPDH nucleic acids comprises the nucleotide sequence of SEQ ID NO. 4, the nucleotide sequence of SEQ ID NO. 6 or the nucleotide sequence of SEQ ID NO. 7, and
the sequence of the backward outer primer for GAPDH nucleic acids comprises the nucleotide sequence of SEQ ID NO. 5.

11. The target nucleic acid detection kit as claimed in claim 9, wherein for at least one of the forward inner primer for GAPDH nucleic acids, the forward outer primer for GAPDH nucleic acids, the backward inner primer for GAPDH nucleic acids and the backward outer primer for GAPDH nucleic acids, 1 to 10 nucleotides counted from any one position as a start point between position 4 and position 14 from the 3' end thereof is/are independently substituted by one of the following nucleotides:
inosine (I);
guanine (G); and
uracil (U).

12. The target nucleic acid detection kit as claimed in claim 11, wherein the sequence of backward inner primer for GAPDH nucleic acids comprises the nucleotide sequence of SEQ ID NO. 8 and/or the sequence of the backward outer primer for GAPDH nucleic acids comprises the nucleotide sequence of SEQ ID NO. 9.

13. The target nucleic acid detection kit as claimed in claim 11, wherein
the sequence of the forward inner primer for GAPDH nucleic acids comprises the nucleotide sequence of SEQ ID NO. 2;
the sequence of the forward outer primer for GAPDH nucleic acids comprises the nucleotide sequence of SEQ ID NO. 3;
the sequence of the backward inner primer for GAPDH nucleic acids comprises the nucleotide sequence of SEQ ID NO. 4 or the nucleotide sequence of SEQ ID NO. 8, and
the sequence of the backward outer primer for GAPDH nucleic acids comprises the nucleotide sequence of SEQ ID NO. 9.

14. The target nucleic acid detection kit as claimed in claim 9, wherein the detection target of the primer set for detecting target nucleic acids is nucleic acids of an RNA virus, and the RNA virus comprises Coronavirus, Influenza virus, Human immunodeficiency virus (HIV), Ebola virus or Hepatitis C virus (HCV).

15. The target nucleic acid detection kit as claimed in claim 14, wherein the Coronavirus comprises severe acute respiratory syndrome coronavirus (SARS-CoV), severe acute respiratory syndrome coronavirus 2 (SARS-CoV-2 or 2019-nCoV) or middle east respiratory syndrome coronavirus (MERS-CoV).

16. The target nucleic acid detection kit as claimed in claim 9, wherein the detection target of the primer set for detecting target nucleic acids is severe acute respiratory syndrome coronavirus 2 (SARS-CoV-2 or 2019-nCoV), and wherein
the forward inner primer for target nucleic acids consists of a fifth segment and a sixth segment, and the 3' end of the fifth segment is connected to the 5' end of the sixth segment, or the forward inner primer for target nucleic acids consists of a fifth segment, a third linker and a sixth segment, and the 3' end of the fifth segment is connected to the 5' end of the third linker, and the 3' end of the third linker is connected to the 5' end of the sixth segment,
wherein
the fifth segment has 10-30 nucleotides and consists of a complementary strand of a seventh sequence section, and the seventh sequence section is located between position 90 and position 134 of the nucleotide sequence of SEQ ID NO. 11, and
the sixth segment has 10-30 nucleotides and consists of an eighth sequence section, and the eighth sequence section is located between position 45 and position 82 of the nucleotide sequence of SEQ ID NO. 11, and
the third linker consists of 1-6 thymines or peptide nucleic acids,
the forward outer primer for target nucleic acids has 10-30 nucleotides and consists of a ninth sequence section, and the ninth sequence section is located between position 27 and position 64 of the nucleotide sequence of SEQ ID NO. 11,
the backward inner primer for target nucleic acids consists of a seventh segment and an eighth segment, and the 3' end of the seventh segment is connected to the 5' end of the eighth segment, or the backward inner primer for target nucleic acids consists of a seventh segment, a fourth linker and an eighth segment, and the 3' end of the seventh segment is connected to the 5' end of the fourth linker, and the 3' end of the fourth linker is connected to the 5' end of the eighth segment,
wherein
the seventh segment has 10-30 nucleotides and consists of a tenth sequence section, and the tenth sequence section is located between position 123 and position 165 of the nucleotide sequence of SEQ ID NO. 11, and
the eighth segment has 10-30 nucleotides and consists of a complementary strand of an eleventh sequence section, and the eleventh sequence section is located between position 170 and position 208 of the nucleotide sequence of SEQ ID NO. 11, and
the fourth linker consists of 1-6 thymines or peptide nucleic acids,
the backward outer primer for target nucleic acids has 10-30 nucleotides and consists of a complementary strand of a twelfth sequence section, and the nucleotide sequence of the twelfth sequence section is located between position 226 and position 263 of SEQ ID NO. 11.

17. The target nucleic acid detection kit as claimed in claim 16, wherein the primer set for detecting target nucleic acids further comprises:
a forward loop primer for target nucleic acids; and
a backward loop primer for target nucleic acids,
wherein
the forward loop primer for target nucleic acids has 10-30 nucleotides and consists of a thirteenth sequence section, and the thirteenth sequence section is located between position 63 and position 104 of the nucleotide sequence of SEQ ID NO. 11, and
the backward loop primer for target nucleic acids has 10-30 nucleotides and consists of a fourteenth sequence section, and the fourteenth sequence section is located between position 146 and position 187 of the nucleotide sequence of SEQ ID NO. 11.

18. The target nucleic acid detection kit as claimed in claim 17, wherein
the sequence of the forward inner primer for target nucleic acids comprises the nucleotide sequence of SEQ ID NO. 12,
the sequence of the forward outer primer for target nucleic acids comprises the nucleotide sequence of SEQ ID NO. 13,
the sequence of the forward loop primer for target nucleic acids comprises the nucleotide sequence of SEQ ID NO. 16,
the sequence of the backward inner primer for target nucleic acids comprises the nucleotide sequence of SEQ ID NO. 14,
the sequence of the backward outer primer for target nucleic acids comprises the nucleotide sequence of SEQ ID NO. 15, and
the sequence of the backward loop primer for target nucleic acids comprises the nucleotide sequence of SEQ ID NO. 17.

19. The target nucleic acid detection kit as claimed in claim 9, wherein the 5' end of the backward inner primer for GAPDH nucleic acids and the 5' end of the backward inner primer for target nucleic acids are labeled with a first label, the 5' end of the forward inner primer for GAPDH nucleic acids is labeled with a second label, the 5' end of the forward inner primer for target nucleic acids is labeled with a third label, and the first label, the second label and the third label are all different, and wherein the first label comprises biotin, avidin, streptavidin, digoxigenin or fluorescein, the second label comprises biotin, avidin, streptavidin, digoxigenin or fluorescein, and the third label comprises biotin, avidin, streptavidin, digoxigenin or fluorescein.

20. The target nucleic acid detection kit as claimed in claim 19, further comprising a lateral flow immunoassay test strip which, according to a flow direction of an analyte, sequentially comprises an analyte addition area, a binding area, a GAPDH detection area, a target nucleic acid detection area and a test strip control area, or sequentially comprises an analyte addition area, a binding area, a target nucleic acid detection area, a GAPDH detection area and a test strip control area, wherein the binding area has a first binding particle which has a first binding molecule and a particle linking to the first binding molecule, wherein the first binding molecule is capable of binding the first label, the GAPDH detection area is immobilized with a second binding molecule which is capable of binding the second label, the test strip control area is immobilized with a third binding molecule which is capable of binding the first binding molecule of the first binding particle, wherein the third binding molecule and the first label are the same or different, and the target nucleic acid detection area is immobilized with a fourth binding molecule which is capable of binding the third label.

21. The target nucleic acid detection kit as claimed in claim 9, further comprising a polymerase and/or nucleotide substrate, wherein the polymerase has a function of reverse transcriptase, and the polymerase is a Bst DNA polymerase and the sequence thereof comprises the amino acid sequence of SEQ ID NO. 10.

* * * * *